US011198850B2

(12) United States Patent
Sasai et al.

(10) Patent No.: US 11,198,850 B2
(45) Date of Patent: Dec. 14, 2021

(54) METHOD FOR MANUFACTURING TELENCEPHALON OR PROGENITOR TISSUE THEREOF

(71) Applicants: RIKEN, Wako (JP); Sumitomo Chemical Company, Limited, Tokyo (JP)

(72) Inventors: Yoshiki Sasai, Kobe (JP); Taisuke Kadoshima, Wako (JP); Hideya Sakaguchi, Wako (JP)

(73) Assignees: RIKEN, Wako (JP); Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 15/037,926

(22) PCT Filed: Nov. 21, 2014

(86) PCT No.: PCT/JP2014/080966
§ 371 (c)(1),
(2) Date: May 19, 2016

(87) PCT Pub. No.: WO2015/076388
PCT Pub. Date: May 28, 2015

(65) Prior Publication Data
US 2016/0289635 A1    Oct. 6, 2016

(30) Foreign Application Priority Data

Nov. 22, 2013  (JP) .............................. JP2013-242394

(51) Int. Cl.
*C12N 5/0793*    (2010.01)
*C12N 5/079*    (2010.01)

(52) U.S. Cl.
CPC ......... *C12N 5/0619* (2013.01); *C12N 5/0622* (2013.01); *C12N 2500/02* (2013.01);
(Continued)

(58) Field of Classification Search
CPC ................ C12N 5/0619; C12N 5/0622; C12N 2501/999; C12N 2501/727;
(Continued)

(56) References Cited

U.S. PATENT DOCUMENTS

2011/0091869 A1    4/2011  Sasai et al.
2013/0236436 A1    9/2013  Zhang et al.

FOREIGN PATENT DOCUMENTS

EP        1783205 A1      5/2007
JP     2003-530820 A    10/2003
(Continued)

OTHER PUBLICATIONS

Liu et al., Cell. Mol. Life Sci., 68:3995-4008, published online: Jul. 24, 2011.*
(Continued)

*Primary Examiner* — Kimberly Ballard
*Assistant Examiner* — Stacey N MacFarlane
(74) *Attorney, Agent, or Firm* — Leydig, Voit & Mayer, Ltd.

(57) ABSTRACT

The present invention provides a method of producing more mature telencephalon or a progenitor tissue thereof, in vitro, from mammalian pluripotent stem cells, comprising obtaining a telencephalon marker-positive aggregate by culturing an aggregate of pluripotent stem cells in suspension in the presence of a Wnt signal inhibitor and a TGFβ signal inhibitor, and further culturing the telencephalon marker-positive aggregate in suspension under a high oxygen partial pressure condition. In one embodiment, the suspension culture under a high oxygen partial pressure condition is performed in the presence of a Wnt signal enhancer and a bone morphogenetic factor signal transduction pathway activating substance.

25 Claims, 18 Drawing Sheets

(52) U.S. Cl.
CPC .... *C12N 2501/119* (2013.01); *C12N 2501/15* (2013.01); *C12N 2501/155* (2013.01); *C12N 2501/41* (2013.01); *C12N 2501/415* (2013.01); *C12N 2501/727* (2013.01); *C12N 2501/999* (2013.01); *C12N 2506/02* (2013.01); *C12N 2513/00* (2013.01)

(58) Field of Classification Search
CPC ............ C12N 2513/00; C12N 2501/41; C12N 2501/155; C12N 2500/02; C12N 2501/119; C12N 2501/15; C12N 2501/415; C12N 2506/02
See application file for complete search history.

(56) References Cited

FOREIGN PATENT DOCUMENTS

| WO | 2001/003743 A1 | 1/2001 |
|---|---|---|
| WO | WO 2009/148170 | * 12/2009 |
| WO | WO 2009/148170 A1 | 12/2009 |

OTHER PUBLICATIONS

Serra et al. J Biotech.,148:208-25 (2010).*
Kushima et al., Brain Research, 536(1-2): 16-22 [abstract only], (Year: 1990).*
Bain et al., Biochem J, 371:199-204, (Year: 2003).*
Thermofisher, Chemically Definied Lipid Concentrate components list retrieved from < https://www.thermofisher.com/US/en/home/technical-resources/media-formulation.249.html>. Retrieved on Oct. 4, 2020 (Year: 2020).*
Kadoshima et al., "Generation of Various Telencephalic Regions from Human Embryonic Stem Cells in Three-Dimensional Culture," *Organ Regeneration: 3D Stem Cell Culture & Manipulation, Methodsin Molecular Biology*, 1597: 1-16 (2017).
Sakaguchi et al., "Generation of functional hippocampal neurons from selforganizing human embryonic stem cell-derived dorsomedial telencephalic tissue," *Nat. Commun.*, 6: 8896 (2015).
Bielle et al. *Nature Neuroscience*, 8(8): 1002-1012 (2005).
Bystron et al., *Nature Reviews Neuroscience*, 9:110-122 (2008).
Eiraku et al. *Cell Stem Cell*, 3: 519-532 (2008).
Hebert et al., *Nature Reviews Neuroscience*, 9(9): 678-685 (2008).
Kadoshima et al. *Proc. Nat'l Acad. Sci. U.S.A.*, 110(50): 20284-20289 (2013).
Lancaster et al. *Nature*, 501(7467): 373-379 (2013).
Mariani et al. *Proc. Nat'l Acad. Sci. U.S.A.*, 109(31): 12770-12775 (2012).
Molyneaux et al. *Nature Reviews Neuroscience*, 8: 427-437 (2007).
Mondragon-Teran et al., *Biotechnology Progress*, 25(5): 1480-1488 (2009).
Nasu et al. *PLoS One*, 7(12): e53024 (2012).
Rakic, *Science*, 183(4123): 425-427 (1974).
Shen et al. *Nature Neuroscience*, 9(6): 743-751 (2006).
Watanabe et al. *Nature Biotechnology*, 25(6): 681-686 (2007).
Watanabe et al., *Nature Neuroscience*, 8(3): 288-296 (2005).
Japanese Patent Office, International Search Report in International Patent Application No. PCT/JP2014/080966 (dated Feb. 10, 2015).
Forristal et al., "Hypoxia inducible factors regulate pluripotency and proliferation in human embryonic stem cells cultured at reduced oxygen tensions," *Reproduction*, 139(1): 85-97 (2010).
Guo et al., "Culture Under Low Physiological Oxygen Conditions Improves the Sternness and Quality of Induced Pluripotent Stem Cells," *J. Cell Physiol.*, 228(11): 2159-2166 (2013).
Närvä et al., "Continuous Hypoxic Culturing of Human Embryonic Stem Cells Enhances SSEA-3 and MYC Levels," *PLoS One*, 8(11): e78847 (2013).

* cited by examiner

METHOD FOR MANUFACTURING TELENCEPHALON OR PROGENITOR TISSUE THEREOF

CROSS-REFERENCE TO RELATED APPLICATIONS

This patent application is the U.S. national phase of International Patent Application No. PCT/JP2014/080966, filed Nov. 21, 2014, which claims the benefit of Japanese Patent Application No. 2013-242394, filed on Nov. 22, 2013, which are incorporated by reference in their entireties herein.

TECHNICAL FIELD

The present invention relates to a technique for inducing differentiation of a pluripotent stem cell into telencephalon or a progenitor tissue thereof in vitro.

BACKGROUND ART

The mammalian cortex has a multilayered structure (layers I-VI) that gradually forms during fetal corticogenesis (non-patent document 1). The cortex arises from the neuroepithelium of the dorsal telencephalon (or pallium) and subsequently evaginates to form a semispherical brain vesicle on each lateral side (FIG. 17A) (non-patent document 2). The dorsocaudal side of the cortex is flanked by the cortical hem, whereas its ventrorostral side is neighbored by the lateral ganglionic eminence (LGE; striatum anlage) and septum via the paleocortex. Among the six layers found in the adult, layer I [its fetal primordium is called the marginal zone (MZ); FIG. 17B] is present, as this superficial-most layer is mainly composed of Reelin-positive Cajal-Retzius cells, which are largely derived from neighboring tissues such as the cortical hem and septum (non-patent document 3) (in the case of human cortex, some Reelin-positive cells also appear to arise directly from cortical neuroepithelium) (non-patent document 4). The rest of the cortical layers have a characteristic pattern of spatiotemporally coordinated neuronal generation, called the "inside-out" pattern: the deeper the layer, the earlier the neurons are born from cortical progenitors (FIG. 17B) (non-patent documents 5, 6).

In contrast to the large body of information available for mouse corticogenesis, a detailed understanding of early human corticogenesis remains elusive because of the limited access to human fetal brain tissues. In our previous study, we established a 3D culture method (SFEBq method) of mouse and human ES cell aggregates that recapitulate early steps of corticogenesis (non-patent documents 7-9). It has been reported that this method is also successfully applied to human iPS cell culture (non-patent document 10). Within this self-organized floating hESC-derived aggregate, cortical neuroepithelium self-form and spontaneously develop ventricular zone, cortical plate, and marginal zone by culture day 40-45. This cortical neuroepithelium was still immature in many aspects, mimicking human corticogenesis during the first trimester (FIG. 17C) (non-patent document 7).

Recently, successful results of the induction of outer ragial glial (oRG) cells within the cerebral cortical tissue having multi-layered structure derived from human pluripotent stem cells have been reported (non-patent document 11). This study uses a nonselective differentiation method which can stochastically obtain specification of brain regions. This differentiation method is characterized by rotation culture of aggregates in a spinner flask.

DOCUMENT LIST

Non-Patent Documents non-patent document 1: Molyneaux B J, Arlotta P, Menezes J R, Macklis J D. (2007) Neuronal subtype specification in the cerebral cortex. Nat Rev Neurosci. 8:427-437.
non-patent document 2: Hebert J M, Fishell G. (2008) The genetics of early telencephalon patterning: some assembly required. Nat Rev Neurosci 9:678-685.
non-patent document 3: Bielle F, et al. (2005) Multiple origins of Cajal-Retzius cells at the borders of the developing pallium. Nat Neurosci. 8:1002-1012.
non-patent document 4: Bystron I, Blakemore C, Rakic P. (2008) Development of the human cerebral cortex: Boulder Committee revisited. Nat Rev Neurosci. 9:110-122.
non-patent document 5: Rakic P. (1974) Neurons in rhesus monkey visual cortex: systematic relation between time of origin and eventual disposition. Science. 183:425-427.
non-patent document 6: Shen Q. et al. (2006) The timing of cortical neurogenesis is encoded within lineages of individual progenitor cells. Nat Neurosci 9:743-751.
non-patent document 7: Eiraku M. et al. (2008) Self-organized formation of polarized cortical tissues from ESCs and its active manipulation by extrinsic signals. Cell Stem Cell 3: 519-532.
non-patent document 8: Watanabe K. et al. (2005) Directed differentiation of telencephalic precursors from embryonic stem cells. Nat Neurosci 8:288-296.
non-patent document 9: Nasu M, et al. (2012) Robust formation and maintenance of continuous stratified cortical neuroepithelium by laminin-containing matrix in mouse ES cell culture. PLoS One 7:e53024.
non-patent document 10: Mariani J. et al. (2012) Modeling human cortical development in vitro using induced pluripotent stem cells. Proc Natl Acad Sci USA. 109: 12770-12775.
non-patent document 11: Lancaster M. et al. (2013) Cerebral organoids model human brain development and microcephaly. Proc Natl Acad Sci USA. 109:12770-12775.

SUMMARY OF THE INVENTION

Problems to be Solved by the Invention

The present invention aims to provide a technique for inducing more mature telencephalon or a progenitor tissue thereof in vitro from mammalian pluripotent stem cells.

Means of Solving the Problems

The present inventors have conducted intensive studies and succeeded in more selective, three dimensional induction of cerebral cortical tissue for a long period, by optimizing the culture conditions in a method of inducing self-organization of the human three dimensional cerebral cortex. Using this method, the dorsal-ventral polarity and anterior-posterior polarity, which is seen in the embryo in vivo, was successfully formed spontaneously in the self-organized cerebral cortex. In addition, using the exogenous signaling factor, selective induction of differentiation of a particular neural region along the dorsal-ventral or anterior-posterior axis, continuous three dimensional formation of cerebral cortical tissue with the adjacent tissue, which is consistent with the positional relationship seen in vivo, and selective self-organization of peripheral tissues of the cortex were successfully performed.

Furthermore, by continuously culturing the cerebral cortical tissues, a multilayered structure (ventricular zone, subventricular zone, outer subventricular zone, intermediate zone, subplate, deep-cortical plate, superficial-cortical layer, marginal zone) observed in the cerebral cortex of human second trimester was successfully formed three-dimensionally along the axis from the superficial portion to the deep portion.

Furthermore, by modifying the culture conditions, three dimensional induction of tissues other than cerebral cortex, such as basal ganglion, hippocampus, choroid plexus and the like, was successfully performed.

The present inventors have conducted further studies based on the above-mentioned findings and completed the present invention.

Therefore, the present invention is as follows:

[1] A method of producing a cell aggregate comprising telencephalon or a partial tissue thereof, or an progenitor tissue thereof, comprising obtaining a telencephalon marker-positive aggregate by culturing an aggregate of pluripotent stem cells in suspension in the presence of a Wnt signal inhibitor and a TGFβ signal inhibitor, and further culturing the telencephalon marker-positive aggregate in suspension under a high oxygen partial pressure condition.

[2] The production method of [1], wherein the obtained cell aggregate comprises a telencephalon partial tissue selected from the group consisting of cerebral cortex, basal ganglion, hippocampus and choroid plexus, or a progenitor tissue thereof.

[3] The production method of [1] or [2], wherein the suspension culture under a high oxygen partial pressure condition is performed in the presence of a Wnt signal enhancer.

[4] The production method of [1] or [2], wherein the suspension culture under a high oxygen partial pressure condition is performed in the presence of a Wnt signal enhancer and a bone morphogenetic factor signal transduction pathway activating substance.

[5] A method of producing a cell aggregate comprising telencephalon or a partial tissue thereof, or an progenitor tissue thereof, comprising (I) obtaining a telencephalon marker-positive aggregate by culturing an aggregate of pluripotent stem cells in suspension in the presence of a Wnt signal inhibitor and a TGFβ signal inhibitor, (II) further culturing the telencephalon marker-positive aggregate obtained in (I), in suspension in the presence of a Wnt signal enhancer and a bone morphogenetic factor signal transduction pathway activating substance, and (III) further culturing the cell aggregate obtained in (II) in suspension in the absence of a Wnt signal enhancer and a bone morphogenetic factor signal transduction pathway activating substance.

[6] The production method of [5], wherein the produced cell aggregate comprises, in continuous neuroepithelium, a cerebral cortical tissue or a progenitor tissue thereof, a choroid plexus tissue or a progenitor tissue thereof, and a hippocampal tissue or a progenitor tissue thereof.

[7] The production method of [5], wherein the produced cell aggregate comprises, in continuous neuroepithelium, a hippocampal tissue or a progenitor tissue thereof comprising a dentate gyrus tissue or a progenitor tissue thereof, and an Ammon's horn tissue or a progenitor tissue thereof.

[8] The production method of [7], wherein the hippocampal tissue or a progenitor tissue further comprises cortical hem in the continuous neuroepithelium.

[9] The production method of [5], wherein the produced cell aggregate comprises an Ammon's horn tissue or a progenitor tissue thereof.

[10] The production method of [5], wherein the suspension culture in (II) and (III) is performed under a high oxygen partial pressure condition.

[11] The production method of [1] or [2], comprising treating the cell aggregate with a shh signal agonist.

[12] The production method of [1] or [2], comprising treating the cell aggregate with FGF8.

[13] The production method of [2], wherein the obtained cell aggregate comprises a cerebral cortical tissue or a progenitor tissue thereof having a multilayered structure comprising marginal zone, cortical plate, subplate, intermediate zone, subventricular zone and ventricular zone from the superficial portion to the deep portion.

[14] The production method of [11], wherein the obtained cell aggregate comprises basal ganglion or a progenitor tissue thereof.

[15] The production method of [12], wherein the obtained cell aggregate comprises rostral cerebral cortex or a progenitor tissue thereof.

[16] The production method of any of [1]-[15], wherein the pluripotent stem cells are embryonic stem cells or induced pluripotent stem cells.

[17] The production method of any of [1]-[16], wherein the pluripotent stem cells are derived from human.

[18] The production method of any of [1]-[17], wherein the suspension culture is performed in the absence of feeder cells.

[19] A cell aggregate obtained by the production method of any of [1]-[18].

[20] A method of producing a mature hippocampal neuron, comprising dispersing the cell aggregate comprising hippocampus or a progenitor tissue thereof, which is obtained by the production method of any of [1]-[18], and further subjecting the dispersed cells to adhesion culture to induce a mature hippocampal neuron from the cells.

Effect of the Invention

According to the present invention, telencephalon or a partial tissue thereof (cerebral cortex, basal ganglion, hippocampus, choroid plexus etc.), or a progenitor tissue thereof can be selectively induced from pluripotent stem cells for a long term.

According to the present invention, a cerebral cortical tissue or a progenitor tissue thereof having a polarity of dorsal-ventral and anterior-posterior axes can be selectively induced from pluripotent stem cells.

According to the present invention, a cerebral cortical tissue or a progenitor tissue thereof having a multilayered structure of the second trimester can be selectively induced from pluripotent stem cells.

According to the present invention, a cerebral cortical tissue or a progenitor tissue thereof, a choroid plexus tissue or a progenitor tissue thereof, and a hippocampal tissue or a progenitor tissue thereof can be self-organized as adjacent tissues from pluripotent stem cells, in a continuous neuroepithelium.

According to the present invention, a hippocampal tissue or a progenitor tissue thereof containing a dentate gyrus tissue or a progenitor tissue thereof, and an Ammon's horn tissue or a progenitor tissue thereof in a continuous neuroepithelium can be induced from pluripotent stem cells.

According to the present invention, neuronal progenitor cells having the characteristics of outer ragial (oRG) glial cells, which are abundantly present in the human fetal cerebral cortex and absent in the mouse cerebral cortex, can be specifically induced on the outside of the subventricular zone, from human from pluripotent stem cells.

DESCRIPTION OF EMBODIMENTS

Figure 1:
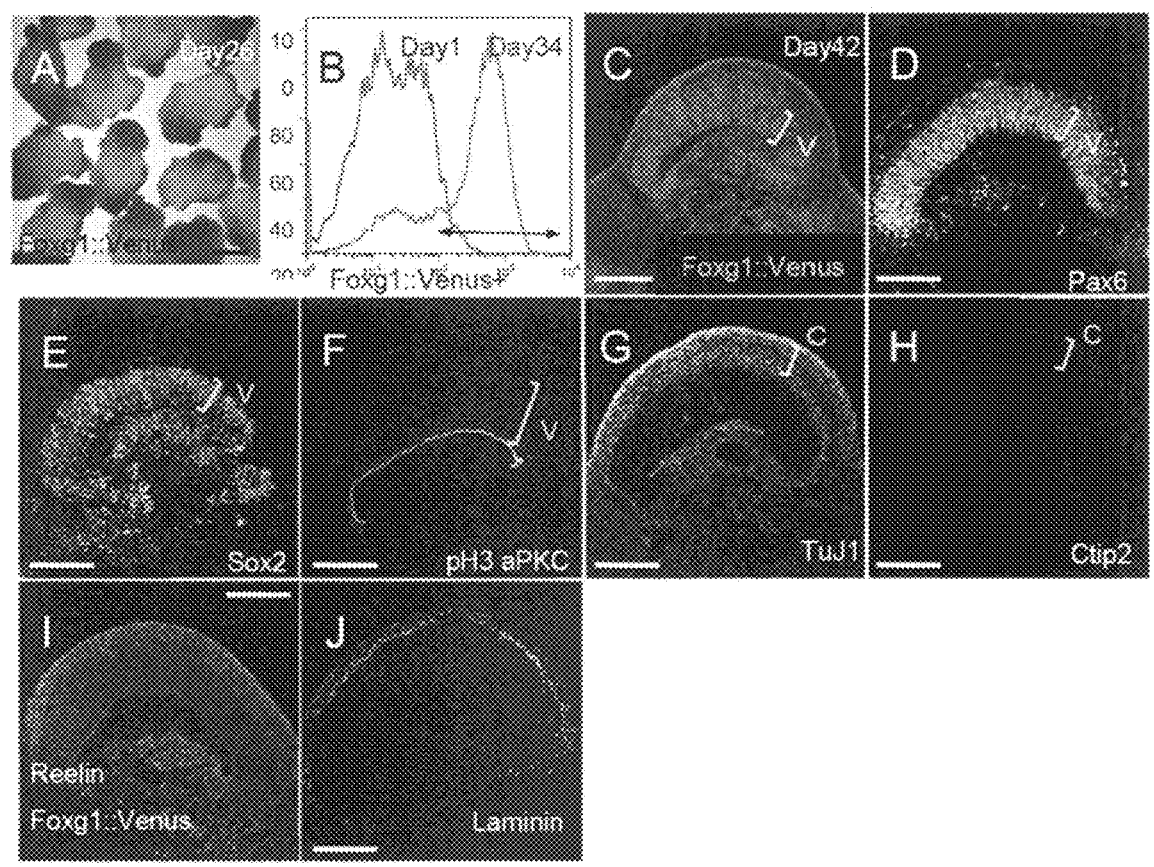
FIG. 1 shows induction of differentiation of human pluripotent stem cells into cortical progenitor tissues. (A) Foxg1::venus expression in cell aggregates on day 26. (B) Foxg1::venus expression by cells in the aggregate on day 34. (C) Semispherical neuroepithelium-like structure having a cerebral ventricle-like cavity, which is formed inside cell aggregate. (D) Pax6 expression in the luminal side of neuroepithelial structure. (E) Sox2 expression in the luminal side of the neuroepithelial structure. (F) Expression of phosphorylated histone H3 (pH3) in the most luminal side of neuroepithelial structure. (G) Tuj1 expression in the outer side of cell layer similar to ventricular zone. (H) Ctip2 expression in the outer side of cell layer similar to ventricular zone. (I) Emergence of Reelin positive Cajal-Retzius cells in the outer side of cell layer similar to ventricular zone. (J) Laminin expression near a superficial layer of aggregates.

The present invention provides a method of producing a cell aggregate comprising telencephalon or a partial tissue thereof, or a progenitor tissue thereof, comprising obtaining a telencephalon marker-positive aggregate by culturing an aggregate of pluripotent stem cells in suspension in the presence of a Wnt signal inhibitor and a TGF signal inhibitor, and further culturing the telencephalon marker-positive aggregates in suspension. Further suspension culture is preferably performed under a high oxygen partial pressure condition.

The present invention is explained in detail in the following.

(1) Pluripotent Stem Cell

The "pluripotent stem cell" refers to a cell having both the potential for differentiating into all cells constituting the body (pluripotency), and the potential for producing daughter cells having the same differentiation potency via cell division (self-replication competence).

The pluripotency can be evaluated by transplanting the cells of an evaluation target into a nude mouse, and testing the presence or absence of formation of teratoma containing each cell of three germ layers (ectoderm, mesoderm, endoderm).

Examples of the pluripotent stem cell include embryonic stem cell (ES cell), embryonic germ cell (EG cell), induced pluripotent stem cell (iPS cell) and the like, and the pluripotent stem cell is not limited as long as it has both the pluripotency and the self-replication competence. In the present invention, embryonic stem cells or induced pluripotent stem cells are preferably used.

Embryonic stem cells (ES cell) can be established by culturing, for example, a pre-implantation early embryo, an inner cell mass that constitutes the early embryo, a single blastomere and the like (Manipulating the Mouse Embryo A Laboratory Manual, Second Edition, Cold Spring Harbor Laboratory Press (1994); Thomson, J. A. et al., Science, 282, 1145-1147 (1998)). As the early embryo, an early embryo prepared by nuclear-transplanting the nucleus of a somatic cell may be used (Wilmut et al. (Nature, 385, 810 (1997)), Cibelli et al. (Science, 280, 1256 (1998)), Akira IRITANI et al. (Tanpakushitsu Kakusan Koso, 44, 892 (1999)), Baguisi et al. (Nature Biotechnology, 17, 456 (1999)), Wakayama et al. (Nature, 394, 369 (1998); Nature Genetics, 22, 127 (1999); Proc. Natl. Acad. Sci. USA, 96, 14984 (1999)), Rideout III et al. (Nature Genetics, 24, 109 (2000), Tachibana et al. (Human Embryonic Stem Cells Derived by Somatic Cell Nuclear Transfer, Cell (2013) in press)). As an early embryo, a parthenogenetic embryo may also be used (Kim et al. (Science, 315, 482-486 (2007)), Nakajima et al. (Stem Cells, 25, 983-985 (2007)), Kim et al. (Cell Stem Cell, 1, 346-352 (2007)), Revazova et al. (Cloning Stem Cells, 9, 432-449 (2007)), Revazova et al. (Cloning Stem Cells, 10, 11-24 (2008))).

Fusion ES cell obtained by cell fusion of ES cell and somatic cell is also included in the embryonic stem cells used for the method of the present invention.

Embryonic stem cells are available from appropriate organizations, and commercial products may be purchased. For example, the human embryonic stem cells KhES-1, KhES-2 and KhES-3 are available from the Institute for Frontier Medical Sciences, Kyoto University.

Embryonic germ cells (EG cell) can be established by culturing primordial germ cells in the presence of LIF, bFGF, SCF and the like (Matsui et al., Cell, 70, 841-847 (1992), Shamblott et al., Proc. Natl. Acad. Sci. USA, 95(23), 13726-13731 (1998), Turnpenny et al., Stem Cells, 21(5), 598-609, (2003)).

Induced pluripotent stem cell (iPS cell) refers to a cell that artificially acquired pluripotency and self-replication competence by contacting a somatic cell (e.g., fibroblast, skin cell, lymphocyte etc.) with a nuclear reprogramming factor. iPS cell was found for the first time by a method including introduction of nuclear reprogramming factors composed of Oct3/4, Sox2, Klf4 and c-Myc into somatic cells (e.g., fibroblast, skin cell etc.) (Cell, 126: p. 663-676, 2006). Thereafter, many researchers have made various improvements in the combination of reprogramming factors and introduction method of the factors, and various production methods of induced pluripotent stem cell have been reported.

The nuclear reprogramming factors may be configured with any substance, such as a proteinous factor or a nucleic acid that encodes the same (including forms incorporated in a vector), or a low molecular compound, as long as it is a substance (substances) capable of inducing a cell having pluripotency and self-replication competence from a somatic cell such as fibroblast and the like. When the nuclear reprogramming factor is a proteinous factor or a nucleic acid that encodes the same, preferable nuclear reprogramming factors are exemplified by the following combinations (hereinafter, only the names for proteinous factors are shown).

(1) Oct3/4, Klf4, Sox2, c-Myc (wherein Sox2 is replaceable with Sox1, Sox3, Sox15, Sox17 or Sox18. Klf4 is replaceable with Klf1, Klf2 or Klf5. Furthermore, c-Myc is replaceable with T58A (active form mutant), N-Myc or L-Myc.)
(2) Oct3/4, Klf4, Sox2
(3) Oct3/4, Klf4, c-Myc
(4) Oct3/4, Sox2, Nanog, Lin28
(5) Oct3/4, Klf4, c-Myc, Sox2, Nanog, Lin28
(6) Oct3/4, Klf4, Sox2, bFGF
(7) Oct3/4, Klf4, Sox2, SCF
(8) Oct3/4, Klf4, c-Myc, Sox2, bFGF
(9) Oct3/4, Klf4, c-Myc, Sox2, SCF Among these combinations, when use of the obtained iPS cell for therapeutic application is considered, a combination of the three factors of Oct3/4, Sox2 and Klf4 is preferable. On the other hand, when use of the iPS cell for therapeutic application is not considered (e.g., used as an investigational tool for drug discovery screening and the like), four factors consisting of Oct3/4, Klf4, Sox2 and c-Myc, or 5 factors by adding Lin28 or Nanog thereto are preferable.

iPS cell is preferably used for autologous transplantation.

A pluripotent stem cell obtained by modifying genes in a chromosome by a known genetic engineering method can also be used in the present invention. The pluripotent stem cell may be a cell wherein a labeling gene (e.g., fluorescent protein such as GFP etc.) has been knocked in a gene encoding a differentiation marker in an in-frame manner by a known method, which cell can be identified to have reached the corresponding differentiation stage by using the expression of the labeling gene as an index.

As the pluripotent stem cell, warm-blooded animal pluripotent stem cells, preferably mammalian pluripotent stem cells, can be used. Mammals include, for example, laboratory animals, including rodents such as mice, rats, hamsters and guinea pigs, and rabbits; domestic animals such as pigs, cattle, goat, horses, and sheep; companion animals such as dogs and cats; primates such as humans, monkeys, orangutans, and chimpanzees. Pluripotent stem cell is preferably pluripotent stem cell of rodents (mouse, rat etc.) or primates (human etc.) and most preferably human pluripotent stem cell.

Pluripotent stem cells can be cultured for maintenance by a method known per se. For example, from the aspects of clinical application, pluripotent stem cells are preferably maintained by serum-free culture using serum alternatives such as Knockout™ Serum Replacement (KSR) and the like, or feeder-free cell culture.

The pluripotent stem cells to be used in the present invention are preferably isolated. Being "isolated" means that an operation to remove factors other than the target cell or component has been performed, and the cell or component is no longer in a natural state. The purity of the "isolated human pluripotent stem cells" (percentage of the number of human pluripotent stem cells to the total cell number) is generally not less than 70%, preferably not less than 80%, more preferably not less than 90%, further preferably not less than 99%, most preferably 100%.

(2) Formation of Pluripotent Stem Cell Aggregate

A pluripotent stem cell aggregate can be obtained by culturing dispersed pluripotent stem cells under conditions that are non-adhesive to the culture vessel (i.e., culturing in suspension), and assembling plural pluripotent stem cells to allow for aggregate formation.

A culture vessel used for the aggregate formation is not particularly limited, and examples thereof include flasks, tissue culture flasks, dishes, Petri dishes, tissue culture dishes, multi-dishes, microplates, micro-well plates, micropores, multi-plates, multi-well plates, chamber slides, Petri dishes, tubes, trays, culture bags, and roller bottles. To enable culture under non-adhesive conditions, the culture vessel is preferably non-cell-adherent. Useful non-cell-adherent culture vessels include culture vessels whose surfaces have been artificially treated to be cell non-adherent, culture vessels whose surfaces have not undergone an artificial treatment for improving the cell adhesiveness (e.g., coating treatment with an extracellular matrix and the like), and the like.

The medium to be used for aggregate formation can be prepared using a medium used for culturing animal cells as a basal medium. The basal medium is not particularly limited as long as it can be used for culture of animal cells and may be BME medium, BGJb medium, CMRL 1066 medium, Glasgow MEM medium, Improved MEM Zinc Option medium, IMDM medium, Medium 199 medium, Eagle MEM medium, αMEM medium, DMEM medium, ham medium, Ham's F-12 medium, RPMI 1640 medium, Fischer's medium, a mixed medium thereof and the like.

To avoid an adverse influence on the differentiation induction of a pluripotent stem cell into telencephalon or a partial tissue thereof, or a precursor tissue thereof, the medium used for aggregate formation is preferably a serum-free medium. The serum-free medium means a medium free of an unadjusted or unpurified serum. A medium containing purified components derived from blood and components derived from animal tissue (e.g., cytokine) corresponds to a serum-free medium.

The medium used for aggregate formation may contain a serum alternative. The serum alternative can, for example, be one comprising as appropriate an albumin, transferrin, fatty acids, collagen precursor, trace elements, 2-mercaptoethanol or 3'-thiolglycerol, or their equivalents and the like. Such a serum alternative can be prepared by, for example, a method described in WO98/30679. To facilitate easier implementation of the method of the present invention, commercially available serum alternatives can be utilized. Examples of such commercially available serum alternatives include Knockout Serum Replacement (KSR, produced by Invitrogen), Chemically-defined Lipid Concentrated (produced by Gibco Company) and Glutamax (produced by Gibco Company).

A medium to be used for aggregate formation can contain other additive as long as induction of differentiation of pluripotent stem cells into telencephalon or a partial tissue thereof, or a precursor tissue thereof is not adversely influenced. Examples of the additive include, but are not limited to, insulin, iron source (e.g., transferrin etc.), mineral (e.g., sodium selenate etc.), saccharides (e.g., glucose etc.), organic acid (e.g., pyruvic acid, lactic acid etc.), serum protein (e.g., albumin etc.), amino acid (e.g., L-glutamine etc.), reducing agent (e.g., 2-mercaptoethanol etc.), vitamins (e.g., ascorbic acid, d-biotin etc.), antibiotic (e.g., streptomycin, penicillin, gentamicin etc.), buffering agent (e.g., HEPES etc.) and the like.

A medium to be used for aggregate formation may be a below-mentioned medium used for induction of differentiation of pluripotent stem cells into telencephalon or a partial tissue thereof, or a precursor tissue thereof.

For formation of a pluripotent stem cell aggregate, pluripotent stem cells are collected from passage culture and dispersed to a single cell state or near single cell state. Pluripotent stem cells are dispersed with an appropriate cell dissociation solution. Examples of the cell dissociation solution include EDTA; protease such as trypsin, collagenase IV, metalloproteinase and the like, and the like, which are used alone or in an appropriate combination. Of these, one showing low cell toxicity is preferable, and examples of such cell dissociation solution include commercially available products such as DISPASE (EIDIA), TrypLE (Invitrogen), Accutase (MILLIPORE) and the like. The dispersed pluripotent stem cells are suspended in the above-mentioned medium.

To suppress cell death of pluripotent stem cells (particularly, human pluripotent stem cells) induced by dispersion, it is preferable to add an inhibitor of Rho-associated coiled-coil kinase (ROCK) from the start of cultivation (JP-A-2008-99662). A ROCK inhibitor is added, for example, within 15 days, preferably 10 days, more preferably 6 days, from the start of the culture. Examples of the ROCK inhibitor include Y-27632 ((+)-(R)-trans-4-(1-aminoethyl)-N-(4-pyridyl)cyclohexanecarboxamide dihydrochloride) and the like. The concentration of the ROCK inhibitor used for suspension culture is a concentration capable of suppressing cell death of pluripotent stem cells induced by dispersion. For example, for Y-27632, this concentration is normally about 0.1 to 200 µM, preferably about 2 to 50 µM. The concentration of the ROCK inhibitor may be changed in the addition period thereof and, for example, the concentration may be reduced to half in the latter half period.

A suspension of the dispersed pluripotent stem cells is seeded in the above-mentioned culture vessel and the dispersed pluripotent stem cells are cultured under conditions that are non-adhesive to the cell culture vessel, whereby the plural pluripotent stem cells are assembled to form an aggregate. In this case, dispersed pluripotent stem cells may be seeded in a comparatively large culture vessel such as a 10-cm dish to simultaneously form plural pluripotent stem cell aggregates in one culture compartment. However, the size of aggregates, and the number of pluripotent stem cells contained therein may vary widely, and such variation may cause difference in the levels of differentiation of pluripotent stem cells into telencephalon or a partial tissue thereof, or a precursor tissue thereof between aggregates, which in turn may lower the efficiency of differentiation induction. Therefore, it is preferable to rapidly coagulate the dispersed pluripotent stem cells to form one aggregate in one culture compartment. Examples of the method for rapidly coagulating the dispersed pluripotent stem cells include the following methods:

(1) A method including enclosing dispersed pluripotent stem cells in a culture compartment having a comparatively small volume (e.g., not more than 1 ml, not more than 500 µl, not more than 200 µl, not more than 100 µl) to form one aggregate in the compartment. Preferably, the culture compartment is stood still after enclosing the dispersed pluripotent stem cells. Examples of the culture compartment include, but are not limited to, a well in a multi-well plate (384-well, 192-well, 96-well, 48-well, 24-well etc.), micropore, chamber slide and the like, tube, a droplet of a medium in hanging drop method and the like. The dispersed pluripotent stem cells enclosed in the compartment are precipitated on one spot due to the gravity, or the cells adhere to each other to form one aggregate in one culture compartment. The shape of the bottom of the multiwall plate, micropore, chamber slide, tube and the like is preferably U-bottom or V-bottom to facilitate precipitation of the dispersed pluripotent stem cells on one spot.

(2) A method including placing dispersed pluripotent stem cells in a centrifugation tube, centrifuging same to allow for precipitation of pluripotent stem cells on one spot, thereby forming one aggregate in the tube.

The number of pluripotent stem cells to be seeded in one culture compartment is not particularly limited as long as one aggregate is formed per one culture compartment, and differentiation of pluripotent stem cells into telencephalon or a partial tissue thereof, or a precursor tissue thereof can be induced in the aggregate by the method of the present invention. Generally, about $1 \times 10^3$-about $5 \times 10^4$, preferably about 1×10³-about 2×10⁴, more preferably about 2×10³-about 1.2×10⁴ of pluripotent stem cells are seeded in one culture compartment. Then, by rapidly coagulating the pluripotent stem cells, one cell aggregate generally composed of about 1×10³-about 5×10⁴, preferably about 1×10³-about 2×10⁴, more preferably about 2×10³-about 1.2×10⁴ pluripotent stem cells is formed per one culture compartment.

The time up to aggregate formation can be determined as appropriate as long as one aggregate is formed per one compartment, and differentiation of pluripotent stem cells into cerebral cortex or a precursor tissue thereof can be induced in the aggregate by the method of the present invention. By shortening the time, efficient induction of differentiation into the object cerebral cortical tissue or a precursor tissue thereof is expected, and therefore, said time is preferably shorter. Preferably, pluripotent stem cell aggregate is formed within 24 hr, more preferably within 12 hr, further preferably within 6 hr, most preferably in 2-3 hr. The time up to the aggregate formation can be adjusted as appropriate by choosing a tool for cell aggregation, centrifugal conditions and the like by those skilled in the art.

Other culturing conditions such as culturing temperature and $CO_2$ concentration at the time of aggregate formation can be set as appropriate. The culturing temperature is not particularly limited, and is, for example, about 30 to 40° C., preferably about 37° C. The $CO_2$ concentration is, for example, about 1 to 10%, preferably about 5%.

Furthermore, plural culture compartments under the same culture conditions are prepared and one pluripotent stem cell aggregate is formed in each culture compartment, whereby a qualitatively uniform population of pluripotent stem cell aggregates can be obtained. Whether pluripotent stem cell aggregates are qualitatively uniform can be evaluated on the basis of the size of the aggregate mass and the number of cells therein, macroscopic morphology, microscopic morphology and homogeneity thereof as analyzed by histological staining, the expression of differentiation and un-differentiation markers and homogeneity thereof, the regulation of the expression of differentiation markers and synchronicity thereof, reproducibility of differentiation efficiency among aggregates, and the like. In one embodiment, a population of the pluripotent stem cell aggregates to be used in the method of the present invention contains a uniform number of pluripotent stem cells in the aggregates. A population of pluripotent stem cell aggregates being "uniform" in a particular parameter means that not less than 90% of the total aggregates in a population thereof falls within the range of mean of the parameter in the aggregate population ±10%, preferably ±5%.

(3) Induction of Telencephalon or Partial Tissue Thereof, or Precursor Tissue Thereof The production method of the present invention comprises culturing an aggregate of pluripotent stem cells in suspension in the presence of a Wnt signal inhibitor and a TGFβ signal inhibitor to give a telencephalon marker-positive aggregate (the first culture step), and further culturing the telencephalon marker-positive aggregate in suspension (the second culture step). The suspension culture in the second culture step is preferably performed under a high oxygen partial pressure condition. In the first culture step, the direction of differentiation from pluripotent stem cells into telencephalon region is committed, whereby expression of a telencephalon marker gene is induced. By subjecting the obtained telencephalon marker-positive aggregate to the second culture step, further differentiation into telencephalon or a partial tissue thereof, or a progenitor tissue thereof is induced.

Examples of the telencephalon marker include, but are not limited to, Foxg1 (also called Bf1), Six3 and the like. A telencephalon marker-positive aggregate contains cells expressing at least one telencephalon marker. In a preferable embodiment, the telencephalon marker-positive aggregate is a Foxg1 positive aggregate. In the telencephalon marker-positive aggregate, for example, not less than 30%, preferably not less than 50%, more preferably not less than 70% of the cells contained in the aggregate are telencephalon marker-positive.

A partial tissue of telencephalon includes, for example, cerebral cortex, basal ganglion, hippocampus, choroid plexus and the like.

According to the present invention, telencephalon or a partial tissue thereof, or a progenitor tissue thereof is self-organized within an aggregate of pluripotent stem cells. According to one embodiment of the present invention, an aggregate of pluripotent stem cells is cultured in suspension in the presence of a Wnt signal inhibitor and a TGFβ signal inhibitor, to give a telencephalon marker-positive aggregate (e.g., Foxg1 positive aggregate), and the telencephalon marker-positive aggregate (e.g., Foxg1 positive aggregate) is further cultured in suspension (preferably under a high oxygen partial pressure condition), whereby a telencephalon marker-positive neuroepithelium-like structure is formed in the aggregate. In one embodiment, not less than 70% of the cells contained in the aggregate containing the neuroepithelium-like structure are telencephalon marker-positive (e.g., Foxg1 positive). In one embodiment, the neuroepithelium-like structure formed in the aggregate shows a pseudostratified columnar epithelial structure having a cerebral ventricle-like cavity in the inside. In one embodiment, the neuroepithelium structure has a Pax6 positive and Sox2 positive cell layer in the luminal side, and contains phosphorylated Histone H3 positive mitotic cells in its innermost part. These structures are similar to the ventricular zone of cerebral cortex in human early trimester. In one embodiment, outside of the neuroepithelium-like cell layer similar to ventricular zone contains cells which express a postmitotic neuron marker Tuj1 and early cortical plate markers Ctip2 and Tbr1. These may contain Reelin-positive Cajal-Retzius cells, which are neuron in layer I of cerebral cortex, and a Laminin-rich layer near the superficial layer. That is, in a preferable embodiment, the aggregate obtained by the production method of the present invention may contain a cortical progenitor tissue.

"Culturing in suspension" of a pluripotent stem cell aggregate refers to culturing an aggregate of pluripotent stem cells in a medium under conditions that are non-adhesive to the culture vessel. This enables three dimensional formation which is difficult to achieve in conventional adhesion culture.

The medium used for suspension culture contains a Wnt signal inhibitor and TGFβ signal inhibitor. Due to the action of the Wnt signal inhibitor and the TGFβ signal inhibitor, differentiation induction of pluripotent stem cells into a telencephalon region can be efficiently performed.

The Wnt signal inhibitor is not particularly limited, as far as it is capable of suppressing the signal transduction mediated by Wnt. Wnt signal inhibitors include, but are not limited to, for example, IWR-1-endo(4-[(3aR,4S,7R,7aS)-1,3,3a,4,7,7a-hexahydro-1,3-dioxo-4,7-methano-2H-isoindol-2-yl]-N-8-quinolinyl-benzamide), IWP-2, XAV939, Dkk1, Cerberus protein, Wnt receptor inhibitors, soluble Wnt receptors, Wnt antibodies, casein kinase inhibitors, and dominant negative Wnt protein; in particular, IWR-1-endo is preferable.

The TGFβ signal inhibitor is not particularly limited, as far as it is capable of suppressing the signal transduction mediated by TGFβ. TGFβ signal inhibitors include, but are not limited to, for example, SB431542 (4-(5-benzol[1,3]dioxol-5-yl-4-pyridin-2-yl-1H-imidazol-2-yl)-benzamide), LY-364947, SB-505, A-83-01 and the like; in particular, SB431542 is preferable.

A preferable combination of a Wnt signal inhibitor and a TGFβ signal inhibitor is IWR-1-endo and SB431542.

The concentration of the Wnt signal inhibitor and TGFβ signal inhibitor in the medium can be appropriately determined within a range in which differentiation of pluripotent stem cells into telencephalon region can be induced in the aggregate. When IWR-1-endo is used as a Wnt signal inhibitor, the concentration thereof is generally 0.1-50 μM, preferably 0.3-5 μM. When SB431542 is used as a TGFβ signal inhibitor, the concentration thereof is generally 0.1-100 μM, preferably 1-10 μM.

The medium to be used for suspension culture of aggregate can be prepared using a medium used for culturing animal cells as a basal medium. The basal medium is not particularly limited as long as it can be used for culture of animal cells and may be BME medium, BGJb medium, CMRL 1066 medium, Glasgow MEM medium, Improved MEM Zinc Option medium, IMDM medium, Medium 199 medium, Eagle MEM medium, αMEM medium, DMEM medium, ham medium, Ham's F-12 medium, RPMI 1640 medium, Fischer's medium, Neurobasalmedium, a mixed medium thereof and the like. Preferably, Glasgow MEM medium is used.

To avoid an adverse influence on the induction of differentiation of pluripotent stem cells into telencephalon or a partial tissue thereof, or a precursor tissue thereof, the medium used for culturing aggregates in suspension is preferably a serum-free medium.

The medium used for suspension culture of aggregates may contain a serum alternative. The serum alternative may, for example, be one comprising as appropriate an albumin, transferrin, fatty acids, collagen precursor, trace elements, 2-mercaptoethanol or 3'-thiolglycerol, or their equivalents and the like. Such a serum alternative can be prepared by, for example, a method described in WO98/30679. To facilitate easier implementation of a method of the present invention, commercially available serum alternatives can be utilized. Examples of such commercially available serum alternatives include KSR (Knockout Serum Replacement) (produced by Invitrogen), Chemically-defined Lipid Concentrated (produced by Gibco Company) and Glutamax (produced by Gibco Company).

The medium used for culturing the aggregate in suspension can contain other additive as long as an adverse influence is not exerted on the induction of differentiation of pluripotent stem cells into telencephalon or a partial tissue thereof, or a precursor tissue thereof. Examples of the additive include, but are not limited to, insulin, iron source (e.g., transferrin etc.), mineral (e.g., sodium selenate etc.), saccharides (e.g., glucose etc.), organic acid (e.g., pyruvic acid, lactic acid etc.), serum protein (e.g., albumin etc.), amino acid (e.g., L-glutamine etc.), reducing agent (e.g., 2-mercaptoethanol etc.), vitamins (e.g., ascorbic acid, d-biotin etc.), antibiotic (e.g., streptomycin, penicillin, gentamicin etc.), buffering agent (e.g., HEPES etc.) and the like.

In one embodiment, to avoid an adverse influence on the induction of differentiation of pluripotent stem cells into telencephalon or a partial tissue thereof, or a precursor tissue thereof, the medium used for culturing aggregates in suspension is preferably a growth-factor-free chemically defined medium (gfCDM) added with a serum alternative (KSR etc.). The "growth factor" here encompasses pattern formation factors such as Fgf, Wnt, Nodal, Notch, Shh and the like; insulin and lipid-rich albumin.

Other culturing conditions for suspension culture of the aggregate, such as culturing temperature, $CO_2$ concentration and $O_2$ concentration, can be set as appropriate. The culturing temperature is not particularly limited, and is, for example, about 30 to 40° C., preferably about 37° C. The $CO_2$ concentration is, for example, about 1 to 10%, preferably about 5%. The $O_2$ concentration is, for example, about 20%.

The first culture step is performed for a period sufficient for committing the direction of differentiation into a telencephalon region and inducing a telencephalon marker-positive aggregate (e.g., Foxg1 positive aggregate). A telencephalon marker-positive aggregate can be detected, for example, by RT-PCR or immunohistochemistry using a telencephalon marker specific antibody. For example, it is performed until not less than 50%, preferably not less than 70%, of the cell aggregates in the culture become telencephalon marker-positive. Since the culture period may vary depending on the animal species of pluripotent stem cells, and the kind of Wnt signal inhibitor and TGFβ signal inhibitor, it cannot be generally specified. However, when human pluripotent stem cells are used, for example, the first culture step is 15-20 days (e.g., 18 days).

In the second culture step, the telencephalon marker-positive aggregate obtained in the first culture step are further subjected to suspension culture, whereby a cell aggregate comprising telencephalon or a partial tissue thereof, or a progenitor tissue thereof is obtained. The suspension culture in the second culture step is preferably performed under a high oxygen partial pressure condition. By further culturing telencephalon marker-positive aggregates in suspension under a high oxygen partial pressure condition, long term maintenance culture of the ventricular zone contained in the aggregates is achieved, thus enabling efficient differentiation induction into telencephalon or a partial tissue thereof, or a progenitor tissue thereof.

The high oxygen partial pressure condition means an oxygen partial pressure condition exceeding the oxygen partial pressure in the air (20%). The oxygen partial pressure in the second culture step is, for example, 30-60%, preferably 35-60%, more preferably 38-60%.

The medium to be used in the second culture step can be prepared using a medium used for culturing animal cells as a basal medium, as for the medium used for the first culture step. The basal medium is not particularly limited as long as it can be used for culture of animal cells and may be BME medium, BGJb medium, CMRL 1066 medium, Glasgow MEM medium, Improved MEM Zinc Option medium, IMDM medium, Medium 199 medium, Eagle MEM medium, αMEM medium, DMEM medium, ham medium, Ham's F-12 medium, RPMI 1640 medium, Fischer's medium, a mixed medium thereof and the like. DMEM medium is preferably used.

In the second culture step, the Wnt signal inhibitor and the TGFβ signal inhibitor used in the first culture step are not necessary. In one embodiment, the medium used in the second culture step does not contain a Wnt signal inhibitor and a TGFβ signal inhibitor.

The medium to be used in the second culture step preferably contains an N2 supplement as a serum replacement to promote differentiation induction into telencephalon or a partial tissue thereof, or a progenitor tissue thereof. The N2 supplement is a known serum substitute composition containing insulin, transferrin, progesterone, putrescine and sodium selenite, and can be purchased from Gibco/Invitrogen and the like. The amount of the N2 supplement to be added can be appropriately determined so that differentiation induction into telencephalon or a partial tissue thereof, or a progenitor tissue thereof can be promoted.

The medium to be used in the second culture step preferably contains a chemically defined lipid concentrate (Chemically Defined Lipid Concentrate) for the maintenance culture of the ventricular zone for a long term. The Chemically Defined Lipid Concentrate is a lipid mixture containing cholesterol, DL-α-tocopherol, arachidonic acid, linolenic acid, linoleic acid, myristic acid, oleic acid, palmitic acid, palmitoleic acid, and stearic acid, each of which is purified. The Chemically Defined Lipid Concentrate may be a commercially available one and can be purchased from, for example, Gibco/Invitrogen and the like.

A medium to be used for suspension culture of aggregate can contain other additive as long as induction of differentiation of pluripotent stem cells into telencephalon or a partial tissue thereof, or a precursor tissue thereof is not adversely influenced. Examples of the additive include, but are not limited to, insulin, iron source (e.g., transferrin etc.), mineral (e.g., sodium selenate etc.), saccharides (e.g., glucose etc.), organic acid (e.g., pyruvic acid, lactic acid etc.), serum protein (e.g., albumin etc.), amino acid (e.g., L-glutamine etc.), reducing agent (e.g., 2-mercaptoethanol etc.), vitamins (e.g., ascorbic acid, d-biotin etc.), antibiotic (e.g., streptomycin, penicillin, gentamicin etc.), buffering agent (e.g., HEPES etc.) and the like.

In one embodiment, to avoid an adverse influence on the induction of differentiation of pluripotent stem cells into telencephalon or a partial tissue thereof, or a precursor tissue thereof, the medium used for culturing aggregate in suspension is preferably a growth-factor-free chemically defined medium (gfCDM) added with a serum alternative (KSR etc.). The "growth factor" here encompasses pattern formation factors such as Fgf, Wnt, Nodal, Notch, Shh and the like; insulin and lipid-rich albumin.

In a preferable embodiment, the medium for the second culture step contains N2 supplement and Chemically Defined Lipid Concentrate.

In one embodiment, the medium for the second culture step is a serum-free medium.

In one embodiment, the medium for the second culture step may contain a serum. Serum may contribute to the long-term maintenance culture of the ventricular zone. Examples of the serum include, but are not limited to, FBS and the like. The serum is preferably inactivated. The concentration of the serum in the medium can be appropriately adjusted within the range contributing to the long-term maintenance culture of the ventricular zone, and is generally 1-20% (v/v).

In one embodiment, the medium for the second culture step may contain heparin. Heparin may contribute to the long-term maintenance culture of the ventricular zone. The concentration of the heparin in the medium can be appropriately adjusted within the range contributing to the long-term maintenance culture of the ventricular zone, and is generally 0.5-50 μg/ml, preferably 1-10 μg/ml (e.g., 5 μg/ml).

In one embodiment, the medium for the second culture step may contain an extracellular matrix component. The extracellular matrix may contribute to the long term maintenance culture of the ventricular zone. The "extracellular matrix component" refers to various components generally found in an extracellular matrix. In the method of the present invention, a basement membrane component is preferable. Examples of the main component of basement membrane include type IV collagen, laminin, heparan sulfate proteoglycan, and entactin. The extracellular matrix component to be added to a medium may be a commercially available one and, for example, Matrigel (BD Bioscience), human laminin (Sigma Ltd.) and the like can be mentioned. Matrigel is a basement membrane preparation derived from Engelbreth Holm Swarn (EHS) mouse sarcoma. The main component of Matrigel is type IV collagen, laminin, heparan sulfate proteoglycan, and entactin. In addition to these, TGF-β, fibroblast growth factor (FGF), tissue plasminogen activator, and growth factors naturally produced by EHS tumor are contained. The "growth factor reduced product" of Matrigel has a lower growth factor concentration than common Matrigel, and the standard concentration thereof is <0.5 ng/ml for EGF, <0.2 ng/ml for NGF, <5 pg/ml for PDGF, 5 ng/ml for IGF-1, and 1.7 ng/ml for TGF-β. In the method of the present invention, use of a growth factor reduced product is preferable.

The concentration of the extracellular matrix component in the medium can be appropriately adjusted within the range contributing to the long-term maintenance culture of the ventricular zone. When Martigel is used, it is generally added in a volume of 1/500-1/20, further preferably 1/100, of the culture medium.

In one embodiment, the medium for the second culture step contains serum and heparin in addition to N2 supplement and Chemically Defined Lipid Concentrate. In this embodiment, the medium may further contain an extracellular matrix. The medium for this embodiment is suitable for the observation of differentiation induction into telencephalon or a partial tissue thereof, or a progenitor tissue thereof for a long term. In this case, a medium containing N2 supplement, Chemically Defined Lipid Concentrate, serum and heparin (optionally further, extracellular matrix) may be used over the whole range of the second culture step, or the medium for this embodiment may be used only a part of the period. In one embodiment, in the second culture step, a medium containing N2 supplement and Chemically Defined Lipid Concentrate and not containing serum, heparin and extracellular matrix is first used, and may be changed to a medium containing N2 supplement, Chemically Defined Lipid Concentrate, serum, heparin, (optionally, extracellular matrix) on the way (e.g., after a stage when a semispherical neuroepithelium-like structure having a cerebral ventricle-like cavity (pseudostratified columnar epithelium) is formed in Foxg1 positive aggregates).

Other culturing conditions such as culturing temperature and $CO_2$ concentration in the second culture step can be set as appropriate. The culturing temperature is, for example, about 30 to 40° C., preferably about 37° C. The $CO_2$ concentration is, for example, about 1 to 10%, preferably about 5%.

The second culture step is performed for at least a period sufficient for forming a semispherical neuroepithelium-like structure having a cerebral ventricle-like cavity (pseudostratified columnar epithelium) in the Foxg1 positive aggregate. The neuroepithelium-like structure can be confirmed by a microscopic observation. Since the culture period may vary depending on the animal species of pluripotent stem cells, the kind of Wnt signal inhibitor and TGFβ signal inhibitor and the like, it cannot be generally specified.

However, when human pluripotent stem cells are used, for example, the second culture step is at least 15-20 days (e.g., 17 days).

In the method of the present invention, stable self-organization of telencephalon can be induced in a cell aggregate by performing the second culture step for a long term (e.g., not less than 20 days, preferably not less than 50 days, more preferably not less than 70 days). When the second culture step is continuously performed, the differentiation stage of telencephalon or a partial tissue thereof, or a progenitor tissue thereof contained in the cell aggregate proceeds along with the progress of time. Therefore, the second culture step is preferably performed continuously until a desired differentiation stage is reached.

In one embodiment, the second culture step is performed until a cerebral cortical tissue or a progenitor tissue thereof shows a multilayered structure containing marginal zone, cortical plate, subplate, intermediate zone, subventricular zone and ventricular zone from the superficial portion to the deep portion in the cell aggregate. Importantly, the cerebral cortex or a progenitor tissue thereof having the multilayered structure is self-organized in the method of the present invention. Since the culture period necessary for showing the multilayered structure may vary depending on the animal species of pluripotent stem cells, the kind of Wnt signal inhibitor and TGFβ signal inhibitor and the like, it cannot be generally specified. However, when human pluripotent stem cells are used, for example, the second culture step is performed for not less than 52 days. In general, the marginal zone contains Reelin-positive Cajal-Retzius cells and laminin. The cortical plate includes Tbr1 positive Ctip2 positive deep-cortical plate, and a superficial-cortical plate containing a neuron expressing Satb2, and the superficial-cortical plate contacts the marginal zone. When the differentiation of cortical progenitor tissues has not proceeded sufficiently, the superficial-cortical plate may not be clearly formed; however, when the differentiation proceeds sufficiently (e.g., after not less than 73 days of the second culture step), both the deep-cortical plate and the superficial-cortical plate are clearly formed. A subplate is formed immediately underneath the cortical plate, and contains Calretinin positive and MAP2 positive cells with many neurites. The intermediate zone is a layer between the subventricular zone and the cortical plate and having sparse cells. The subventricular zone is characterized by being Tbr2 positive. The ventricular zone is characterized by being Sox2 positive and Pax6 positive. In one embodiment, the second culture step is performed until a cerebral cortical tissue or a progenitor tissue thereof shows a multilayered structure containing marginal zone, superficial-cortical plate, deep-cortical plate, subplate, intermediate zone, outer subventricular zone, subventricular zone and ventricular zone from the superficial portion to the deep portion in the cell aggregate (e.g., not less than 73 days). Such multilayered structure is seen in vivo in the cerebral cortex during the human second trimester.

Interestingly, when human pluripotent stem cells are used in the method of the present invention, phosphorylated Vimentin positive, Tbr2 negative, Sox2 positive, Pax6 positive neural stem cells/progenitor cells are contained in the outer subventricular zone (oSVZ). Neural stem cells/progenitor cells have the same characteristics as those of the outer ragial glial cells (oRG) which are abundantly present in the cerebral cortex of human fetus, but scarcely present in the mouse cerebral cortex. According to the present invention, therefore, emergence of oRG-like cells in the outer subventricular zone, which is a phenomenon specific to human, can be recapitulated in vitro.

Importantly, in the method of the present invention, the dorsal-ventral and anterior-posterior axes of the cerebral cortex is spontaneously formed. In one embodiment, for example, in the cortical ventricular zone contained in cell aggregate obtained in the second culture step, the expression of dorsocaudal marker (CoupTF1, Lhx2 etc.) shows a gradient of being stronger on one side and weaker on the opposite side, and the expression of ventrorostral marker (e.g., Sp8) shows a reverse gradient pattern from that of the dorsocaudal marker. Alternatively, in one embodiment, a region strongly expressing the dorsocaudal marker (e.g., CoupTF1, Lhx2) in the cortical ventricular zone is formed adjacent to a region expressing the cortical hem marker (e.g., Zic1, Otx2).

Suspension culture of the aggregate may be performed in the presence or absence of feeder cells as long as the differentiation induction from pluripotent stem cells into telencephalon or a partial tissue thereof, or a precursor tissue thereof is possible by the method of the present invention. To avoid contamination with undefined factors, the suspension culture of aggregate is preferably performed in the absence of feeder cells.

In the method of the present invention, a culture vessel to be used for suspension-culture of aggregates is not particularly limited. Such culture vessel includes, for example, flasks, tissue culture flasks, dishes, Petri dishes, tissue culture dishes, multi-dishes, microplates, micro-well plates, micropores, multi-plates, multi-well plates, chamber slides, Petri dishes, tubes, trays, culture bags, and roller bottles. To enable culture under non-adhesive conditions, the culture vessel is preferably non-cell-adherent. Useful non-cell-adherent culture vessels include culture vessels whose surfaces have been artificially treated to be non-cell-adherent, culture vessels whose surfaces have not undergone an artificial treatment for improving the cell adhesiveness (e.g., coating treatment with an extracellular matrix and the like), and the like.

As an culture vessel to be used for suspension culture of aggregates, an oxygen-permeable one may be used. Using an oxygen-permeable culture vessel, oxygen supply to the aggregates may be improved, thus contributing to the maintenance culture of the ventricular zone for a long term. Particularly, in the second culture step, since cell aggregate may grow large in size to cause a risk of not being able to supply oxygen sufficiently to the cells in the aggregates (e.g., cells in the ventricular zone), use of an oxygen-permeable culture vessel is preferable.

In the suspension culture of aggregate, the aggregate may be subjected to static culture or may be intentionally moved by rotation culture or shaking culture, as long as a non-adhered state of the aggregate to the culture vessel can be maintained. However, it is not necessary to intentionally move aggregates by rotation culture or shaking culture. In one embodiment, the suspension culture in the production method of the present invention is performed by static culture. Static culture refers to a culture method for cultivating aggregate in a state free of intentional movement of the aggregate. It may happen that aggregate move, for example, due to the convection of the medium along with topical changes in the medium temperature. However, since the aggregate are not intentionally moved, such case is also included in the static culture in the present invention. Static culture may be performed during the whole period of suspension culture, or only during a part of the period. For example, static culture may be performed in either one of the above-mentioned first culture step and second culture step. In a preferable embodiment, static culture may be performed during the whole period of suspension culture. Static culture requires no apparatus and is expected to cause less damage on the cell aggregate, and is advantageous since the amount of the culture medium can be small.

In a preferable embodiment, a qualitatively uniform population of pluripotent stem cell aggregates is cultured in suspension in a medium containing a Wnt signal inhibitor and a TGFβ signal inhibitor. Using a qualitatively uniform population of pluripotent stem cell aggregates, difference in levels of differentiation into telencephalon or a partial structure thereof, or a precursor tissue thereof between aggregates can be suppressed to the minimum, and the efficiency of the object differentiation induction can be improved. Suspension culture of a qualitatively uniform population of pluripotent stem cell aggregates encompasses the following embodiments.

(1) Plural culture compartments are prepared, and a qualitatively uniform population of pluripotent stem cell aggregates is seeded such that one pluripotent stem cell aggregate is contained in one culture compartment (e.g., one pluripotent stem cell aggregate is placed in each well of 96 well plate). In each culture compartment, one pluripotent stem cell aggregate is cultured in suspension in a medium containing Wnt signal inhibitor and TGFβ signal inhibitor.

(2) A qualitatively uniform population of pluripotent stem cell aggregates is seeded such that plural pluripotent stem cell aggregates are contained in one culture compartment (e.g., plural pluripotent stem cell aggregates are placed in a 10 cm dish). In the culture compartment, plural pluripotent stem cell aggregates are cultured in suspension in a medium containing Wnt signal inhibitor and TGFβ signal inhibitor.

Any of the embodiments (1) and (2) may be employed for the method of the present invention and the embodiment may be changed during culture (from embodiment (1) to embodiment (2), or from embodiment (2) to embodiment (1)). In one embodiment, the embodiment of (1) is employed in the first culture step and the embodiment of (2) is employed in the second culture step.

As mentioned above, since self-organization of the telencephalon is induced in a cell aggregate in the method of the present invention, the differentiation stage of telencephalon or a partial tissue thereof, or a precursor tissue thereof contained in the cell aggregate proceeds with the progress of time. Therefore, the culture period and culture conditions are preferably adjusted as appropriate according to the object telencephalon or a partial tissue thereof, or a precursor tissue thereof. In the following (4)-(11), one embodiment of the present invention is explained, which is an exemplification of the present invention and does not limit the present invention.

(4) Induction of Choroid Plexus

In the second culture step in the method of the present invention, suspension culture is performed in the presence of a Wnt signal enhancer and a bone morphogenetic factor signal transduction pathway activating substance, whereby choroid plexus or a progenitor tissue thereof can be induced in the cell aggregate.

The Wnt signal enhancer is not particularly limited as long as choroid plexus or a progenitor tissue thereof can be induced when used in the above-mentioned method. For example, GSK-3β inhibitor, recombinant Wnt3a, Wnt agonist (compound), Dkk (inhibitor of Wnt inhibitory protein), R-Spondin and the like can be mentioned. Examples of the GSK-3β inhibitor include CHIR99021 (6-[[2-[[4-(2,4-Dichlorophenyl)-5-(5-methyl-1H-imidazol-2-yl)-2-pyrimidinyl]amino]ethyl]amino]-3-pyridinecarbonitrile), Kenpaullone, 6-Bromoindirubin-3'-oxime (BIO) and the like. The Wnt signal enhancer is preferably a GSK-3β inhibitor, more preferably CHIR99021.

When used in the above-mentioned method, the concentration of the Wnt signal enhancer is not particularly limited as long as choroid plexus or a progenitor tissue thereof can be induced. When CHIR99021 is used, it is generally about 0.1 μM-30 μM, preferably about 1 μM-10 μM (e.g., 3 μM).

In the present specification, the bone morphogenetic factor signal transduction pathway activating substance is any substance that activates the pathway through which signals are transmitted upon binding of a bone morphogenetic factor and a receptor. Examples of the bone morphogenetic factor signal transduction pathway activating substance include BMP2, BMP4, BMP7, GDF5 and the like. Preferably, the bone morphogenetic factor signal transduction pathway activating substance is BMP4. While BMP4 is mainly described below, the bone morphogenetic factor signal transduction pathway activating substance to be used in the present invention is not limited to BMP4. BMP4 is a known cytokine, and the amino acid sequence thereof is also known. BMP4 to be used in the present invention is mammalian BMP4. Examples of the mammal include experiment animals such as rodents such as mouse, rat, hamster, guinea pig and the like, rabbit and the like; domestic animals such as swine, bovine, goat, horse, sheep and the like; companion animals such as dog, cat and the like; and primates such as human, monkey, orangutan, chimpanzee and the like. BMP4 is preferably BMP4 of rodents (mouse, rat etc.) or primates (human etc.), most preferably human BMP4. Human BMP4 means that BMP4 has the amino acid sequence of BMP4 naturally expressed in the human body. Examples of the representative amino acid sequence of human BMP4 include NCBI accession numbers NP_001193.2 (updated on Jun. 15, 2013), NP_570911.2 (updated on Jun. 15, 2013), NP_570912.2 (updated on Jun. 15, 2013), amino acid sequence (mature form human BMP4 amino acid sequence) obtained by removing the N-terminus signal sequence (1-24) from each of these amino acid sequences and the like.

The concentration of the bone morphogenetic factor signal transduction pathway activating substance in the medium can be appropriately determined within a range in which differentiation of pluripotent stem cells into choroid plexus or a precursor tissue thereof can be induced in the aggregate. When BMP4 is used as a bone morphogenetic factor signal transduction pathway activating substance, the concentration thereof is generally 0.05-10 nM, preferably 0.1-2.5 nM (e.g., 0.5 nM).

In a preferable embodiment, a medium to be used for the induction into choroid plexus or a progenitor tissue thereof may contain N2 supplement, Chemically Defined Lipid Concentrate, serum and heparin.

Culture in a medium containing a Wnt signal enhancer and a bone morphogenetic factor signal transduction pathway activating substance (BMP4 etc.) does not need to be performed throughout the period up to the induction into choroid plexus or a partial tissue thereof in the second culture step, and only need to be performed in a part of the period. For example, suspension culture in a medium containing a Wnt signal enhancer and a bone morphogenetic factor signal transduction pathway activating substance (BMP4 etc.) for not less than 3 days from the start of the second culture step is sufficient for inducing choroid plexus or a progenitor tissue thereof, and thereafter the suspension culture may be continued after changing the medium to one free of a Wnt signal enhancer and a bone morphogenetic factor signal transduction pathway activating substance (BMP4 etc.).

Here, selective differentiation into choroid plexus can be induced as the culture period in a medium containing a Wnt signal enhancer and a bone morphogenetic factor signal transduction pathway activating substance (BMP4 etc.) becomes longer (i.e., differentiation into telencephalon tissue other than choroid plexus (e.g., cerebral cortex, hippocampus) does not occur easily in the same cell aggregate). In one embodiment, choroid plexus or a progenitor tissue thereof can be induced in not less than 80% of the population of cell aggregates. On the other hand, when the culture period in a medium containing a Wnt signal enhancer and a bone morphogenetic factor signal transduction pathway activating substance (BMP4 etc.) is short, differentiation into a telencephalon tissue other than choroid plexus (e.g., cerebral cortex, hippocampus) easily occurs in the same cell aggregate, and cell aggregate containing choroid plexus or a progenitor tissue thereof, as well as cerebral cortex or a progenitor tissue thereof and/or hippocampus or a progenitor tissue thereof in the same cell aggregates can be obtained (described later).

Induction into the choroid plexus tissue can be confirmed using expression of a choroid plexus marker (e.g., TTR, Lmx1a, Otx2 etc.), non-expression of telencephalon marker (Foxg1 etc.), or morphology of ruffled monolayer epithelium as an index. The time necessary for the induction into the choroid plexus tissue varies depending on the culture conditions, and the kind of a mammal from which the pluripotent stem cells are derived, and cannot be generally specified. However, when human pluripotent stem cells are used, a choroid plexus tissue is induced inside the aggregates by, for example, day 24 from the start of the second culture step. By selecting a cell aggregate confirmed to have induced choroid plexus or a progenitor tissue thereof from the obtained plural cell aggregates, a cell aggregate containing choroid plexus or a progenitor tissue thereof can be obtained.

(5) Induction of Hippocampus

In the second culture step in the method of the present invention, suspension culture is performed in the presence of a Wnt signal enhancer, whereby hippocampus or a progenitor tissue thereof (cortical hem etc.) can be induced in cell aggregates.

The Wnt signal enhancer is not particularly limited as long as hippocampus or a progenitor tissue thereof can be induced when used in the above-mentioned method. For example, GSK-3β inhibitor, recombinant Wnt3a, Wnt agonist (compound), Dkk (inhibitor of Wnt inhibitory protein), R-Spondin and the like can be mentioned. Examples of the GSK-3β inhibitor include CHIR99021 (6-[[2-[[4-(2,4-Dichlorophenyl)-5-(5-methyl-1H-imidazol-2-yl)-2-pyrimidinyl]amino]ethyl]amino]-3-pyridinecarbonitrile), Kenpaullone, 6-Bromoindirubin-3'-oxime (BIO) and the like. The Wnt signal enhancer is preferably a GSK-3β inhibitor, more preferably CHIR99021.

When used in the above-mentioned method, the concentration of the Wnt signal enhancer is not particularly limited as long as hippocampus or a progenitor tissue thereof can be induced. When CHIR99021 is used, it is generally about 0.1 µM-30 µM, preferably about 1 µM-10 µM (e.g., 3 µM).

In a preferable embodiment, a medium to be used for the induction into hippocampus or a progenitor tissue thereof may contain N2 supplement, Chemically Defined Lipid Concentrate, serum and heparin.

Culture in a medium containing a Wnt signal enhancer does not need to be performed throughout the period up to the induction into hippocampus or a partial tissue thereof in the second culture step, and only need to be performed in a part of the period. For example, suspension culture in a medium containing a Wnt signal enhancer for not less than 3 days from the start of the second culture step is sufficient for inducing hippocampus or a progenitor tissue thereof, and thereafter the suspension culture may be continued after changing the medium to one free of a Wnt signal enhancer.

Here, selective differentiation into hippocampus can be induced as the culture period in a medium containing a Wnt signal enhancer becomes longer (i.e., differentiation into telencephalon tissue other than hippocampus (e.g., cerebral cortex, choroid plexus) does not occur easily in the same cell aggregate). In one embodiment, hippocampus or a progenitor tissue thereof can be induced in not less than 80% of the population of cell aggregates. On the other hand, when the culture period in a medium containing a Wnt signal enhancer is short, differentiation into a telencephalon tissue other than hippocampus (e.g., cerebral cortex, choroid plexus) easily occurs in the same cell aggregate, and cell aggregate containing hippocampal tissue or a progenitor tissue thereof, as well as cerebral cortex or a progenitor tissue thereof and/or choroid plexus or a progenitor tissue thereof in the same cell aggregate can be obtained.

In one embodiment, a medium used for induction into hippocampus or a progenitor tissue thereof does not contain a bone morphogenetic factor signal transduction pathway activating substance (BMP4 etc.). Using a medium free of a bone morphogenetic factor signal transduction pathway activating substance (BMP4 etc.), differentiation induction into choroid plexus is suppressed, and selective induction into a hippocampal tissue or a progenitor tissue thereof becomes possible.

In another embodiment, a medium used for induction into hippocampus or a progenitor tissue thereof may contain a bone morphogenetic factor signal transduction pathway activating substance (BMP4 etc.). In this case, hippocampus selectivity of differentiation decreases, whereas differentiation into telencephalon tissue other than hippocampus (e.g., choroid plexus) occurs easily in the same cell aggregate.

Induction of the hippocampus or a progenitor tissue thereof can be confirmed using expression of a cortical hem marker (Lmx1a, Otx2 etc.) and expression of a telencephalon marker (Foxg1 etc.) as an index. The time necessary for the induction into the hippocampus or a progenitor tissue thereof varies depending on the culture conditions, and the kind of a mammal from which the pluripotent stem cell is derived, and cannot be specified generally. However, when human pluripotent stem cells are used, hippocampus or a progenitor tissue thereof is induced inside the aggregate by, for example, day 24 from the start of the second culture step. By selecting a cell aggregate confirmed to have induced hippocampus or a progenitor tissue thereof from the obtained plural cell aggregates, a cell aggregate containing hippocampus or a progenitor tissue thereof can be obtained.

(6) Induction of Choroid Plexus, Hippocampal Progenitor Tissue and Cortical Progenitor Tissue In the second culture step of the method of the present invention, suspension culture is transiently performed in the presence of a Wnt signal enhancer and a bone morphogenetic factor signal transduction pathway activating substance, whereby choroid plexus (or a progenitor tissue thereof), hippocampus (or progenitor tissue) and cerebral cortex (or a progenitor tissue thereof) can be induced in one cell aggregate.

That is, in the second culture step, suspension culture is performed in the presence of a Wnt signal enhancer and a bone morphogenetic factor signal transduction pathway activating substance, and the obtained cell aggregate is further cultivated in the absence of a Wnt signal enhancer and a bone morphogenetic factor signal transduction pathway activating substance. As a result, choroid plexus (or a progenitor tissue thereof), a hippocampal tissue (or progenitor tissue) and a cerebral cortical tissue (or a progenitor tissue thereof) are formed in the continuous neuroepithelium contained in the obtained cell aggregate. In one embodiment, choroid plexus (or a progenitor tissue thereof), a hippocampal tissue (or progenitor tissue) and a cerebral cortical tissue (or a progenitor tissue thereof) can be induced in a continuous neuroepithelium in not less than 80% of the population of cell aggregates.

Although not bound by theory, a signal called organizer activity may flow due to a series of operation including formation of choroid plexus tissue by a treatment with a Wnt signal enhancer and a bone morphogenetic factor signal transduction pathway activating substance and elimination of these factors (promotion by addition, and rebound by elimination) (induction-reversal method), and appropriate self-organization of choroid plexus tissue, cortical hem, dentate gyrus tissue, and Ammon's horn tissue may be achieved.

The Wnt signal enhancer is not particularly limited as long as choroid plexus (or a progenitor tissue thereof), hippocampus (or progenitor tissue) and cerebral cortex (or a progenitor tissue thereof) can be induced in one cell aggregate when used in the above-mentioned method and, for example, GSK-3β inhibitor, recombinant Wnt3a, Wnt agonist (compound), Dkk (inhibitor of Wnt inhibitory protein), R-Spondin and the like can be mentioned. Examples of the GSK-3β inhibitor include CHIR99021, Kenpaullone, 6-Bromoindirubin-3'-oxime (BIO) and the like. The Wnt signal enhancer is preferably a GSK-3β inhibitor, more preferably CHIR99021.

The concentration of the Wnt signal enhancer is not particularly limited as long as choroid plexus (or a progenitor tissue thereof), hippocampus (or progenitor tissue) and cerebral cortical tissue (or a progenitor tissue thereof) can be induced in one cell aggregate when used in the above-mentioned method. When CHIR99021 is used, it is generally about 0.1 μM-100 μM, preferably about 1 μM-30 μM (e.g., 3 μM).

Examples of the bone morphogenetic factor signal transduction pathway activating substance include BMP2, BMP4, BMP7, GDF5 and the like. Preferably, the bone morphogenetic factor signal transduction pathway activating substance is BMP4.

The concentration of the bone morphogenetic factor signal transduction pathway activating substance in a medium is not particularly limited as long as choroid plexus (or a progenitor tissue thereof), hippocampus (or progenitor tissue) and cerebral cortex (or a progenitor tissue thereof) can be induced in one cell aggregate when used in the above-mentioned method. When BMP4 is used as a bone morphogenetic factor signal transduction pathway activating substance, the concentration thereof is generally 0.05-10 nM, preferably 0.1-2.5 nM (e.g., 0.5 nM).

In a preferable embodiment, a medium to be used in the second culture step in this methodology may contain N2 supplement, Chemically Defined Lipid Concentrate, serum and heparin.

Since the period of culture in a medium containing a Wnt signal enhancer and a bone morphogenetic factor signal transduction pathway activating substance (BMP4 etc.) varies depending on the culture conditions, and the kind of a mammal from which the pluripotent stem cells are derived, and cannot be generally specified. However, when human pluripotent stem cells are used, it is generally 1-7 days, preferably 2-4 days (e.g., 3 days).

Since the period of culture after removal of a Wnt signal enhancer and a bone morphogenetic factor signal transduction pathway activating substance (BMP4 etc.) varies depending on the culture conditions, and the kind of a mammal from which the pluripotent stem cells are derived, and cannot be generally specified. However, when human pluripotent stem cells are used, it is generally not less than 10 days, preferably not less than 14 days.

Continuous formation of choroid plexus (or a progenitor tissue thereof), hippocampus (or progenitor tissue) and a cerebral cortical tissue (or a progenitor tissue thereof) in one cell aggregate can be confirmed using the expression of markers for each tissue as an index. For example, Lmx1a-positive and Foxg1-negative choroid plexus region, Foxg1-weakly positive cortical hem region expressing Lmx1a and Otx2, Lef1-positive and Foxg1-positive hippocampal progenitor tissue region, and Lef1-negative and Foxg1-positive cortical progenitor tissue are continuously formed on the same neuroepithelium in a mutually-adjacent configuration similar to that in vivo.

By selecting, from the obtained population of cell aggregates, a cell aggregate wherein choroid plexus (or a progenitor tissue thereof), hippocampus (or progenitor tissue) and cerebral cortex (or a progenitor tissue thereof) are formed in a continuous neuroepithelium, the object cell aggregate can be obtained.

(7) Continuous Three Dimensional Formation of Each Region in Hippocampal Tissue

Similar to (6), in the second culture step of the method of the present invention, suspension culture is transiently performed in the presence of a Wnt signal enhancer and a bone morphogenetic factor signal transduction pathway activating substance, whereby a hippocampal tissue or a progenitor tissue thereof continuously containing a dentate gyrus tissue (or a progenitor tissue thereof) and an Ammon's horn tissue (or a progenitor tissue thereof) in one cell aggregate can be induced. Differentiation of an Ammon's horn tissue (or a progenitor tissue thereof) from pluripotent stem cells has not been reported heretofore.

That is, in the second culture step, suspension culture is performed in the presence of a Wnt signal enhancer and a bone morphogenetic factor signal transduction pathway activating substance, and the obtained cell aggregate is further cultured under a high oxygen partial pressure condition in the absence of a Wnt signal enhancer and a bone morphogenetic factor signal transduction pathway activating substance. As a result, a hippocampal tissue or a progenitor tissue thereof containing a dentate gyrus tissue (or a progenitor tissue thereof) and an Ammon's horn tissue (or a progenitor tissue thereof) is formed in the continuous neuroepithelium in the obtained cell aggregate. In addition, as a result of the culture, a cell aggregate containing an Ammon's horn tissue (or a progenitor tissue thereof) can be obtained.

Although not bound by theory, a signal called organizer activity may flow due to a series of operation including formation of choroid plexus tissue by a treatment with a Wnt signal enhancer and a bone morphogenetic factor signal transduction pathway activating substance and elimination of these factors (promotion by addition, and rebound by elimination) (induction-reversal method), and appropriate self-organization of choroid plexus tissue, cortical hem, dentate gyrus tissue, and Ammon's horn tissue may be achieved.

The Wnt signal enhancer is not particularly limited as long as a dentate gyrus tissue (or a progenitor tissue thereof) and an Ammon's horn tissue (or a progenitor tissue thereof) can be induced in one cell aggregate when used in the above-mentioned method and, for example, GSK-3β inhibitor, recombinant Wnt3a, Wnt agonist (compound), Dkk (inhibitor of Wnt inhibitory protein), R-Spondin and the like can be mentioned. Examples of the GSK-3β inhibitor include CHIR99021, Kenpaullone, 6-Bromoindirubin-3'-oxime (BIO) and the like. The Wnt signal enhancer is preferably a GSK-3β inhibitor, more preferably CHIR99021.

The concentration of the Wnt signal enhancer is not particularly limited as long as a dentate gyrus tissue (or a progenitor tissue thereof) and an Ammon's horn tissue (or a progenitor tissue thereof) can be induced in one cell aggregate when used in the above-mentioned method. When CHIR99021 is used, it is generally about 0.1 μM-30 μM, preferably about 1 μM-10 μM (e.g., 3 μM).

Examples of the bone morphogenetic factor signal transduction pathway activating substance include BMP2, BMP4, BMP7, GDF5 and the like. Preferably, the bone morphogenetic factor signal transduction pathway activating substance is BMP4.

The concentration of the bone morphogenetic factor signal transduction pathway activating substance in a medium is not particularly limited as long as a dentate gyrus tissue (or a progenitor tissue thereof) and an Ammon's horn tissue (or a progenitor tissue thereof) can be induced in one cell aggregate when used in the above-mentioned method. When BMP4 is used as a bone morphogenetic factor signal transduction pathway activating substance, the concentration thereof is generally 0.05-10 nM, preferably 0.1-2.5 nM (e.g., 0.5 nM).

In a preferable embodiment, a medium to be used in the second culture step in this methodology may contain N2 supplement, Chemically Defined Lipid Concentrate, serum and heparin.

In another preferable embodiment, a medium to be used in the second culture step in this methodology may contain B27 supplement, L-glutamine and serum.

Since the period of culture in a medium containing a Wnt signal enhancer and a bone morphogenetic factor signal transduction pathway activating substance (BMP4 etc.) varies depending on the culture conditions, and the kind of a mammal from which the pluripotent stem cells are derived, and cannot be generally specified. However, when human pluripotent stem cells are used, it is generally 1-7 days, preferably 2-4 days (e.g., 3 days).

Since the period of culture after removal of a Wnt signal enhancer and a bone morphogenetic factor signal transduction pathway activating substance (BMP4 etc.) varies depending on the culture conditions, and the kind of a mammal from which the pluripotent stem cells are derived, and cannot be generally specified. However, when human pluripotent stem cells are used, it is generally not less than 40 days, preferably not less than 51 days.

Continuous formation of a dentate gyrus tissue (or a progenitor tissue thereof) and an Ammon's horn tissue (or a progenitor tissue thereof) in one cell aggregate can be confirmed using the expression of markers for each tissue as an index. For example, the dentate gyrus tissue (or a progenitor tissue thereof) can be specified by being Lef1 (hippocampal progenitor tissue marker) positive, Zbtb20 positive, Prox1 positive and the like. Ammon's horn (or a progenitor tissue thereof) can be specified by being Lef1 (hippocampal progenitor tissue marker) positive, Zbtb20 weakly positive and the like.

In one embodiment, a cell aggregate obtained by the present invention further contains, in addition to a dentate gyrus tissue (or a progenitor tissue thereof) and an Ammon's horn tissue (or a progenitor tissue thereof), cortical hem in the continuous neuroepithelium in the cell aggregate. That is, a hippocampal tissue or a progenitor tissue thereof containing a dentate gyrus tissue (or a progenitor tissue thereof), an Ammon's horn tissue (or a progenitor tissue thereof) and cortical hem can be induced in the continuous neuroepithelium.

In one embodiment, a cell aggregate obtained by the present method shows an expression intensity gradient in which the expression of Zbtb20 is stronger in a part (dentate gyrus tissue or a progenitor tissue thereof) adjacent to the region of the choroid plexus (Lmx1a positive, Foxg1 negative) or cortical hem (Lmx1a positive, Foxg1 weakly positive) and becomes weaker as the part gets farther therefrom in the Lef1 positive neuroepithelium.

In another embodiment, a dentate gyrus tissue or a progenitor tissue thereof (e.g., Zbtb20-positive, Prox1-positive) are formed between an Ammon's horn tissue or a progenitor tissue thereof (e.g., Zbtb20-weakly positive), and cortical hem and choroid plexus. That is, a dentate gyrus tissue (or a progenitor tissue thereof), an Ammon's horn tissue (or a progenitor tissue thereof) and cortical hem are continuously formed in the neuroepithelium in a mutually-adjacent position similar to that in vivo.

By selecting, from the obtained population of cell aggregates, a cell aggregate wherein a dentate gyrus tissue (or a progenitor tissue thereof) and an Ammon's horn tissue (or a progenitor tissue thereof) are formed in a continuous neuroepithelium, the object cell aggregate can be obtained.

(8) Induction of Basal Ganglion Tissue

In the method of the present invention, a cell aggregate is treated with a sonic hedgehog (Shh) signal agonist, whereby basal ganglion or a progenitor tissue thereof can be induced in the cell aggregate.

The Shh signal agonist is not particularly limited as long as a basal ganglion tissue or a progenitor tissue thereof can be induced when used in the above-mentioned method. For example, proteins belonging to the Hedgehog family (e.g., Shh), Shh receptor agonist, Purmorphamine, SAG (N-Methyl-N'-(3-pyridinylbenzyl)-N'-(3-chlorobenzo[b]thiophene-2-carbonyl)-1,4-diaminocyclohexane) and the like can be mentioned. The Shh signal agonist is preferably SAG.

The concentration of the Shh signal agonist is not particularly limited as long as a basal ganglion tissue or a progenitor tissue thereof can be induced when used in the above-mentioned method. When SAG is used, it is generally 1 nM-10 μM.

When SAG is used at a comparatively low concentration (e.g., 1 nM-75 nM, preferably 25 nM-50 nM), lateral ganglionic eminence (LGE) of the basal ganglion is preferentially induced on the telencephalon neuroepithelium. On the other hand, when SAG is used at a comparatively high concentration (e.g., 100 nM-10 μM, preferably 250 nM-1 μM), medial ganglionic eminence (MGE) of the basal ganglion is preferentially induced on the telencephalon neuroepithelium.

A cell aggregate to be subjected to the Shh signal agonist treatment is preferably a telencephalon marker-positive cell aggregate. The Shh signal agonist treatment (culture in a medium containing a Shh signal agonist) may be performed in only one or both of the first culture step and the second culture step. Culture in a medium containing a Shh signal agonist may be performed over the whole period until the basal ganglion tissue is induced, or only in a part of the period.

In one embodiment, the Shh signal agonist treatment is transiently performed for 3-10 days (e.g., 7 days) from the latter stage of the first culture step to the earlier stage of the second culture step, where a telencephalon marker is expressed in cell aggregates.

Induction of basal ganglion or a progenitor tissue thereof can be confirmed using expression of a basal ganglion tissue marker as an index. As the lateral ganglionic eminence (LGE) marker, Gsh2 and GAD65 can be mentioned. As the medial ganglionic eminence (MGE) marker, Nkx2.1 can be mentioned.

The time necessary for induction of basal ganglion or a progenitor tissue thereof varies depending on the culture conditions, and the kind of a mammal from which the pluripotent stem cells are derived, and cannot be generally specified. However, when human pluripotent stem cells are used, basal ganglion or a progenitor tissue thereof is induced inside the aggregate by, for example, 24 days from the start of the second culture step. In one embodiment, basal ganglion or a progenitor tissue thereof can be induced in not less than 70% of the population of cell aggregates. By selecting a cell aggregate confirmed to have induced basal ganglion or a progenitor tissue thereof from the obtained plural cell aggregates, a cell aggregate containing basal ganglion or a progenitor tissue thereof can be obtained.

In a preferable embodiment, basal ganglion (or a progenitor tissue thereof) (e.g., LGE, MGE) induced by the present method is continuously formed with cerebral cortex (or a progenitor tissue thereof) in one cell aggregate. That is, basal ganglion (or a progenitor tissue thereof) (e.g., LGE, MGE) and cerebral cortex (or a progenitor tissue thereof) are formed in the continuous neuroepithelium contained in the obtained cell aggregate. In one embodiment, basal ganglion (or a progenitor tissue thereof) (e.g., LGE, MGE) and cerebral cortex (or a progenitor tissue thereof) can be induced in a continuous neuroepithelium in not less than 50% of the population of cell aggregates.

(9) Exogenous Regulation of Axis Formation in Cerebral Cortex

As mentioned above, in the method of the present invention, the dorsal-ventral and anterior-posterior axes of the cerebral cortex are spontaneously formed. In one embodiment, in the cortical ventricular zone contained in the cell aggregate obtained in the second culture step, expression of the dorsocaudal marker (CoupTF1, Lhx2 etc.) shows a gradient of being stronger on one side and weaker on the opposite side and the expression of the rostral marker (e.g., Sp8) shows a reverse gradient pattern from that of the dorsocaudal marker. By reacted with FGF8 known to be important for acquiring rostral specificity of the cerebral cortex, the whole cerebral cortex ventricular zone can be rostralized.

The FGF8 treatment can be performed by using a medium containing FGF8 in the second culture step. The concentration of FGF in the medium is a concentration sufficient for rostralization, and is generally 10-1000 ng/ml, preferably 50-300 ng/ml.

The FGF8 treatment is performed in the whole or a part of the second culture step.

Rostralization of the whole cerebral cortex ventricular zone can be confirmed based on overall attenuation of expression of a dorsocaudal marker (CoupTF1, Lhx2 etc.), an overall increase of a rostral marker (e.g., Sp8) over the whole ventricular zone and the like. This indicates a possibility that a region of frontal lobe, occipital lobe and the like along the dorsal-ventral axis of the cerebral cortex can be selectively controlled and induced by a FGF8 treatment.

(10) Induction of Hippocampal Neuron

A cell aggregate containing hippocampus or a progenitor tissue thereof obtained by the method of any of the above-mentioned (5)-(7) is dispersed, and the dispersed cells are further subjected to adhesion culture in vitro, whereby mature hippocampal neuron can be obtained. The present invention also provides such production method of hippocampal neuron.

In the production method, a cell aggregate containing hippocampus or a progenitor tissue thereof obtained by the method of the above-mentioned (7) (a cell aggregate containing a hippocampal tissue or a progenitor tissue thereof containing a dentate gyrus tissue (or a progenitor tissue thereof) and an Ammon's horn tissue (or a progenitor tissue thereof) continuously) is preferably used.

A cell aggregate containing hippocampus or a progenitor tissue thereof is treated with an appropriate cell dissociation solution, and dispersed to a single cell state or near single cell state. Examples of the cell dissociation solution include physiological aqueous solution containing chelate such as EDTA etc.; protease such as papain, trypsin, collagenase IV, metalloproteinase and the like, and the like, which are used alone or in an appropriate combination.

The dispersed cells are suspended in an appropriate medium for culturing the cells and seeded in a culture vessel. As a culture vessel, an adhesive culture vessels generally used for adhesion culture of cells can be used. Examples of the culture vessel include, but are not limited to, schale, petri dish, flask, multi-well plate, chamber slide and the like.

To improve adhesiveness to the cells, a surface of a culture vessel may be coated with an extracellular matrix such as laminin, fibronectin, collagen, basement membrane preparation and the like; or a polymer such as poly-L-lysine, poly-D-lysine, poly-L-ornithine and the like. In one embodiment, a surface of a culture vessel is directly or indirectly coated with laminin and fibronectin. Indirect coating can be performed by, for example, first coating a surface of a culture vessel with poly-L-lysine to form an undercoat of poly-L-lysine, and applying laminin and fibronectin on the undercoat.

The medium to be used for adhesion culture of dispersed cells can be prepared using a medium used for culturing animal cells (preferably neuron) as a basal medium. The basal medium is not particularly limited as long as it can be used for culture of animal cells (preferably neuron) and may be DMEM, Ham's F-12, Neurobasal, IMDM, M199, EMEM, αMEM, Fischer's Medium, mixed medium of these and the like. Preferably, Neurobasal is used.

To promote maturation of hippocampal neuron, the medium preferably contains B27 supplement as a serum replacement. B27 supplement is a known composition including biotin, L-carnitine, corticosterone, ethanolamine, D(+)galactose, reduced glutathione, linoleic acid, linolenic acid, progesterone, putrescine, retinyl acetate, selenium, triiodo-l-thyronine, vitamin E, vitamin E acetate, bovine albumin, catalase, insulin, superoxide dismutase, transferrin and the like. To avoid inhibition of maturation of the hippocampal neuron, use of a vitamin A-free B27 supplement which is said composition excluding retinyl acetate is preferable. The amount of the B27 supplement to be added is appropriately determined in such a manner as promotes maturation of hippocampal neuron.

In one embodiment, to promote maturation of hippocampal neuron, the medium may contain BDNF. When BDNF is contained, the concentration of BDNF in the medium is not particularly limited as long as maturation of hippocampal neuron is promoted. It is generally not less than 1 ng/ml, preferably not less than 10 ng/ml, more preferably not less than 20 ng/ml. The upper limit of the BDNF concentration is not particularly limited as long as maturation of hippocampal neuron is promoted. Since the activity is saturated even when BDNF is added in excess, the concentration is generally not more than 1000 ng/ml, preferably not more than 100 ng/ml. BDNF is preferably isolated.

In one embodiment, to promote maturation of hippocampal neuron, the medium may contain NT-3. When NT-3 is contained, the concentration of NT-3 in the medium is not particularly limited as long as maturation of hippocampal neuron is promoted. It is generally not less than 1 ng/ml, preferably not less than 10 ng/ml, more preferably not less than 20 ng/ml. The upper limit of the NT-3 concentration is not particularly limited as long as maturation of hippocampal neuron is promoted. Since the activity is saturated even when NT-3 is added in excess, the concentration is generally not more than 1000 ng/ml, preferably not more than 100 ng/ml. NT-3 is preferably isolated.

In one embodiment, the medium may contain a serum. The serum may contribute to the maturation of hippocampal neuron. Examples of the serum include, but are not limited to, FBS and the like. The serum is preferably inactivated. The concentration of the serum in the medium can be appropriately adjusted within the range in which it can contribute to the maturation culture of the ventricular zone for a long term. It is generally 1-20% (v/v).

In one embodiment, the medium may contain other additive as long as an adverse influence is not exerted on the maturation of hippocampal neuron. Examples of the additive include, but are not limited to, insulin, iron source (e.g., transferrin etc.), mineral (e.g., sodium selenate etc.), saccharides (e.g., glucose etc.), organic acid (e.g., pyruvic acid, lactic acid etc.), serum protein (e.g., albumin etc.), amino acid (e.g., L-glutamine etc.), reducing agent (e.g., 2-mercaptoethanol etc.), vitamins (e.g., ascorbic acid, d-biotin etc.), antibiotic (e.g., streptomycin, penicillin, gentamicin etc.), buffering agent (e.g., HEPES etc.) and the like.

In a preferable embodiment, a medium to be used for the adhesion culture of the dispersed cells contains B27 supplement. The B27 supplement is preferably vitamin A-free. The medium may further contain FBS and L-glutamine.

In another preferable embodiment, a medium to be used for the adhesion culture of the dispersed cells contains B27 supplement, BDNF and NT-3. The B27 supplement is preferably vitamin A-free. The medium may further contain FBS and L-glutamine.

To suppress cell death of the dispersed cells, an inhibitor of Rho-associated coiled-coil kinase (ROCK) may by added from the start of adhesion culture. A ROCK inhibitor is added, for example, within 15 days, preferably within 10 days, more preferably within 6 days, from the start of culture. Examples of the ROCK inhibitor include Y-27632 ((+)-(R)-trans-4-(1-aminoethyl)-N-(4-pyridyl)cyclohexanecarboxamide dihydrochloride) and the like. The concentration of the ROCK inhibitor used for adhesion culture is a concentration capable of suppressing cell death. For example, for Y-27632, this concentration is normally about 0.1 to 200 μM, preferably about 2 to 50 μM. The concentration of the ROCK inhibitor may be varied within the period of addition. For example, the concentration can be reduced to half in the latter stage of the period.

Other culturing conditions of dispersed cells in adhesion culture, such as culturing temperature, $CO_2$ concentration and the like, can be set as appropriate. The culturing temperature is not particularly limited, and is, for example, about 30 to 40° C., preferably about 37° C. The $CO_2$ concentration is, for example, about 1 to 10%, preferably about 5%.

Within 2-3 days from the start of the adhesion culture, the seeded cells adhere to a surface of the culture vessel, and start to extend neurites.

While the period of adhesion culture of the dispersed cells is not particularly limited as long as it is sufficient for differentiation of the dispersed cells into mature hippocampal neuron, it is generally not less than 50 days, preferably not less than 80 days, more preferably not less than 100 days.

In one embodiment, adhesion culture of the dispersed cells is performed until mature hippocampal neuron emerges. Emergence of mature hippocampal neuron can be confirmed by a hippocampal neuron-specific marker. Mature hippocampal neuron is, for example, Zbtb20 and Foxg1 positive, and can be specified as a cell having a MAP2 positive dendrite. Therefore, in one embodiment, adhesion culture of the dispersed cells is performed until emergence of a cell which is Zbtb20- and Foxg1-positive and has a MAP2 positive dendrite is confirmed.

The above-mentioned mature hippocampal neuron encompasses hippocampus dentate granule cells (Prox1 positive, comparatively small cells having a circular shape), and hippocampus CA3 region pyramidal cells (KA1 positive, comparatively large cell).

In addition to hippocampal neuron, Zbtb20 and GFAP positive astrocytes may be induced. The present invention also provides a production method of the astrocyte.

Singly dispersed cells easily form small masses, and neurites are elongated among induced mature hippocampal neurons.

The thus-induced mature hippocampal neuron is functional, and causes sodium and potassium electric current responses, induced action potential, and/or spontaneous excitatory postsynaptic current (sEPSC) due to electric potential stimulation. These neural activities can be confirmed using the Patch clamp technique.

The induced mature hippocampal neuron can also be directly used for functional analysis and the like, or can be detached and isolated from a culture vessel by using an appropriate cell dissociation solution.

(11) Use of Cell Aggregate, Isolated Telencephalon or a Partial Tissue Thereof, or a Progenitor Tissue Thereof In a further aspect, telencephalon or a partial tissue thereof, or a progenitor tissue thereof can be isolated from a cell aggregate obtained as mentioned above. The present invention provides a cell aggregate, telencephalon or a partial tissue thereof, and a progenitor tissue thereof obtained by the above-mentioned method of the present invention. In a further embodiment, the present invention provides a hippocampal neuron obtained by the above-mentioned method of the present invention.

The cell aggregate, telencephalon or a partial tissue thereof, progenitor tissues thereof, and hippocampal neuron obtained by the present invention can be used for transplantation therapy. For example, cell aggregate, telencephalon or a partial tissue thereof (cerebral cortex, basal ganglion, choroid plexus, hippocampus etc.), progenitor tissues thereof, or hippocampal neuron obtained by the present invention can be used as a therapeutic drug for diseases resulting from the disorders of telencephalon (cerebral cortex, basal ganglion, choroid plexus, hippocampus etc.), or for complementing the corresponding damaged parts in the damaged condition of telencephalon (cerebral cortex, basal ganglion, choroid plexus, hippocampus etc.). By transplanting cell aggregate, telencephalon or a partial tissue thereof (cerebral cortex, basal ganglion, choroid plexus, hippocampus etc.), or a precursor tissue thereof or hippocampal neuron obtained by the present invention to patients with diseases resulting from the disorders of telencephalon or damaged telencephalon, the diseases resulting from the disorders of telencephalon or damage in the telencephalon can be treated. As the diseases resulting from the disorders of telencephalon, Parkinson's disease, Huntington chorea, Alzheimer's disease, ischemic brain diseases (e.g., cerebral apoplexy), epilepsy, brain trauma, motor neuron disease, neurodegenerative disease and the like can be mentioned. As the conditions in request for supplementation of these cells, those after neurosurgical procedure (e.g., after brain tumor extirpation) can be mentioned.

In transplantation therapy, graft rejection due to the difference in the histocompatibility antigen is often problematic, which problem, however, can be solved by using a pluripotent stem cell (e.g., induced pluripotent stem cell) established from the somatic cell of the transplantation recipient. That is, in a preferable embodiment, a pluripotent stem cell (e.g., induced pluripotent stem cell) established from the somatic cell of the recipient is used as a pluripotent stem cell in the method of the present invention, and telencephalon or a partial tissue thereof, or a precursor tissue thereof, or hippocampal neuron which is immunologically self for the recipient, is produced and transplanted to the recipient.

Furthermore, cell aggregate, telencephalon or a partial tissue thereof, or a precursor tissue thereof, or hippocampal neuron, which is obtained by the present invention, can be used for screening and evaluation of drugs. Particularly, since telencephalon or a partial tissue thereof, or a precursor tissue thereof, which is obtained by the present invention, has a higher structure extremely similar to that of telencephalon or a partial tissue or a precursor tissue thereof in vivo, it can be applied to screening for a therapeutic drug for diseases resulting from disorders of telencephalon, and damaged telencephalon, side effects and toxicity tests (e.g., substituting test of cornea stimulation test) of pharmaceutical products, and the development of a new therapeutic method for diseases of telencephalon and the like.

The present invention is explained in more detail in the following by referring to the following Examples, which are mere exemplifications and do not limit the scope of the present invention.

EXAMPLES

Example 1

Selective Three Dimensional Formation of Cortical Progenitor Tissue from Human Pluripotent Stem Cells
(Method)

Human ES cells (KhES-1; a fluorescence protein gene Venus is knocked-in a telencephalon specific gene Foxg1) were dispersed to single cells by a trypsin treatment, and according to the SFEBq method (Nakano et al, Cell Stem Cell, 2012), aggregates were formed and subjected to suspension aggregate culture at 37° C. in the presence of 5% $CO_2$ for differentiation induction. The dispersed 9000 human ES cells were seeded in each well of a V bottom 96 well plate applied with a low cell adsorptive surface coating, and a growth factor-free G-MEM medium (Gibco/Invitrogen) added with 20% KSR (Knockout Serum Replacement), 0.1 mM non-essential amino acid solution (Gibco/Invitrogen), 1 mM sodium pyruvate solution (Sigma), and 0.1 mM 2-mercaptoethanol was used as the medium for differentiation induction. To suppress dispersion-induced cell death, 20 µM of a ROCK inhibitor Y-27632 was added for the first 3 days of differentiation induction, and the concentration thereof was reduced to half for the next 3 days. From day 0 to day 18 after the start of the differentiation induction, Wnt signal inhibitor IWR-1-end (3 µM) and TGFβ signal inhibitor SB431542 (5 µM) were added and allowed to react. On day 18 from the start of differentiation induction, these aggregates were transferred to a 9 cm petri dish applied with low cell-adhesive surface coating, and suspension culture was performed at 37° C., in the presence of 5% $CO_2$, 40% $O_2$. From day 18 to day 35, DMEM/F12 medium (Gibco/Invitrogen) added with 1% N2 supplement (Gibco/Invitrogen), and 1% lipid concentrate (Chemically defined lipid concentrate, Gibco/Invitrogen) was used. From day 35, the medium further added with 10% FBS, 5 µg/ml heparin, and 1% Matrigel growth factor reduced (BD Bioscience) was used. The aggregate was analyzed on day 1 and day 34 from the start of differentiation induction, and analyzed by immunohistostaining on day 42.
(Results)

From after 18 days from the start of the differentiation induction, strong fluorescence of Foxg1::venus was observed in the aggregate. After 26 days from the start of the differentiation induction, strong fluorescence of Foxg1::venus was observed with good reproducibility in not less than 90% of the aggregates (FIG. 1A). After 34 days from the start of the differentiation induction, fluorescence of Foxg1::venus was observed in 75% of the total cells. The all aggregates were Foxg1::venus positive (FIG. 1B). The Foxg1::venus positive aggregate contained semispherical neuroepithelium-like structure (pseudostratified columnar epithelial) with a ventricle-like cavity inside. The neuroepithelial structure had a high cell-dense cell layer positive for Pax6 and Sox2 on the luminal side (FIGS. 1D and E), whereas phosphorylated Histon H3 positive cells under mitosis were found in its innermost part (FIG. 1F). These structures were similar to cortical ventricular zone in early trimester. Outside of the ventricular zone-like cell layer expressed a post-mitotic neuron marker Tuj1 and early cortical plate markers Ctip2 and Tbr1. They contained Reelin-positive Cajal-Retzius cells, which are neurons in the layer I of the cerebral cortex, and a Laminin-rich layer near the surface. Thus, it was clarified that a cortical progenitor tissue was formed in the cultured aggregate. Such self-organization of a cortical progenitor tissue in human early trimester was observed with good reproducibility.

Example 2

Three Dimensional Formation of Basal Ganglia Progenitor Tissue from Human Pluripotent Stem Cells
(Method)

Up to day 35 of differentiation induction, cells were cultured under culture conditions similar to those of Example 1. That is, human ES cell aggregates were cultured in a V bottom 96 well plate up to 18 days after differentiation induction, suspended aggregates were transferred to a non-cell adhesive petri dish (diameter 6 cm), and suspension culture was performed at 37° C. in the presence of 5% $CO_2$, 40% $O_2$ from day 18 to day 35 of differentiation induction. However, Sonic hedgehog (Shh) signal agonist SAG was added to the culture medium of Example 1 at a final concentration of 30 nM or 500 nM only in the period of from day 15 to day 21 and allowed to react. The aggregate was analyzed by immunohistostaining on day 35.
(Results)

Figure 2:
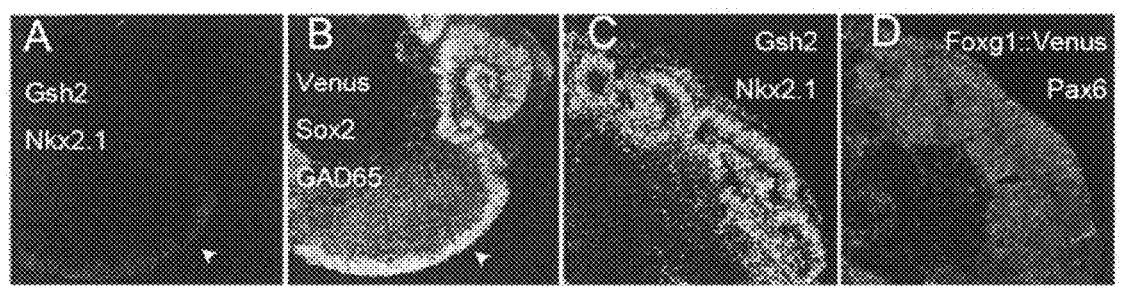
FIG. 2 shows induction of differentiation of human pluripotent stem cells into basal ganglia progenitor tissues. (A) LGE expressing Gsh2 formed in telencephalon neuroepithelium. (B) GAD65 positive GABAergic neurons present underneath LGE neuroepithelium. (C) MGE expressing Nkx2.1 formed in telencephalon neuroepithelium. (D) Pax6 expression in cell aggregates forming MGE.

When 30 nM Shh signal agonist SAG was reacted, lateral ganglionic eminence (LGE) expressing Gsh2 was formed in the Foxg1::venus positive telencephalon neuroepithelium (arrow heads in FIG. 2A, B). Gsh2 positive LGE neuroepithelium was observed with good reproducibility under these conditions in not less than 70% of the aggregates. Fetal LGE produces striatal neuron which is a GABAergic neuron. Similarly, GAD65 positive GABAergic neurons were observed beneath LGE neuroepithelium derived from human ES cells (FIG. 2B).

On the other hand, when 500 nM of Shh signal agonist SAG was reacted, Foxg1::venus positive telencephalon neuroepithelium in the aggregate formed medial ganglionic eminence (MGE) expressing Nkx2.1 (FIG. 2C, D). Foxg1::venus positive and Nkx2.1 positive MGE neuroepithelium was observed with good reproducibility under these conditions in not less than 80% of the aggregates. In fetal brain, MGE is a progenitor tissue of pallidum and cortical interneuron. It was shown that the present culture method can highly efficiently induce basal ganglia progenitor tissues LGE and MGE.

Example 3

Continuous Three Dimensional Formation of Cerebral Cortex and Basal Ganglion
(Method)

Up to day 35 of differentiation induction, cells were cultured under culture conditions similar to those of Example 2. That is, human ES cell aggregates were cultured in a V bottom 96 well plate up to 18 days after differentiation induction, suspended aggregates were transferred to a non-cell adhesive petri dish (diameter 9 cm), and suspension culture was performed at 37° C. in the presence of 5% $CO_2$, 40% $O_2$, from day 18 to day 35 of differentiation induction. However, Shh signal agonist SAG was added to the culture medium at a concentration of 30 nM only in the period of from day 15 to day 21 of differentiation induction. The aggregate was analyzed by immunohistostaining on day 35.
(Results)

Figure 3:
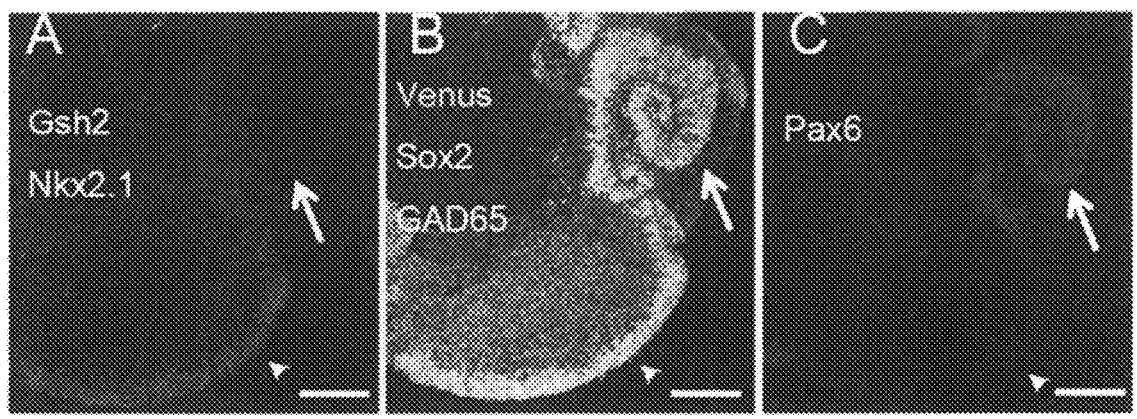
FIG. 3 shows continuous three dimensional formation of cerebral cortex and basal ganglion. (A) LGE expressing Gsh2 formed in telencephalon neuroepithelium. (B) GAD65 expression in LGE formed in telencephalon neuroepithelium. (C) Pax positive cortical neuroepithelium continuously formed with LGE neuroepithelium.

As shown in Example 2, when 30 nM Shh signal agonist SAG was reacted, the telencephalon neuroepithelium was Foxg1::venus positive, and expressed lateral ganglionic eminence (LGE) markers Gsh2, GAD65 (FIG. 3A, B). The LGE neuroepithelium was continuously formed with Gsh2 negative, cerebral cortex marker Pax6-positive cortical neuroepithelium (FIG. 3C). These results show that cerebral cortex and basal ganglion are continuously formed in one aggregate. Such continuous self-formation of cerebral cortex and basal ganglion in one aggregate was observed with good reproducibility in not less than 50% of the aggregates.

Example 4

Selective Three Dimensional Formation of Choroid Plexus Tissue from Human Pluripotent Stem Cells
(Method)

After culture in a V bottom 96 well plate under culture conditions of Example 1 up to 18 days after differentiation induction, suspended aggregates were transferred to a non-cell adhesive petri dish (diameter 9 cm), and suspension culture was performed at 37° C. in the presence of 5% $CO_2$, 40% $O_2$. The culture medium used for the culture was DMEM/F12 medium (Gibco/Invitrogen) added with 1% N2 supplement (Gibco/Invitrogen), 1% lipid concentrate (Chemically defined lipid concentrate, Gibco/Invitrogen), 10% FBS, 5 μg/ml heparin, 3 μM GSK-3β inhibitor CHIR99021, and 0.5 nM BMP4 from day 18 to day 42, and the aggregates were analyzed by immunohistostaining on day 42.
(Results)

Figure 4:
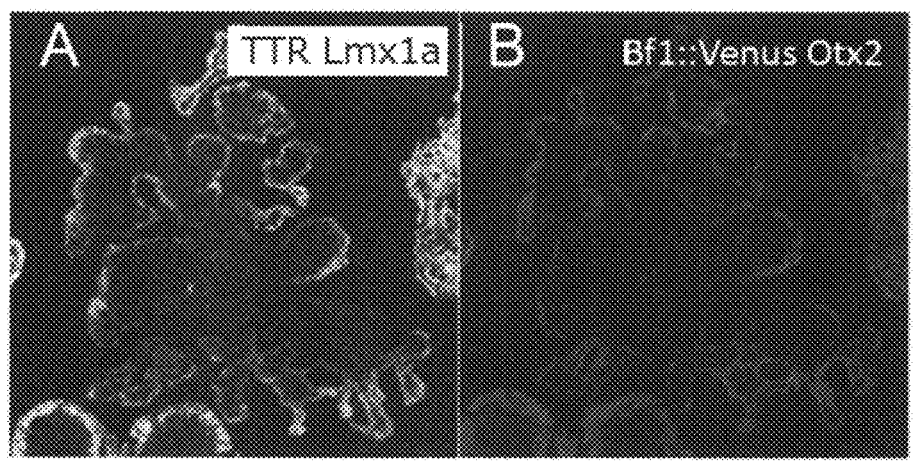
FIG. 4 shows differentiation induction of human from pluripotent stem cells into choroid plexus tissue. (A) TTR and Lmx1a expression in choroid plexus tissue induced from pluripotent stem cells. (B) Otx2 expression in choroid plexus tissue induced from pluripotent stem cells. Expression of Foxg1::venus is not observed.

When cultured under the above-mentioned conditions, strong fluorescence of Bf1(Foxg1)::venus was not observed in the aggregate even after day 18 from the start of differentiation induction. Since these aggregates formed a ruffled monolayer epithelium and expressed choroid plexus markers TTR, Lmx1a, Otx2 (FIG. 4A, B), a choroid plexus tissue was considered to have been induced. Self-formation of choroid plexus tissue under these conditions was observed with good reproducibility in not less than 80% of the aggregates.

Example 5

Selective Formation of Cortical Hem (Fimbrial Progenitor Tissue) from Human Pluripotent Stem Cells
(Method)

Cell aggregates were cultured in a V bottom 96 well plate under culture conditions of Example 1 up to day 18 of differentiation induction, then suspended aggregates were transferred to a non-cell adhesive petri dish (diameter 9 cm), and suspension culture was performed at 37° C. in the presence of 5% $CO_2$, 40% $O_2$. The culture medium used for the culture from day 18 to day 42 was DMEM/F12 medium (Gibco/Invitrogen) added with 1% N2 supplement (Gibco/Invitrogen), 1% lipid concentrate (Chemically defined lipid concentrate, Gibco/Invitrogen), 10% FBS, 5 μg/ml heparin, 3 μM GSK-3β inhibitor CHIR99021 (Wnt signal enhancer) and the aggregates were analyzed by immunohistostaining on day 42.
(Results)

Figure 5:
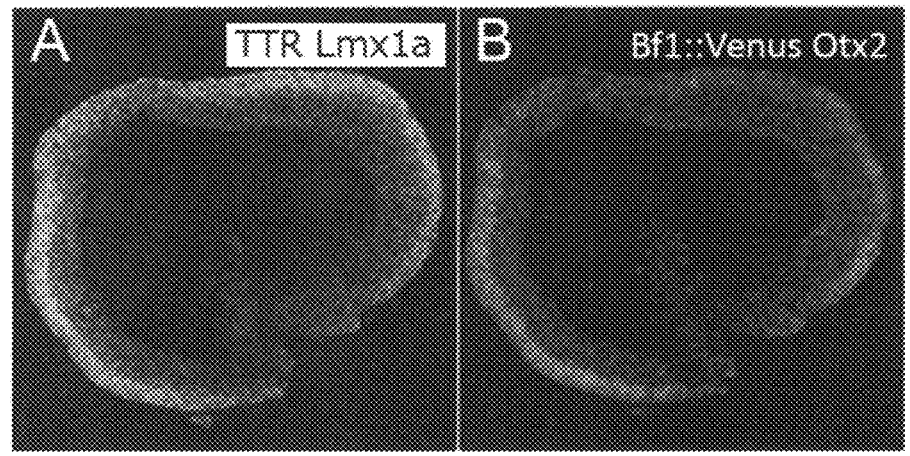
FIG. 5 shows differentiation induction of human pluripotent stem cells into cortical hem. (A) Lmx1a expression in cortical hem induced from pluripotent stem cells. TTR expression is not observed. (B) Otx2 expression in cortical hem induced from pluripotent stem cells. Aggregates mainly composed of Foxg1::venus weakly positive neuroepithelium were formed.

As mentioned above, when cultured under conditions with enhanced Wnt signal from day 18, aggregates mainly containing neuroepithelium expressing cortical hem markers Lmx1a, Otx2 and being Foxg1::venus weakly positive were formed (FIG. 5A, B). The neuroepithelium did not express choroid plexus marker TTR (FIG. 5A). From such marker expression profile, a fimbrial progenitor tissue cortical hem is considered to have been selectively induced under these conditions. Selective formation of cortical hem under these conditions was observed with good reproducibility in not less than 80% of the aggregates.

Example 6

Continuous Three Dimensional Formation of Choroid Plexus, Hippocampal Progenitor Tissue and Cortical Progenitor Tissue
(Method)

Human ES cell aggregates were cultured in a V bottom 96 well plate under the culture conditions as in Example 1 up to 18 days after differentiation induction. Thereafter, suspended aggregates were transferred to a non-cell adhesive petri dish (diameter 9 cm), and suspension culture was performed at 37° C. in the presence of 5% $CO_2$, 40% $O_2$. The culture medium used for the culture from day 18 to day 35 was DMEM/F12 medium (Gibco/Invitrogen) added with 1% N2 supplement (Gibco/Invitrogen), 1% lipid concentrate (Chemically defined lipid concentrate, Gibco/Invitrogen), 10% FBS, and 5 µg/ml heparin. However, 3 µM GSK-3β inhibitor CHIR99021 and 0.5 nM BMP4 were added to the culture medium only in the period of from day 18 to day 21 and allowed to react. While these substances promotes differentiation into choroid plexus and cortical hem as shown in Examples 4 and 5, in culture of Example 6, their action was limited to 3 days, and removed from the culture from day 21. These aggregates were analyzed by immunohistostaining on day 35.
(Results)

Figure 6:
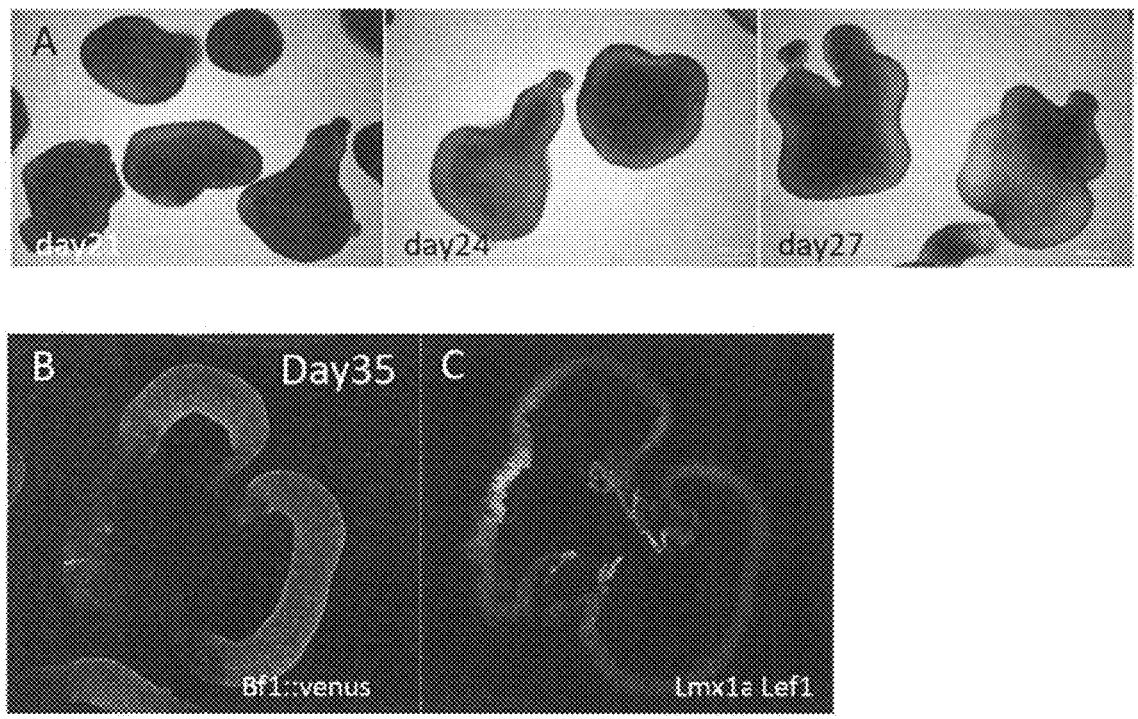
FIG. 6 shows continuous formation of choroid plexus, hippocampal progenitor tissue and cortical progenitor tissue. (A) Cell aggregates containing both Foxg1::venus positive neuroepithelium and Foxg1::venus negative neuroepithelium. (B) Bf1(Foxg1)::venus expression in cell aggregate containing choroid plexus, hippocampal progenitor tissue and cortical progenitor tissue. (C) Expression of Lmx1a and Lef1 in cell aggregates containing choroid plexus, hippocampal progenitor tissue and cortical progenitor tissue.

As mentioned above, when cultured under conditions enhancing Wnt signal and BMP signal only transiently and removing same thereafter, the aggregate showed formation of Foxg1::venus positive neuroepithelium and Foxg1::venus negative neuroepithelium (FIG. 6A) on days 21-27 of culture, and they constituted a continuous neuroepithelium. Such state of containing both Foxg1::venus positive and negative neuroepithelia adjacently was observed with good reproducibility in not less than 80% of the aggregates. The Foxg1::venus negative neuroepithelium had a structure protruding outward from the aggregate, and the tip thereof had a hemispherical structure. On day 35 from the start of differentiation induction, Lmx1a positive and Foxg1::venus negative choroid plexus region, a Lmx1a and Otx2-expressing and Foxg1::venus weakly positive cortical hem region, a region of Lef1 positive and Foxg1::venus positive hippocampal progenitor tissue, and Lef1 negative and Foxg1::venus positive cortical progenitor tissue were continuously formed in these aggregates (FIG. 6B, C). Such continuous self-formation of choroid plexus, a hippocampal progenitor tissue and a cortical progenitor tissue in one aggregate was observed with good reproducibility in not less than 80% of the aggregates.

Example 7-1

Continuous Three Dimensional Formation of Each Region of Hippocampal Tissue
(Method)

After culture in a V bottom 96 well plate under culture conditions of Example 1 up to 18 days after differentiation induction, suspended aggregates were transferred to a non-cell adhesive petri dish (diameter 9 cm), and suspension culture was performed at 37° C. in the presence of 5% $CO_2$, 40% $O_2$. The culture medium used for the culture from day 18 was any of the following two media.
1) DMEM/F12 medium (Gibco/Invitrogen) added with 1% N2 supplement (Gibco/Invitrogen), 1% lipid concentrate (Chemically defined lipid concentrate, Gibco/Invitrogen), 10% FBS and 5 µg/ml heparin
2) Neurobasal medium (Gibco/Invitrogen) added with 2% B27 supplement without vitamin A (Gibco/Invitrogen), 2 mM L-glutamine and 10% FBS Similar to Example 6, 3 µM GSK-3β inhibitor CHIR99021 and 0.5 nM BMP4 were added to these culture media and reacted only in the period of from day 18 to day 21. These aggregates were analyzed by immunohistostaining on day 61 and day 75.
(Results)

Figure 7:
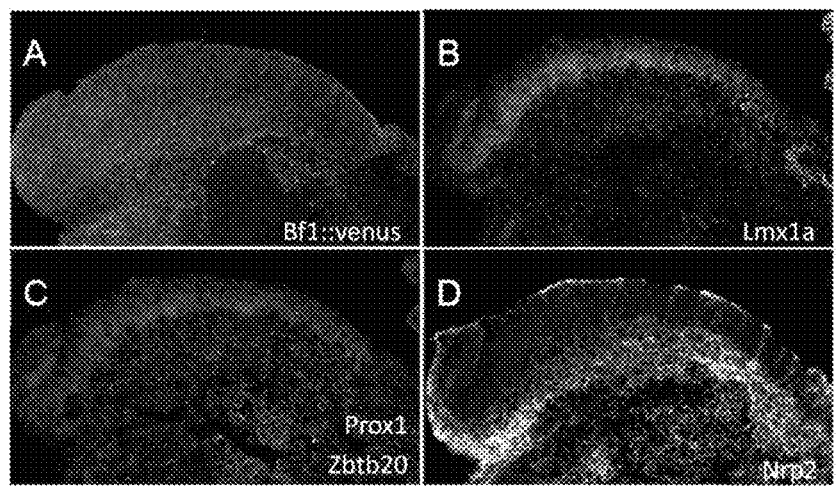
FIG. 7 shows differentiation induction of human pluripotent stem cells into hippocampal progenitor tissue. (A-D) Expression of Bf1(Foxg1)::venus (A), Lmx1a (B), Prox1 Zbtb20 (C) and Nrp2 (D) in cell aggregate on day 61. (E-H) Expression of Foxg1::venus, Lmx1a and Lef1 (E), Zbtb20 (F), Prox1 (G) and Prox1 and Zbtb20 (H) in cell aggregate on day 75.
Figure 7:
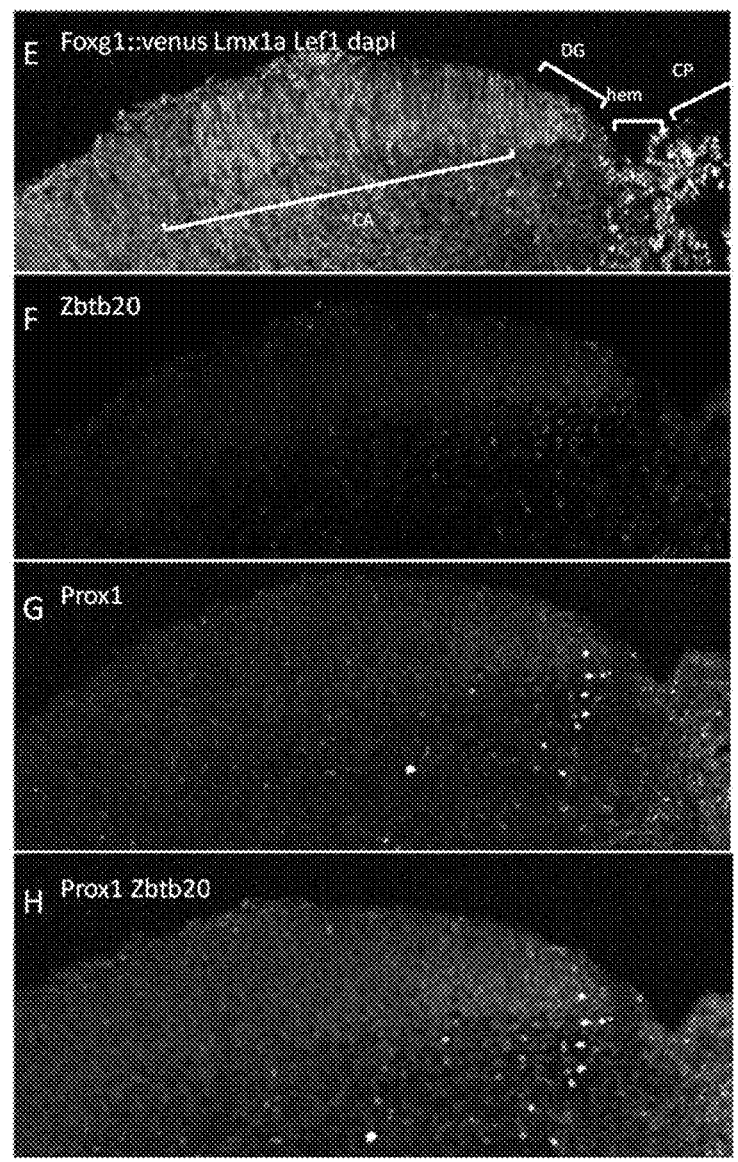

In a culture using the culture medium of any of the above-mentioned 1) and 2), when continuously cultured up to day 61, hippocampal progenitor tissue marker Lef1 positive and Foxg1::venus positive neuroepithelium was formed in the aggregates (FIG. 7A, B). The neuroepithelium contained many hippocampal progenitor tissue marker Nrp2 positive nerve cells (FIG. 7D). The neuroepithelium also contained many hippocampal neuron and progenitor cell marker Zbtb20 positive cells (FIG. 7C). In fetal hippocampal progenitor tissue, an expression intensity gradient in which expression of Zbtb20 in ventricular zone and subventricular zone in the neuroepithelium is strong in progenitor tissue of dentate gyrus (part adjacent to choroid plexus and cortical hem), and weak in progenitor tissue of Ammon's horn (part far from choroid plexus and cortical hem) was observed. Similarly, in Lef1 positive neuroepithelium formed from human ES cells, an expression intensity gradient in which expression of Zbtb20 is stronger in a part adjacent to regions of choroid plexus (Lmx1a positive, Foxg1::venus negative) and cortical hem (Lmx1a positive, Foxg1::venus weakly positive), and becomes weaker as it gets farther therefrom was observed (FIG. 7A, B, C). When the culture was continued under the same conditions up to day 75, formation of a region expressing both Zbtb20 and Prox1 characteristic of dentate gyrus neuron (FIG. 7E, DG) was confirmed between Zbtb20-weakly positive Ammon's horn region (FIG. 7E, CA), and cortical hem (FIG. 7E, hem) and choroid plexus (FIG. 7E, CP). These indicate that regions possibly becoming dentate gyrus tissue and Ammon's horn tissue are continuously formed in hippocampal tissues.

Example 7-2

Mature Hippocampal Neuron Obtained by Continuous Three Dimensional Formation of Each Region in Hippocampal Tissue and Dispersion Culture
(Method)

Continuous hippocampal tissues were induced by the method of Example 7-1, the cell aggregates obtained during Day 60-90 were dispersed into single cells with a cell dissociation solution such as a papain enzyme solution (SUMITOMO BAKELITE, MB-X9901) and the like, and the cells were seeded on a glass dish, slide and the like to perform flat plane culture. Before performing culture, the surface of the glass was coated with poly-D-Lysine (200 µg/ml) at 4° C. overnight, and with Laminin 20 µg/ml/ Fibronectin 8 µg/ml at 37° C. overnight.

The culture medium used was Neurobasal medium (Gibco/Invitrogen) added with 2% B27 supplement without vitamin A (Gibco/Invitrogen), 2 mM L-glutamine and 10% FBS. The cells cultured under these flat plane conditions adhered to the surface of the glass within 2-3 days after dispersion and started to elongate neurite, which were analyzed by immunohistostaining between d140 and d197.
(Results)

Figure 8:
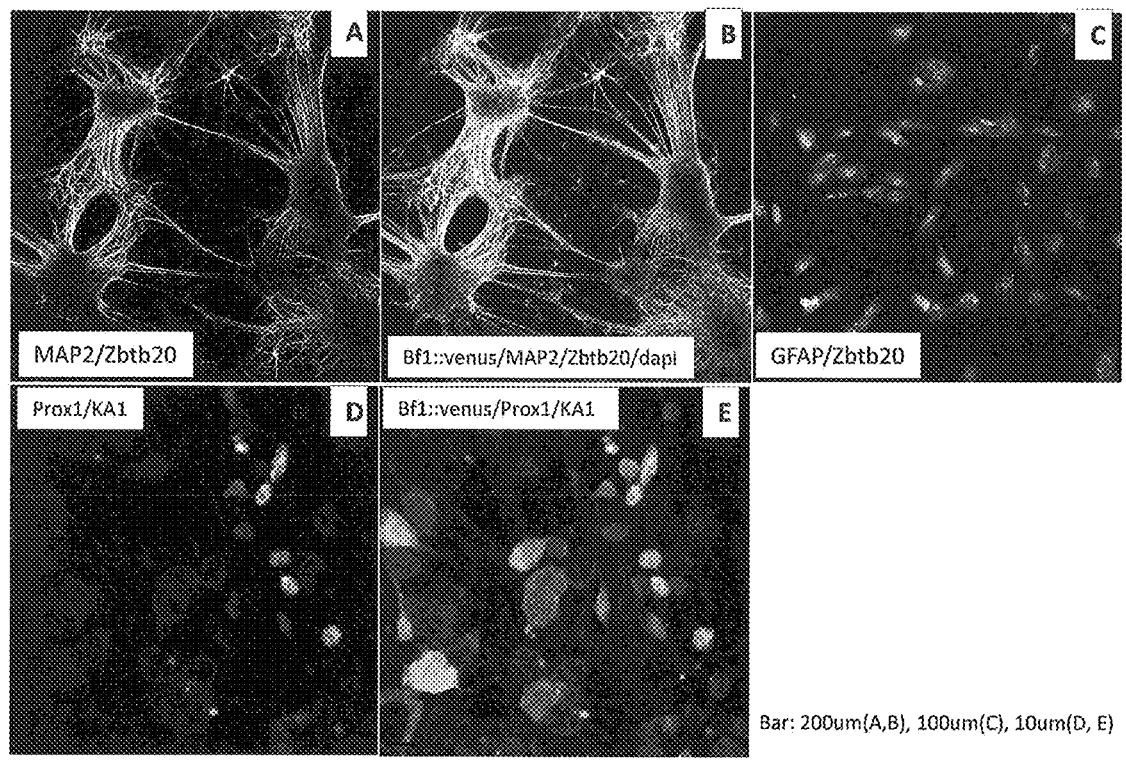
FIG. 8 shows plate dispersion culture of 3D hippocampal tissue induced from human ES cells. (A) Expression of hippocampus marker Zbtb20 in MAP2 positive cells with neuronal dendrite. (B) Bf1(Foxg1)::venus expression in Zbtb20 positive cells. (C) Expression of astrocyte marker GFAP in Zbtb20 positive cells having a glial cell-like morphology. (D) Expression pattern of dentate granule cell marker Prox1 and CA3 pyramidal cell marker KA1, among hippocampus regions, in dispersion culture. Prox1 expression is observed in compact cells having a cell body diameter of about 5-10 μm, and KA1 expression is observed in large cells having a pyramidal cell-like morphology and a cell body diameter of 10-20 μm. (E) Bf1(Foxg1)::venus expression in the cells of FIG. D. Bar: 200 μm (A, B), 100 μm (C), 10 μm (D, E).

The cells dispersed into single cells easily form small aggregates, and neurite was elongated between the neurons thereof (FIG. 8A). Hippocampus marker Zbtb20 was positive in almost all cells (FIG. 8B), and Foxg1::venus was also positive at Day 197 (FIG. 8B). While diffused cells other than neuron with MAP2 positive dendrite were found, since such cells were also Zbtb20(+), had a glial cell-like shape, and were GFAP positive, they were suggested to be astrocyte (FIG. 8C). Zbtb20 positive cells contained hippocampus dentate gyrus marker Prox1-positive cells and hippocampus CA3 region marker KA1-positive cells, in which the Prox1 positive cell is a comparatively small circular cell suggesting a granular cell, whereas the KA1 positive cell had a comparatively large pyramidal cell-like shape (FIG. 8D-E). This was considered to be consistent with the formation of granular cells in the dentate gyrus, and pyramidal cells in the CA region in vivo. The proportion of the Zbtb20 positive cells was about 80%, and this expression rate was observed with good reproducibility.

From these results, based on the marker expression and cell morphology, it was suggested that granular cells of hippocampus dentate gyrus and pyramidal cells of hippocampus CA3 region could be induced.

Example 7-3

Functional Analysis of Mature Hippocampal Neuron Obtained by Dispersion Culture of Three-Dimensionally Induced Hippocampal Tissue
(Method)

By a method similar to that in Example 7-1, continuous hippocampal tissues were subjected to dispersion culture. In this experiment, flat plane culture was performed by seeding on a glass or plastic dish, slide and the like. For culture, a glass or plastic surface was coated with poly-D-Lysine (100 µg/ml) at 37° C. for 3 hr, and Laminin 20 µg/ml/Fibronectin 8 µg/ml overnight at 37° C.

The culture medium used for day 1-2 of dispersion was Neurobasal medium (Gibco/Invitrogen) added with 2% B27 supplement without vitamin A (Gibco/Invitrogen), 2 mM L-glutamine, 1% FBS, 20 ng/ml BDNF, 20 ng/ml NT-3, and 10 µM Y-27632. From day 3 of culture, Neurobasal medium (Gibco/Invitrogen) added with 2% B27 supplement without vitamin A (Gibco/Invitrogen), 2 mM L-glutamine, 10% FBS, BDNF 20 ng/ml, and NT-3 20 ng/ml was used and a half amount of the medium was exchanged every three days. In days 30-60 from dispersion, the cells were incubated in fluo4-AM (life technologies, F-14201) (5 µM) at 37° C. for 45 min, washed with the medium and subjected to the functional analysis by calcium imaging using LCM. Also, the cells obtained by dispersion culture by the same method were electrophysiologically analyzed by the Patch clamp technique. The measurement was performed by whole cell patch clamp, and the glass electrode (electrode resistance value 3-6 MΩ) was used after filling the inside with an internal solution buffer (120 mM K-Gluconate, 10 mM KCl, 10 mM EGTA, and 10 mM Hepes-containing buffer adjusted to pH 7.2 with KOH), and the inside of the chamber with an external solution buffer (140 mM NaCl, 2.5 mM $CaCl_2$, 2 mM $MgCl_2$, 10 mM Glucose, 1 mM $NaH_2PO_4$, and 10 mM Hepes-containing buffer adjusted to pH 7.4 with NaOH). The measurement was performed by EPC10 (HEKA). All experiments were performed at room temperature. The membrane capacitance components were compensated, and the experiment was performed under conditions in which the series resistance value falls within 3 times the electrode resistance value. The electric potential of the electric potential dependent sodium, potassium electric currents was maintained at −60 mV, and the measurement was performed upon stimulation from −80 mV to +60 mV by −10 mV. For sEPSC, time-course electric current was measured when the voltage was maintained at −60 mV, and the medicament used was DNQX (sigma, D0540) at a final concentration of 10 µM. As the action potential, the membrane potential upon hyperpolarizing stimulation was measured.
(Results)

Figure 9:
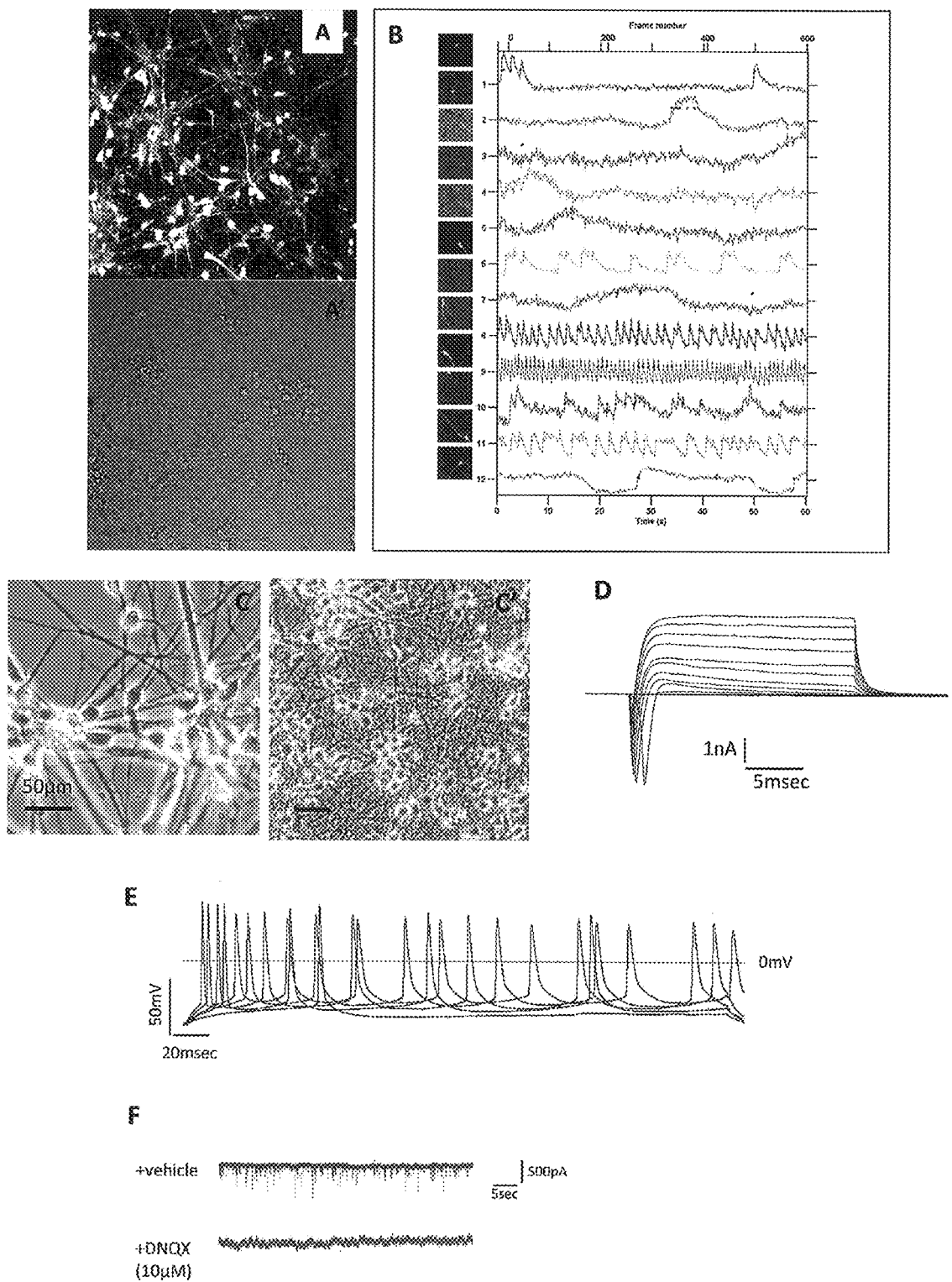
FIG. 9 shows calcium imaging and electrophysiological analysis of hippocampal progenitor tissues after long-term dispersion culture. (A-A') shows signal expression image and bright field image thereof in calcium imaging. (B) shows various time-course response patterns of calcium signals in respective cells. (C-C') Bright field image in electrophysiologic test. (D) Sodium-potassium electric current response. (E) Induced action potential. (F) sEPSC and inhibition thereof by DNQX. Bar: 50 μm (C, C').

In calcium imaging after progress of 30-31 days after dispersion, many neurons showed firing activity associated with calcium influx (FIG. 9A, A'), various time-course activity patterns of each cell could be confirmed (FIG. 9B). In patch-clamp performed on day 53 after dispersion, sodium, potassium electric current response, induced action potential, and spontaneous excitatory postsynaptic current (sEPSC) due to the stimulation with electric potential were observed (FIG. 9C-E). sEPSC was observed to be inhibited by AMPA-type glutamate receptor antagonist DNQX (FIG. 9F).

These experiments suggest that spontaneous neural activity was found in the neuron obtained in Example 7, and the cells thereof showed activity in response to the stimulation and a functional nerve also having a synapse network was obtained.

Example 8

Three Dimensional Formation of Cerebral Cortex Having a Second Trimester Type Multilayered Structure from Human Pluripotent Stem Cells
(Method)

Up to day 35 of differentiation induction, cells were cultured under culture conditions of Example 1. That is, human ES cell aggregates were cultured in a V bottom 96 well plate up to 18 days after differentiation induction, then suspended aggregates were transferred to a non-cell adhesive petri dish (diameter 9 cm), and suspension culture was performed from day 18 of differentiation induction, at 37° C. in the presence of 5% $CO_2$, 40% $O_2$. To maintain aggregates in healthy condition for a long term, after day 35, the aggregates were divided into half once per 2 weeks, and culture was continued in the culture medium described in Example 1. After day 56 of differentiation induction, the cell aggregates were transferred to an oxygen highly-permeable non-cell-adhesive culture dish (diameter 6 cm, SARSTEDT) and culture was continued. After day 70 of differentiation induction, the concentration of Matrigel growth factor reduced (BD Bioscience) was changed to 2% and the culture was continued. These aggregates were analyzed by immunohistostaining on day 70 and day 91.
(Results)

Figure 10:
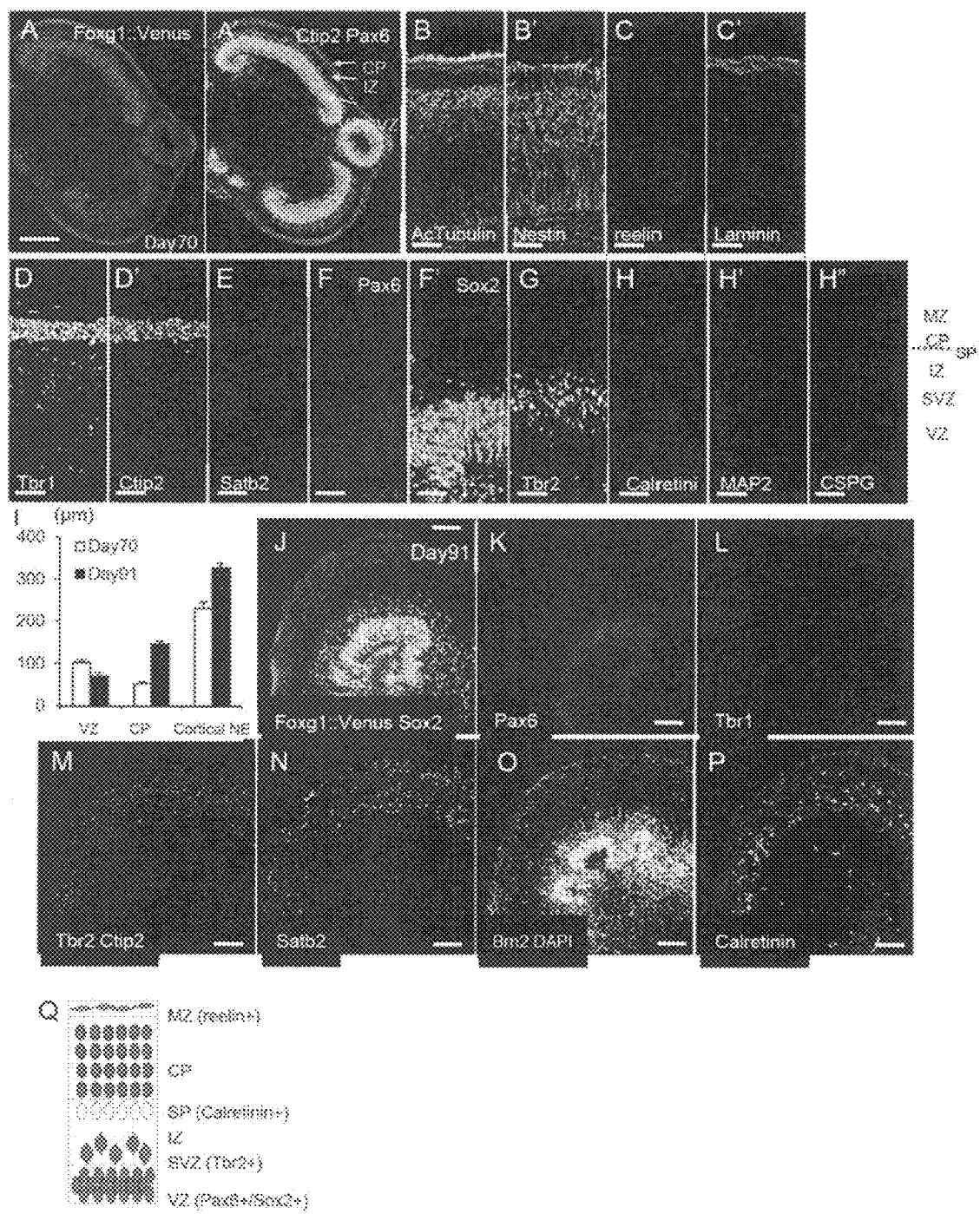
FIG. 10 shows differentiation induction of human pluripotent stem cells into cortical progenitor tissue having a second trimester-type multilayered structure. (A and A') Sections of day 70 human pluripotent stem cell-derived cortical neuroepithelium. A' shows Ctip2 and Pax6 immunostainings. Clear separation of ventricular zone (Pax6$^+$), subventricular zone, intermediate zone, and cortical plate (Ctip2$^+$) was seen even at the low-magnification view. (B-H") Immunostaining of day 70 cortex with zone-specific markers. (I) Total thickness of cortical neuroepithelium (Cortical NE) and thickness of ventricular zone (VZ) and cortical plate (CP) on days 70 and 91. (J-P) Immunostaining of day 91 cortical neuroepithelium with zone specific markers. (Q) Schematic of the laminar structure seen in long-term culture of hESC-derived cortical neuroepithelial.

When cultured under the above-mentioned conditions, the aggregates showed a morphologically clear layered structure on day 70 from the start of differentiation induction (FIG. 10A-B'). On the outermost superficial layer of the layered structure, laminin was accumulated and a marginal zone containing Reelin positive Cajal-Retzius cells was formed (FIG. 10C, C'). A cortical plate containing Tbr1 positive, Ctip2 positive neurons of deep-cortical plate was observed immediately underneath the marginal zone (FIG. 10 D, D'). At this time point, not many neurons expressed a superficial-cortical plate marker Satb2 (FIG. 10E). A thin ventricular zone having a high cell density and containing Pax6 positive and Sox2 positive neuronal progenitor cells (FIG. 10F, F'), and a subventricular zone containing Tbr2 positive cells thereabove (FIG. 10G) were formed on the luminal side. A region containing scattered cells and very similar to the intermediate zone in the second trimester was developed between the cortical plate and the subventricular zone. A Calretinin positive and MAP2 positive cell layer containing many neurites was formed beneath the cortical plate (FIG. 10H, H'). Since accumulation of chondroitin sulfate proteoglycan (CSPG) was observed in this cell layer (FIG. 10H"), formation of a subplate was suggested. On day 91 from the start of differentiation induction, a cerebral cortical tissue having the multilayered structure became thicker (FIG. 10I), and had a developed Sox2 positive and Pax6 positive ventricular zone and a Tbr2 positive subventricular zone even at this stage (FIG. 10J, K, M). The cortical plate became similarly thick (FIG. 10I), and it was clarified that not only Tbr1 positive, Ctip2 positive neurons of the deep-cortical plate, but also many Satb2 positive, Brn2 positive neurons of the superficial-cortical plate were contained (FIG. 10L-O). Calretinin positive subplate was observed beneath the cortical plate even at this stage (FIG. 10P). Thus, the present culture method has enabled three dimensional formation of a tissue having a multilayered structure shown in the cerebral cortex in the human second trimester along the superficial-deep portion axis shown in FIG. 10Q.

Example 9

Formation of Spontaneous Axis of Cerebral Cortex and Exogenous Control Thereof
(Method)

Up to day 42 of differentiation induction, cells were cultured under culture conditions similar to those of Example 1. That is, human ES cell aggregates were cultured in a V bottom 96 well plate up to 18 days after differentiation induction, suspended aggregates were transferred to a non-cell adhesive petri dish (diameter 9 cm), and suspension culture was performed from day 18 to day 42 of differentiation induction at 37° C. in the presence of 5% $CO_2$, 40% $O_2$. The culture medium used was the same as used in Example 1. When an influence of the exogenous factor was studied, 200 ng/mL of FGF8b was added to the culture medium and allowed to react from day 24 to day 42. At any conditions, the aggregates were analyzed by immunohistostaining on day 42.
(Results)

Figure 11:
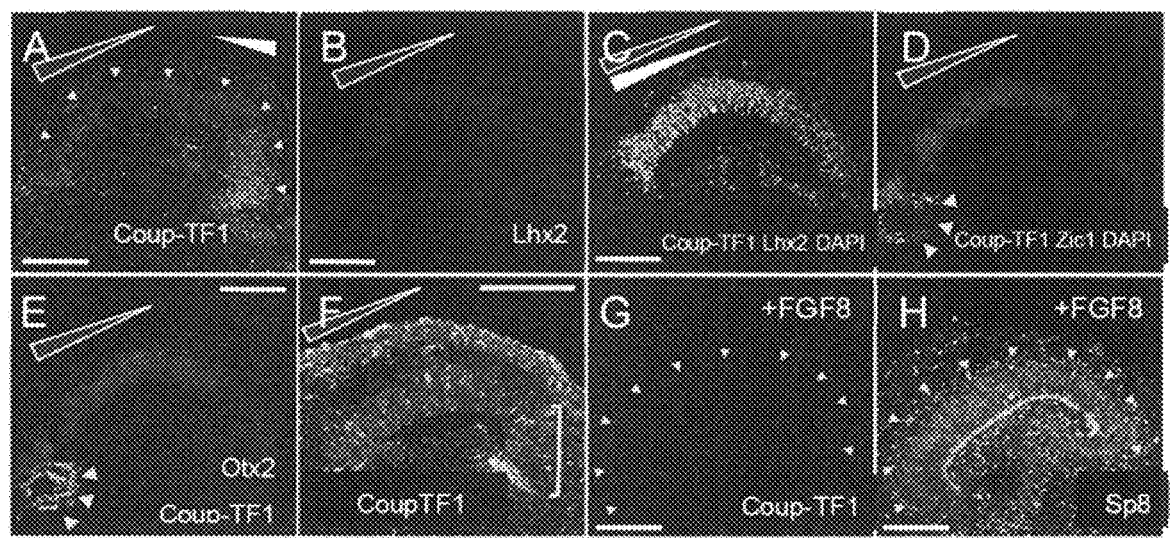
FIG. 11 shows spontaneous axis formation in cerebral cortex and control by exogenous factor. (A-F) shows expression of Coup-TF1 (A), Lhx2 (B), Coup-TF1 and Lhx2 (C), Coup-TF1 and Zic1 (D), Coup-TF1 and Otx2 (E), CoupTF1 and phosphorylated Erk (F) in cell aggregate on day 42. (G) Attenuation of CoupTF1 expression by treatment with FGF8b. (H) Increase of Sp8 expression over whole ventricular zone by FGF8b treatment. (I) Changes in Coup-TF1 and Sp8 expression pattern by FGF8b treatment.
Figure 11:
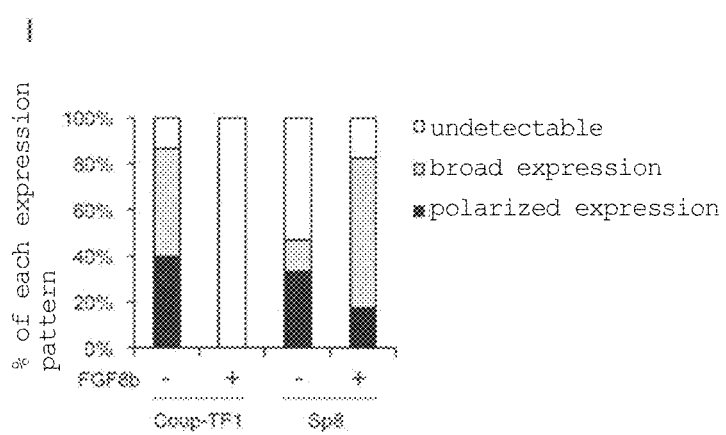

As a dorsocaudal marker that is expressed and forms a gradient from the dorsocaudal side to the rostral side in the cortical ventricular zone in the early trimester, CoupTF1 and Lhx2 are known. On the other hand, as a rostral marker that shows a reverse gradient, Sp8 is known. When an exogenous factor is not reacted, a dorsocaudal marker CoupTF1 was expressed stronger on one side and weaker on the opposite side also in the cortical ventricular zone induced from human pluripotent stem cells (FIG. 11A). The expression of a rostral marker Sp8 showed a reverse gradient to that of CoupTF1 (FIG. 11A), and the expression of the other dorsocaudal marker Lhx2 showed the same gradient as that of CoupTF1 (FIG. 11B, C). In a telencephalon tissue in vivo, the dorsocaudal side of the cerebral cortex is adjacent to the cortical hem. Also, in the cortical ventricular zone induced from human pluripotent stem cells, a region in which dorsocaudal markers CoupTF1 and Lhx2 are strongly expressed was formed adjacent to a region expressing cortical hem markers Zic1 and Otx2 (FIG. 11D, E). These suggest that cerebral cortex induced from human pluripotent stem cells spontaneously acquired polarity from the dorsocaudal side to the rostral side in a self-organization manner under these conditions.

It is known that FGF8 is important for acquiring the specificity to the rostral side of cerebral cortex in vivo. When an exogenous factor is not reacted in the culture of aggregates, phosphorylated Erk caused by FGF signal was strongly accumulated on the rostral side where expression of a dorsocaudal marker CoupTF1 is weak (FIG. 11F). On the other hand, when an exogenous FGF8b was reacted, overall expression of CoupTF1 was attenuated, and expression of Sp8 conversely increased over the whole ventricular zone (FIG. 11G-I). These suggest that the regionality of the frontal lobe, occipital lobe and the like along the dorsal-ventral axis or anterior-posterior axis of the cerebral cortex can be selectively controlled by imparting an exogenous signal, thereby leading to induction.

Example 10

(Method)
Maintenance and Differentiation Culture of hESCs

Human ES cells (hESCs) (KhES-1) were used according to the hESC research guidelines of the Japanese government. hESCs were maintained with a feeder of MEFs inactivated by mitomycin C treatment in DMEM/F12 (Sigma) supplemented with 20% (vol/vol) Knockout Serum Replacement (KSR; Invitrogen), 2 mM glutamine, 0.1 mM nonessential amino acids (Invitrogen), 5 ng/mL recombinant human bFGF (Wako), 0.1 mM 2-mercaptoethanol (2-ME), 50 U/mL penicillin, and 50 µg/mL streptomycin at 37° C. under 2% $CO_2$. For passaging, hESCs were detached and recovered en bloc from the feeder cells by treating them with PBS containing 0.25% trypsin, 0.1 mg/mL collagenase IV, 20% KSR and 1 mM $CaCl_2$ at 37° C. for 7 min. The detached hESC clumps were broken into smaller pieces (several dozens of cells) by gentle pipetting. The passages were performed at a 1:3-1:4 split ratio.

For SFEBq culture, hESCs were dissociated to single cells with TrypLE Express (Gibco/Invitrogen) containing 0.05 mg/mL DNase I (Roche) and 10 µM Y-27632, and seeded into each well of low-cell-adhesion surface-coated 96-well plates with V-bottomed conical wells using cortex differentiation medium containing 20 µM Y-27632 to be aggregated. The cortical differentiation medium was G-MEM (Gibco/Invitrogen) supplemented with 20% KSR (Knockout Serum Replacement), 0.1 mM nonessential amino acids (Gibco/Invitrogen), 1 mM pyruvate (Sigma), 0.1 mM 2-mercaptoethanol, 100 U/mL penicillin, and 100 µg/mL streptomycin. Defining the day on which the SFEBq culture was started as day 0, IWR1e (Wnt inhibitor) and SB431542 (TGFβ inhibitor) were added to culture to reach 3 µM and 5 µM, respectively, from day 0 to day 18.

Cortical neuroepithelium induced from hESCs were subjected to culture under the following conditions. On day 18, the cell aggregates were transferred to a 9-cm Petri dish (non-cell adhesive surface coat) and further cultured in DMEM/F12 medium (Gibco/Invitrogen) supplemented with 1% N2 supplement (Gibco/Invitrogen), 1% lipid concentrate (Chemically Defined Lipid Concentrate, Gibco/Invitrogen), 0.25 mg/mL Fungizone, 100 U/mL penicillin, and 100 µg/mL streptomycin at 37° C. in the presence of 5% $CO_2$ and 40% $O_2$. From day 35, 10% FBS, 5 µg/mL heparin, and 1% Matrigel growth factor-reduced (BD Biosciences) were also added to the medium. To prevent cell death in the central portions of cell aggregates, the aggregates were cut into half-size with fine forceps under a dissecting microscope every 2 wk after day 35 and were cultured using a lumox culture dish (SARSTEDT; $O_2$ penetrating) after day 56. From day 70, the concentration of Matrigel was increased (final 2%) and B27 supplement (Gibco/Invitrogen) was added to the medium.

Anterior induction of cortical neuroepithelium was performed by adding human recombinant FGF8b (Gibco, 200 ng/mL) during culture days 24-42. The cell aggregates were fixed on culture day 42.

Figure 18:
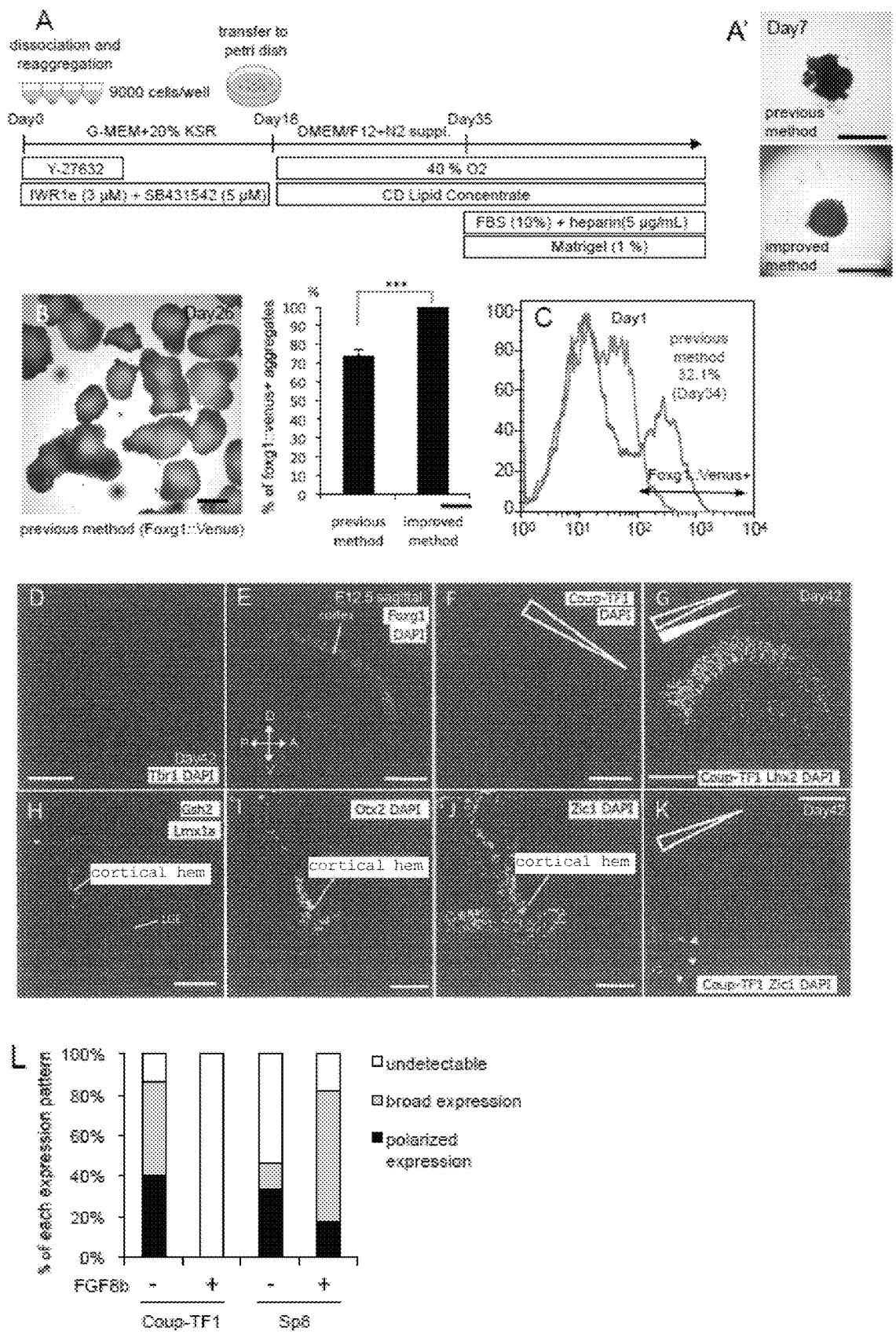
FIG. 18 shows axial polarity in hESC-derived cortical neuroepithelium. (A) Schematic of improved culture procedures. (A') Comparison of aggregate formation of hESCs on day 7. (Upper) The present inventor's previous culture; (Lower) the improved culture, which promoted the formation of undivided, smooth aggregates from dissociated hESCs. (B) Percentages of hESC aggregates (day 26) that contained neuroepithelium with foxg1::Venus signals. ***$P<0.001$, Student t tests. (C) Representative FACS analysis for foxg1::Venus+ populations. Gray, control (day 1 culture); red, day 34 culture under the previous conditions. (D) Immunostaining signals of Tbr1 in the cortical plate of day 42 cortical neuroepithelium. (E and F) Localization of regional markers in the mouse fetal telencephalon (Foxg1+; E). Coup-TF1 expression in the cortical neuroepithelium is strong in the dorsocaudal region but weak in the ventrorostral region (F). (G) Double immunostaining of CoupTF1 and Lhx2 showed that their expression patterns were similarly biased. (H-J) Parasagittal sections of the mouse telencephalon at E12.5. Gsh2, LGE (lateral ganglionic eminence) marker (H); Lmx1a, cortical hem and choroid plexus marker (H); Otx2 and Zic1, cortical hem markers (I and J). (K) Double immunostaining of Coup-TF1 and Zic1 showed that the cortical hem marker Zic1 was expressed in the tissue flanking the cortical neuroepithelium on the side with strong Coup-TF1 expression. (L) Effects of Fgf8 treatment (days 24-42) on the expression of CoupTF1 and Sp8. Percentages of polarized expression (black), board expression (gray), and undetectable signals (open) were counted in the cross sections (at the longest-axis position) of cortical neuroepithelium. Because it was counted in this manner, the percentages of polarized expression patterns could be somewhat underestimated. (Scale bars, 1 mm in A' and B; 200 µm in D, G, and I-K; 500 µm in E, F, and H.) Bars in graph, SEM.

Ventralization of cortical neuroepithelium was performed by adding hedgehog agonist SAG (30 nM or 500 nM) during culture days 15-21. The cell aggregates were fixed on culture day 35.
(Results)
Intracortical Polarity in Self-Organized Cortical NE For the improved SFEBq culture (FIGS. 18A and A'), 9000 dissociated hESCs were plated into each well of low-cell-adhesion V-bottomed 96-well plates (document 15)

and cultured them in G-MEM-KSR medium supplemented with the Rho-kinase inhibitor (Y-27632) (16) (FIG. 18A). Then, the cell aggregates were transferred to 9-cm non-cell-adhesive culture dishes and cultured in the presence of 40% $O_2$. The addition of lipid concentrate (day 18), 10% FBS, heparin, and a low concentration of Matrigel (1%) (day 35) was performed for long-term maintenance of ventricular zone, whereas the addition of TGFβ inhibitor (SB431542) and Wnt inhibitor (IWR1e) for the first 18 days was performed for the efficient induction of telencephalic region.

Figure 12:
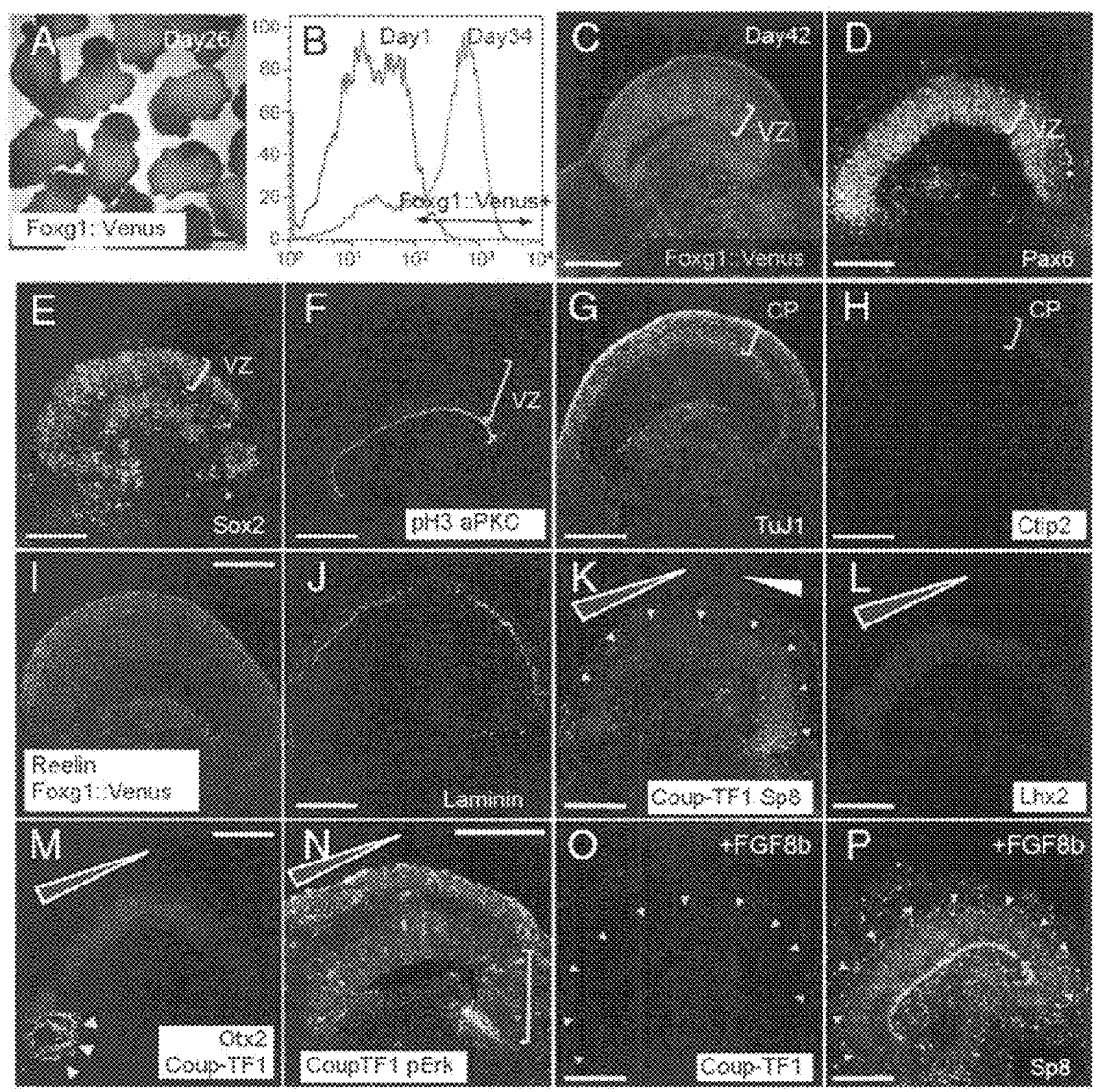
FIG. 12 shows axial polarity in cortical neuroepithelium self-organized from hESCs. (A) hESC aggregates containing cortical neuroepithelium visualized with foxg1::Venus on day 26. (B) Representative FACS analysis for foxg1::Venus positive populations. (C-J) Immunostaining of semispherical cortical structures self-formed from foxg1::venus hESCs. VZ, ventricular zone. (K-N) Self-formation of axial polarity seen in hESC-derived cortical neuroepithelium. Cortical hem-like tissues (Otx2+; M) were located in the flanking region of cortical neuroepithelium on the side strong for the dorsocaudal markers Coup-TF1 (K) and Lhx2. A higher level of pErk signals was observed on the side opposite to Coup-TF1 expression (N). Gradient and polarity of expression are indicated by triangles. Arrowhead, ventricular zone (VZ) (note that the gradients of marker expression are seen in the ventricular zone). (O and P) Fgf8 treatment suppressed CoupTF1 and expanded the expression of the ventrorostral marker Sp8. (Scale bars, 1 mm in A; 200 µm in C-P.) Nuclear counter staining (blue), DAPI.

Under these improved culture conditions, all hESC-derived aggregates contained neural epithelium positive for foxg1::Venus (telencephalic marker) (document 2) on days 26 (FIG. 12A and FIG. 18B), and 75% or more of total cells (day 34) expressed foxg1::Venus on day 34. In contrast, by the previous method, the efficiency for the foxg1::Venus positive cells was 30-40% of total cells (FIG. 12B and FIG. 18C). The foxg1::Venus positive neural epithelium contained semispherical neural epithelium-like structure (pseudostratified columnar epithelial) with a ventricle-like cavity inside (FIG. 12C; day 42). These neural epithelial structure had a high cell-dense cell layer positive for Pax6 and Sox2 on the luminal side (FIGS. 12D and E), whereas phosphorylated Histon H3 positive cells under mitosis were found in its innermost part (FIG. 12F). These structures were similar to cortical ventricular zone in early trimester. Outside of the ventricular zone-like cell layer expressed a post-mitotic neuron marker Tuj1 (CP; FIG. 12G) and early cortical plate markers Ctip2 and Tbr1 (documents 1 and 2) (FIG. 12H and FIG. 18D). The neuronal layer also contained Reelin-positive Cajal-Retzius cells (FIG. 12I), and a Laminin-rich layer near the surface (FIG. 12J). Thus, self-organizing lamination occurs in this hESC-derived cortical neural epithelium.

Interestingly, the self-organized cortical neural epithelium frequently had an axial polarity. Expression of CoupTF1 in the ventricular zone (FIG. 12K, red), which forms a dorsocaudal-to-rostroventral expression gradient in the fetal brain (FIGS. 18E and F), was stronger on one side of the hESC-derived cortical neural epithelium, whereas the ventrorostral marker Sp8 was expressed in the reverse expression gradient pattern (FIG. 12K, white). Consistent with this phenomenon, Lhx2 expression (forming a dorsal-to-ventral gradient of expression in vivo) was also strong on the same side with CoupTF1 (FIG. 12L and FIG. 18G). The reverse gradient expression pattern of CoupTF1 and Sp8 was already observed on day 35. In the mouse embryo, the dorsocaudal cortical area is flanked by the cortical hem (FIG. 18H-J), which later gives rise to the fimbria region of the hippocampus. Consistent with this phenomenon, the cortical markers Otx2 and Zic1 were expressed in the region flanking the cortical neural epithelium on the side with strong CoupTF1 expression (FIG. 12M and FIG. 18K).

These findings indicate that hESC-derived neural epithelium spontaneously acquires an intracortical dorsocaudal-ventrorostral polarity. In the mouse embryo, FGF8 promotes rostral specification of cortex (document 17). Interestingly, a high level of phosphorylated Erk signals (working downstream of FGF signaling) was observed in the hESC-derived cortical neural epithelium on the side opposite to CoupTF1 expression (FIG. 12N). Conversely, treatment of hESC-derived cortex with exogenous FGF8 caused broad expression of Sp8 at the expense of CoupTF1 expression (FIGS. 12O and P and FIG. 18L), suggesting an active role of FGF-MAPK signaling in this self-organization.

Figure 13:
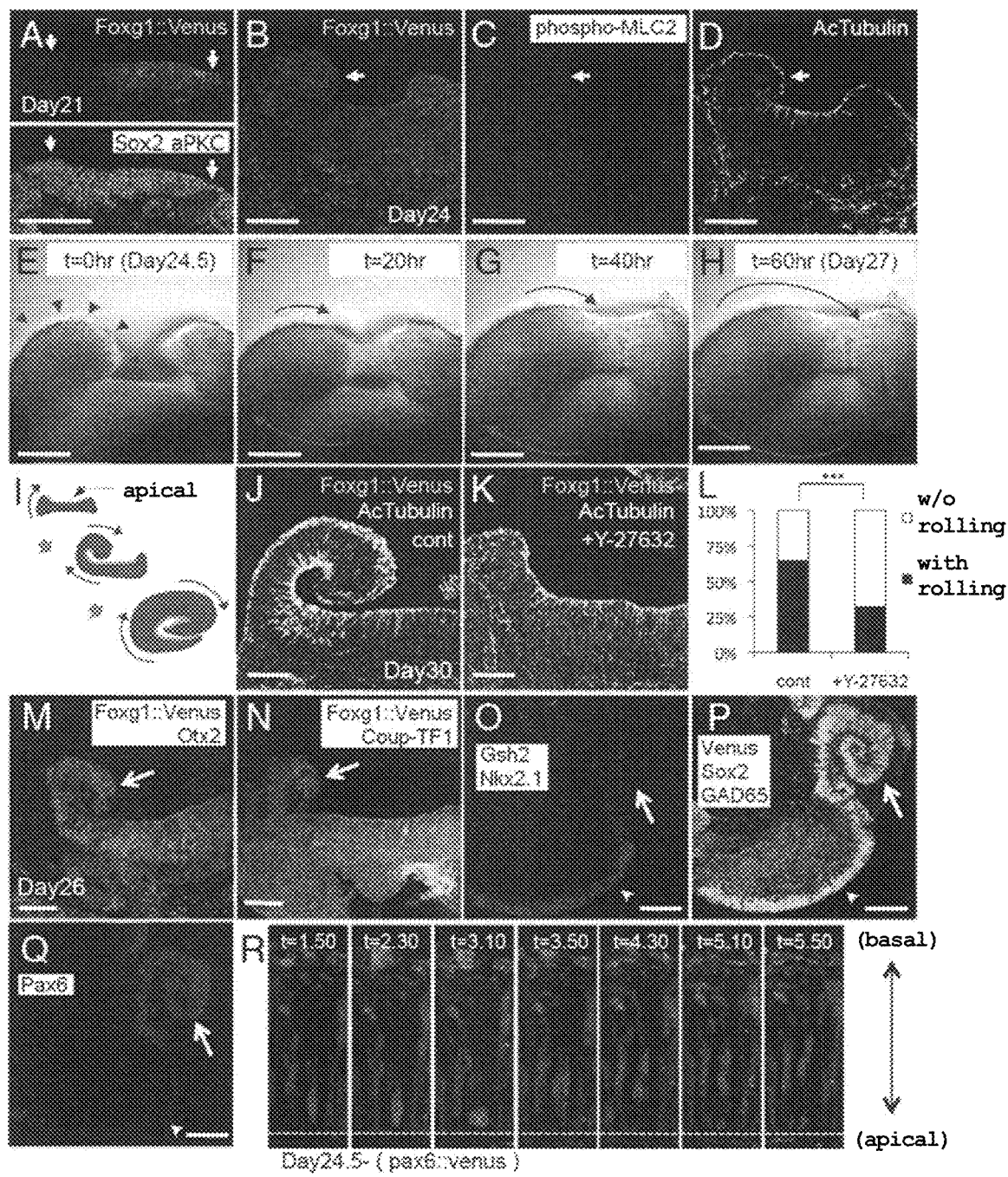
FIG. 13 shows asymmetric rounding morphogenesis in self-organized cortical neuroepithelium. (A-I) Asymmetric progression of rounding morphogenesis of hESC-derived cortical neuroepithelium. Arrows indicate boundary of a cortical neuroepithelium domain in A and rolling epithelium in B-D. Arrowheads indicate rolling epithelium in E. Arrows indicate rounding movements of the neuroepithelium in F-I. (J-L) Effect of the ROCK inhibitor Y-27632 on the rolling of cortical neuroepithelium. (L) Attenuation of rolling morphogenesis with ROCK inhibitor. ***$P<0.001$ in contingency table analysis (2×2) with Fisher's exact test. Treatment group, n=187 neuroepithelium domains; control group, n=130. (M and N) The rolling shape was preferentially observed on the side with strong expression of Otx2 and Coup-TF1 (dorsal and caudal markers). (O-Q) Adjacent formation of neuroepithelium structures of cortex (Pax6+) and LGE (Gsh2+; with GAD65+ GABAergic neurons underneath) on day 35. The cortical side contacting the LGE domain was opposite to the side with strong rolling (arrow). (R) Interkinetic nuclear migration in the hESC-derived cortical neuroepithelium on day 24 (two-photon imaging). Visualized with partial mixing of pax6::venus reporter hESCs with nonlabeled hESCs. Two daughter cells with both apical and basal processes were generated from an apically dividing progenitor. (Scale bars, 200 µm in A; 100 µm in B-H and J-N; 200 µm in O-Q.) Nuclear counter staining (blue), DAPI.

Morphological Change of Self-Organized Cortical Neural Epithelium with Region Specific Curving The expression of the telencephalic marker Foxg1 was first detected in hESC-derived neural epithelium (N-cadherin positive and Sox2 positive) around days 18-20. The apical side (aPKC positive) of the neural epithelium was located on the surface of the aggregate (FIG. 13A, Lower). On day 21, the neural epithelium started to become partially discontinuous and break into several large neural epithelium (FIG. 13A). Subsequently, these segregated cortical neural epithelia became apically concave in curvature (FIG. 13B-D and FIG. 19A, Upper).

Each compartmentalized domain of cortical neural epithelium had an asymmetrically curved structure. One end of the neural epithelium was characterized by a rolling shaped end (FIG. 13B-D, arrows), whereas the other side was characterized by being blunt. Active myosin (indicated by phosphorylated MLC2) was uniformly accumulated throughout the apical surface of the cortical region, including blunt end (FIG. 13C). In live imaging, the rolling side of the cortical region approached the other end and eventually contacted it (FIGS. 13E and F). During this process, the main body of neural epithelium in the cortical region moved around in the same direction with the rolling side (FIG. 2E-H). The rounding morphogenesis eventually generated a semispherical cortical structure with a lumen inside by day 27 (FIG. 13I and FIG. 19A, Lower).

The morphological change the cortical domain with rolling was attenuated by the addition of ROCK inhibitor (FIG. 13J-L), which inhibits the Rho-ROCK-myosin pathway necessary for causing apical constriction. The rolling side of neural epithelium expressed markers for the dorsocaudal side (Otx2 and CoupTF1; FIGS. 13M and N), indicating that the rolling end corresponded to the dorsocaudal side.

Figure 19:
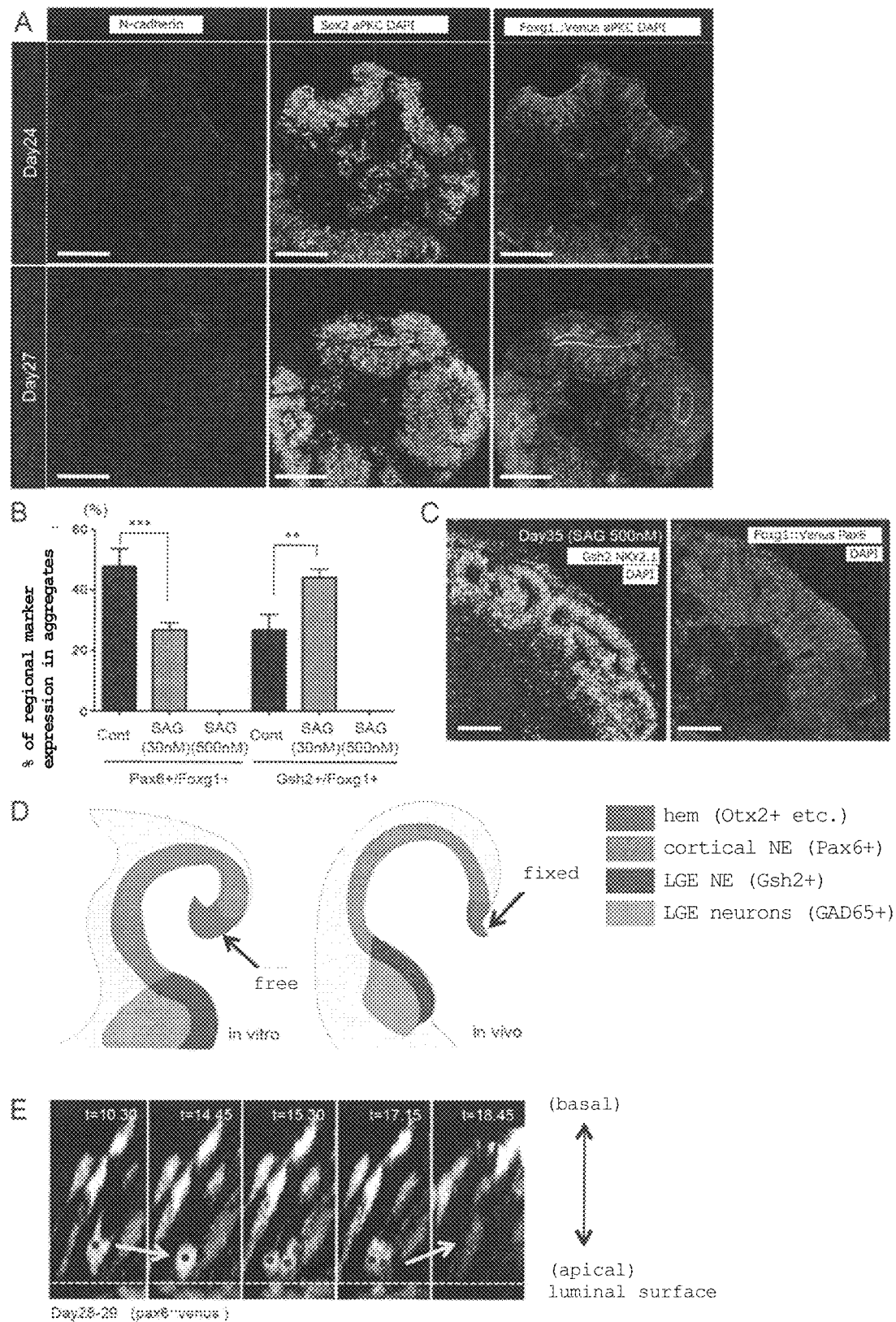
FIG. 19 shows rounding morphogenesis and apical division in cortical neuroepithelium. (A) Spontaneous rounding morphogenesis of cortical neuroepithelium domains in hESC aggregates: (Upper) day 24; (Lower) day 27. aPKC, apical marker. (B) Percentages of Pax6+ (cortical) and Gsh2+ (lateral ganglionic eminence) neuroepithelium in Foxg1+ telencephalic neuroepithelium derived from hESCs. Treatment with a moderate concentration of SAG (30 nM; days 15-21; gray columns) partially suppressed the percentage of Pax6+ neuroepithelium and increased that of Gsh2+ neuroepithelium. Under this condition, relatively large domains of Pax6+ NE and Gsh2+ NE were frequently found side by side. At 500 nM, SAG treatment efficiently suppressed the expression of both Pax6 and Gsh2. $P<0.01$ and *$P<0.001$, Dunnett's test. (C) Expression of the medial ganglionic eminence marker Nkx2.1 in cortical neuroepithelium treated with 500 nM SAG. Nkx2.1+ neuroepithelium typically occupied 40-50% of Foxg1+ telencephalic NE. (D) Schematic of cortical morphogenesis in hESC culture in comparison with the fetal cortex. (E) Symmetrical divisions of apical progenitors near the luminal (apical) surface on days 28-29, which approached the luminal surface before their cell divisions with a vertical cleavage angle (see FIG. 14 for definition) and moved basally together. Visualized by pax6::venus hESCs (partial mixing with WT hESCs). (Scale bars, 200 µm in A and C.) Bars in graph, SEM.

When the neural epithelium was weakly ventralized (documents 18, 19) by a Hedgehog agonist (30 nM SAG for days 15-21), a substantial portion of foxg1::Venus-expressing neural epithelium expressed Gsh2, a marker for LGE (document 20) (FIG. 13O, arrowhead, and FIG. 19B). GAD65 positive GABAergic neurons was generated underneath this LGE neural epithelium, as seen in vivo (document 19) (FIG. 11P, red), whereas the rest of the telencephalic neural epithelium was largely positive for the cortical marker Pax6 (FIG. 13Q). Addition of high concentrations of SAG induced the MGE marker Nkx2.1 at the cost of Pax6 and Gsh2 expression (FIGS. 19B and C). Importantly, the neural epithelium treated with low SAG exhibited continuous formation of cortical (Pax6 positive)-LGE (Gsh2 positive) domains, as seen in vivo, suggesting that the improved culture condition allows continuous formation of pallial-subpallial structures in one aggregate by self-organization. In this continuously extending neural epithelium, the rolling side of the cortical neural epithelium (FIG. 13O-Q, arrows) was opposite to the cortex-LGE junction, consistent with the idea that the rolling and nonrolling sides represent the dorsal and ventral side of the cortical neural epithelium, respectively.

Figure 17:
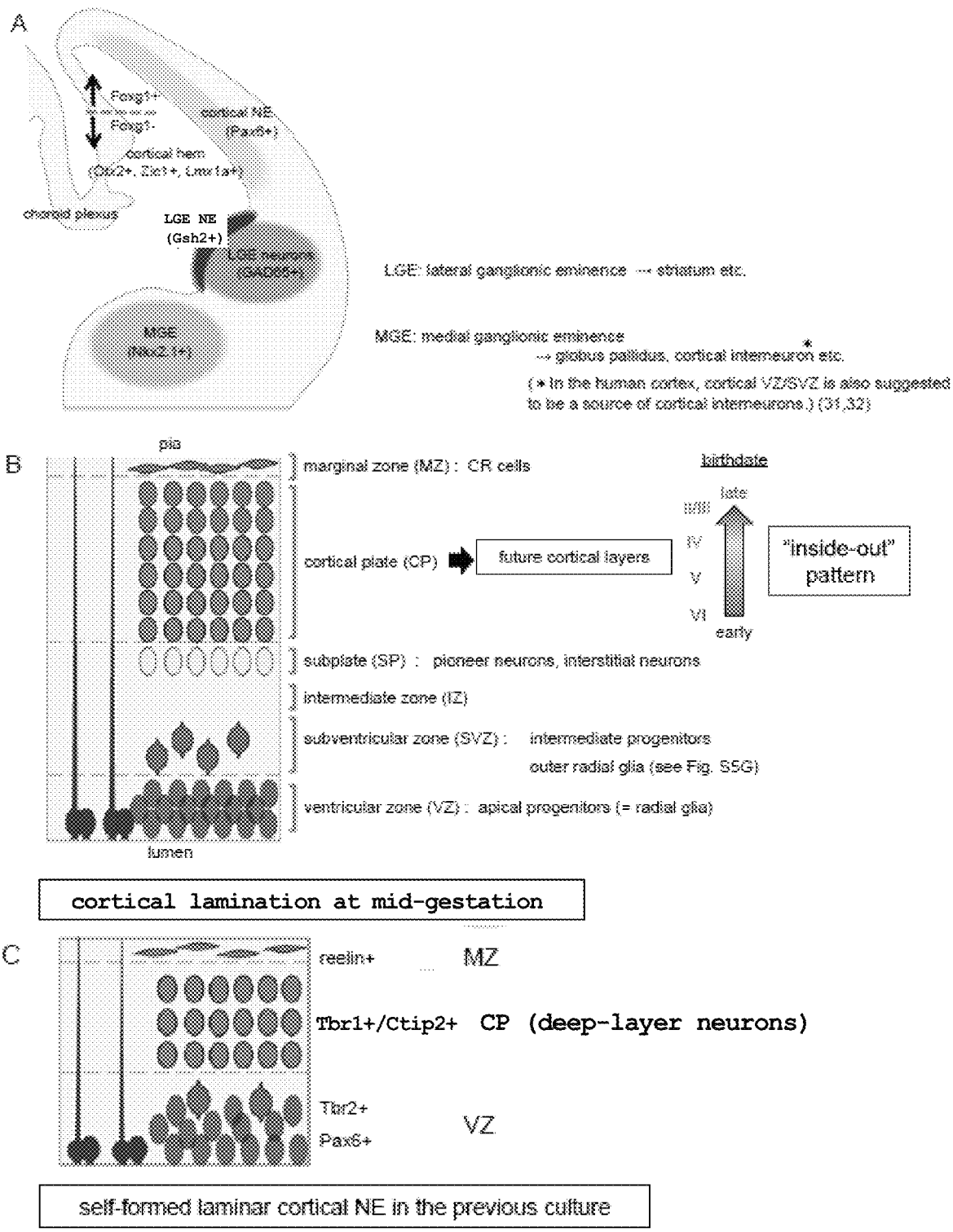
FIG. 17 shows development of fetal cortical neuroepithelium. (A) Schematic of the developing fetal telencephalon. (B) Schematic of the stratified structure of fetal cortical neuroepithelium at the early second trimester of human gestation (approximately embryonic week 13). (C) Schematic of the laminar cortical neuroepithelium structure generated in the previous self-organizing culture of hESCs. The structure is similar to the human cortical architecture during the early trimester.

In the embryo, the developing cortex evaginates by strong rounding of the pallial neural epithelium, whereas the embryonic pallium is immovable, because it is fixed to the neighboring tissues. The curvature of the embryonic neural epithelial region from the medial pallium (hippocampal region) to the dorsal part of the cortex is particularly strong (FIG. 17A). Since the position of the dorsocaudal side of hESC-derived cortical neural epithelium is not fixed and moves in the present three dimensional culture system, morphological change with rounding occurs. It is possible to infer that this reflects the strong rounding action of the embryonic dorsal cortex (FIG. 19D).

These findings demonstrate that the hESC-derived cortical neural epithelium self-forms a dome-like neural epithelium by morphological changes with asymmetrical rounding along the self-acquired dorsocaudal ventrorostral axis. Following this topological change, the apical surface of the neural epithelium becomes located inside of the cortical semispheres. In live imaging, neural stem cells frequently divided at the luminal surface while they underwent repetitive up-and-down nuclear movement (FIG. 13R and FIG. 19E; cell divisions were mostly symmetrical at these stages).

Morphological Separation of Three Cortical Neuronal Zones

Figure 14:
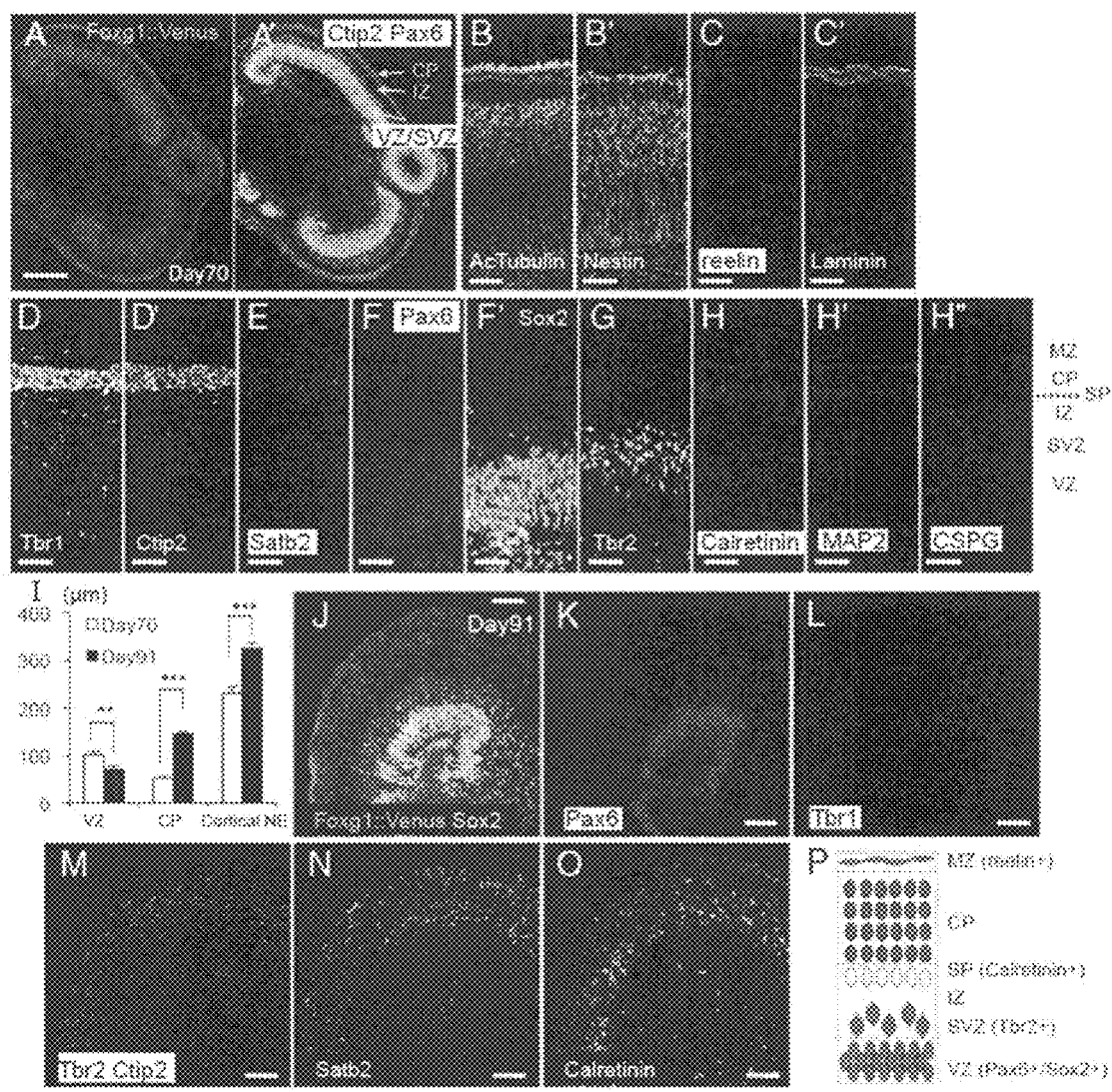
FIG. 14 shows self-formation of multiple zones in hESC-derived cortical neuroepithelium. (A and A') Sections of day 70 hESC-derived cortical neuroepithelium. Clear separation of ventricular zone (Pax6+), subventricular zone, intermediate zone, and cortical plate (Ctip2+) was seen even at the low-magnification view. (B-H") Immunostaining of day 70 cortical neuroepithelium with zone-specific markers. (I) Thickness of cortical neuroepithelium (cortical NE) and thickness of ventricular zone (VZ) and cortical plate (CP) on days 70 and 91. $P<0.01$; *$P<0.001$, Student t tests between day 70 cortical neuroepithelium samples and day 91 cortical neuroepithelium samples (n=6, each). (J-O) Immunostaining of day 91 cortical neuroepithelium with zone specific markers. (P) Schematic of the laminar structure seen in long-term culture of hESC-derived cortical neuroepithelium. (Scale bars, 400 µm in A; 50 µm in B-H"; 100 µm in J-O.) Bars in graph, SEM. Nuclear counter staining (blue), DAPI.

The improved culture conditions allowed hESC-derived cortical neural epithelium to grow even beyond culture day 42. On day 70, the thickness of hESC-derived cortical neural epithelium was 200 µm or larger (FIGS. 14A and A'). By this stage, the neural epithelium was morphologically stratified into the ventricular zone, subventricular zone, intermediate zone, cortical plate, and marginal zone (FIG. 14B-G and FIGS. 20A and B). The superficial-most layer of the marginal zone accumulated Laminin and contained Reelin positive cells (CR cells) (FIGS. 14C and C'). Cortical plate was formed beneath the marginal zone and contained deep-layer cortical neurons positive for Tbr1 and Ctip2 (FIGS. 14D and D'). The population of neurons expressing Satb2, a marker for superficial-cortical plate (document 21), was still relatively small at this stage (FIG. 14E). On day 70, the luminal ventricular zone was ~100 µm thick and contained Pax6 positive Sox2 positive neural stem cells/progenitors (FIGS. 14F and F') or cells called radial glia (document 22). In the upper part thereof, subventricular zone containing cells positive for Tbr2 was formed (FIG. 14G)

Figure 20:
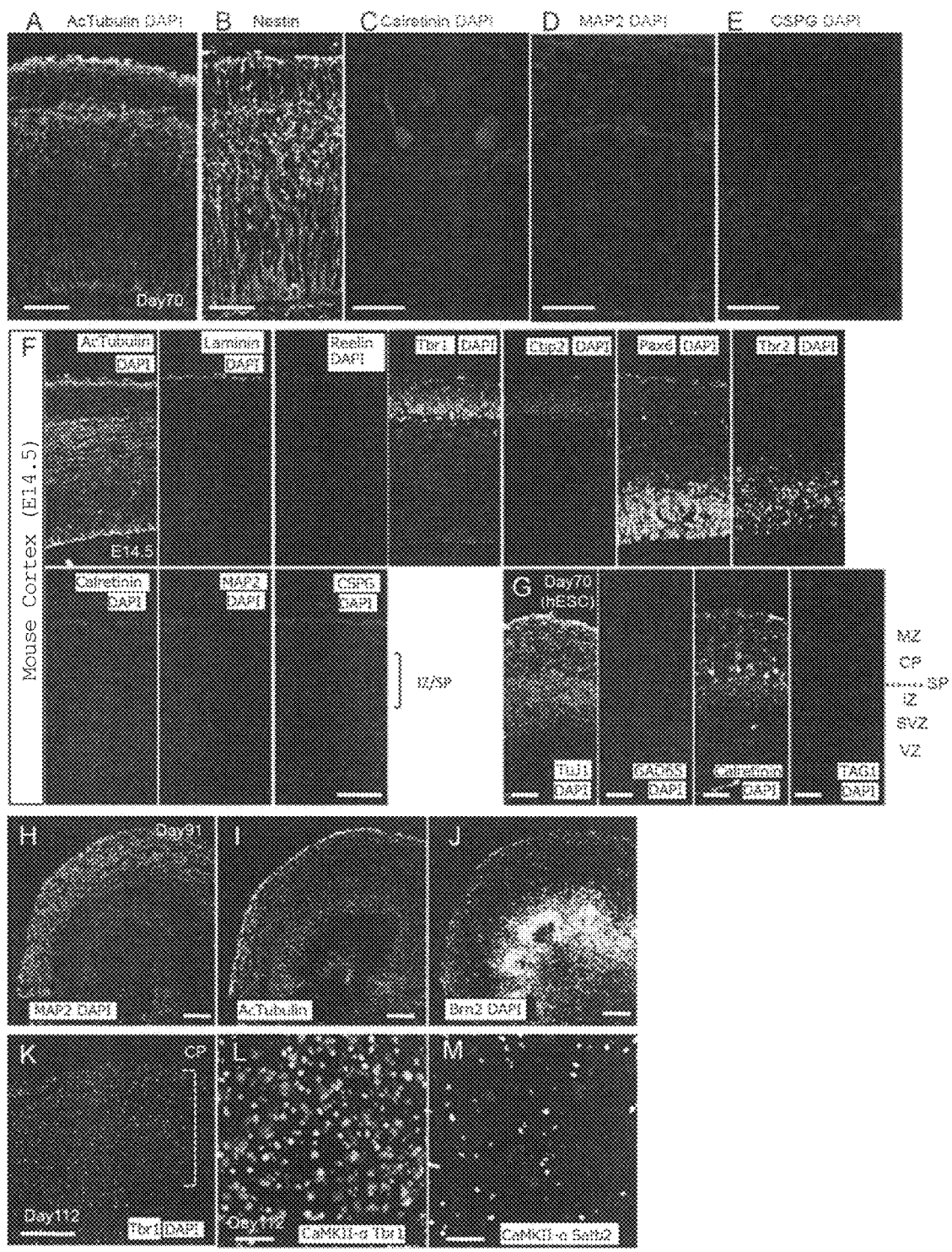
FIG. 20 shows subplate formation in hESC-derived cortical neuroepithelium. (A-E) Immunostaining of day 70 hESC-derived cortical neuroepithelium. (A and B) Clear morphological zone separations were observed in the cortical neuroepithelium even by simple staining with acetylated tubulin (AcTubulin; stabilized microtubules), DAPI (nuclear staining), and Nestin (intermediate filaments of neural progenitors). (C-E) High-magnification views of calretinin+ neurons (C), MAP2+ early neurites (D), and CSPG accumulation in the intermediate zone (E) of the cortical neuroepithelium. (F) Immunostaining of zone markers in the E14.5 mouse fetal cortex. (G) Immunostaining of day 70 hESC-derived cortical neuroepithelium. No substantial accumulation of GAD65+ interneurons in the cortical plate or TAG1+ corticofugal axons was observed. (H-J) Immunostaining of day 91 hESC-derived cortical neuroepithelium. The cortical neuroepithelium developed well and the stratified structure became much thicker (H and I). The cortical plate contained a number of Brn2+ superficial-layer neurons (J). (K) Immunostaining signals of Tbr1 in the day 112 hESC-derived cortical neuroepithelium. (L and M) Expression of the mature cortical neuron marker CaMKIIα in cortical plate of day 112 hESC-derived cortical neuroepithelium. The majority of these CaMKII neurons coexpressed Tbr1 (L) but not Satb2 (M). (Scale bars, 50 µm in A, B, G, L, and M; 20 µm in C-E; 100 µm in F and H-J; 200 µm in K.)

By this stage, a cell-sparse zone similar to the intermediate zone of second trimester developed between the cortical plate and subventricular zone. Immediately beneath the cortical plate was formed a layer of Calretinin positive cells with massive MAP2 positive neurites extending into this intermediate zone (FIGS. 14H and H' and FIGS. 20C and D). These characteristics resemble those of neurons in the subplate (e.g., early pioneer neurons for thalamo-cortical connections) that is prominent in the fetal human cortex (documents 23-25). Chondroitin sulfate proteoglycans (CSPGs) are accumulated in the embryonic subplate and its underlying intermediate zone (FIG. 20F, Lower Right, bracket) (document 26). Similarly, strong CSPG accumulation was observed in the corresponding zones in hESC-derived cortical neural epithelium (FIG. 14H" and FIG. 20E). These findings demonstrate that hESC-derived cortical neural epithelium can self-organize not only the cortical plate and marginal zone but also the subplate and intermediate zone in the same apico-basal order with embryo. At this stage, no substantial accumulation of GAD65 positive interneurons in the cortex or TAG1 positive corticofugal axons was observed (FIG. 20G).

By day 91, the cortical neural epithelium reached the thickness of 300-350 µm but still contained well-developed ventricular zone (FIG. 14I-K and FIGS. 20H and I). The cortical plate also became much thicker (~150 µm; FIG. 14I), and contained a number of superficial-layer neurons (Satb2 positive and Brn2 positive) in addition to Tbr1 positive and Ctip2 positive deep-layer cortical plate neurons (FIG. 14L-N and FIG. 20J). The subplate neurons (Calretinin positive) were still observed beneath the cortical plate (FIG. 14O).

Figure 15:
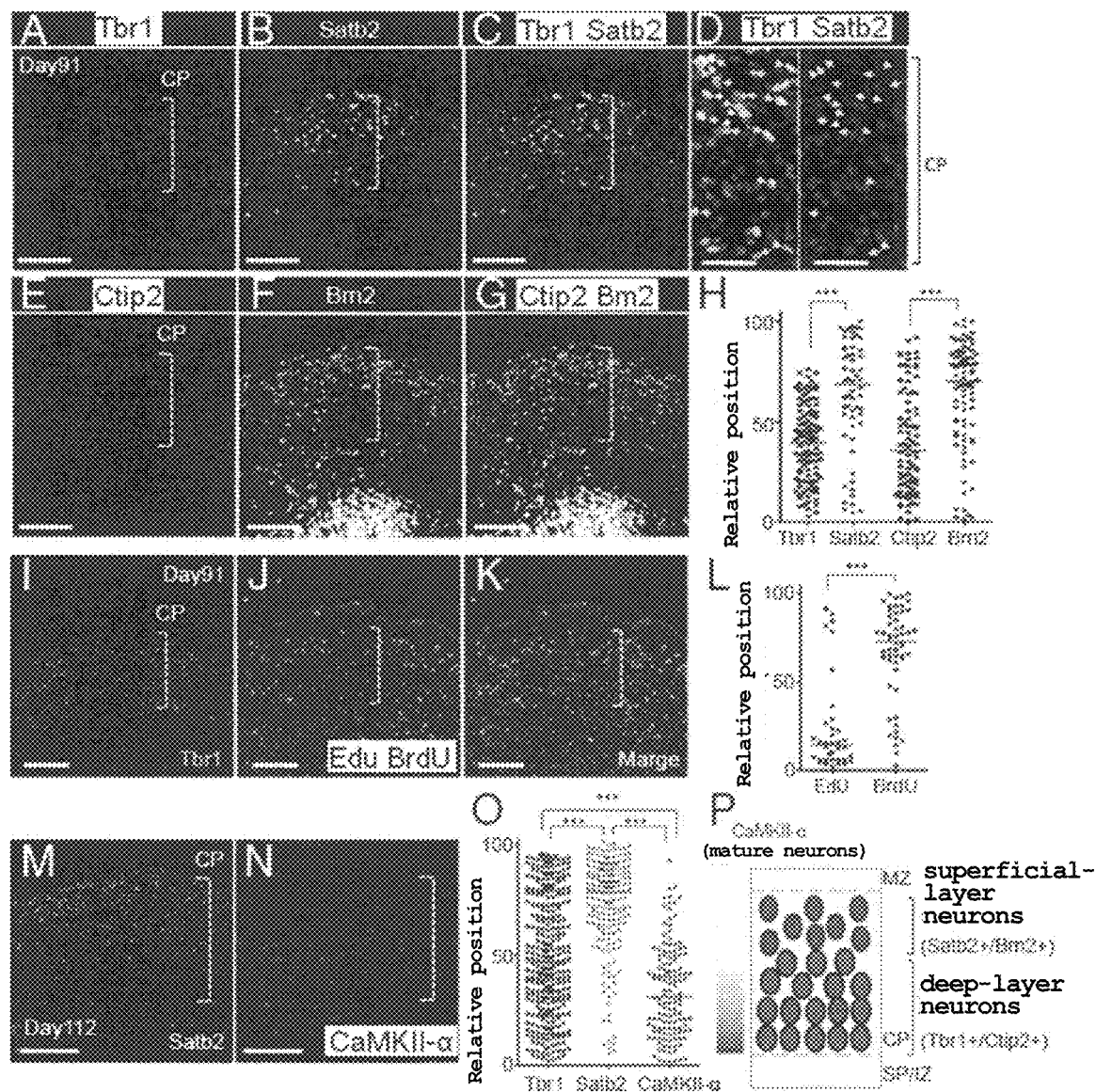
FIG. 15 shows basally biased localization of Satb2+ and Brn2+ cortical neurons in Cortical plate. (A-H) Cortical neurons positive for Satb2 and Brn2 (superficial-layer markers) were preferentially localized to the basal (superficial) portion of the hESC-derived cortical plate in day 91 culture. Most of the basally located Satb2+ cells were negative for the deep-layer marker Tbr1. (H) Distribution of marker-positive neurons within the cortical plate. For relative positions, the apical and basal boundaries of the cortical plate were defined as 0 and 100, respectively. *$P<0.001$. Mann-Whitney test. Red line, median. Counted neurons: Tbr1+ (n=105), Satb2+ (n=58), Ctip2+ (n=87), and Brn2+ (n=86). (I-L) Double-pulse labeling study using EdU (day 50; red; n=36) and BrdU (day 70; white; n=53). Analyzed by immunostaining on day 91. Statistical analysis was done as in H. (M-O) The mature cortical neuron marker CaMKIIα was preferentially expressed in Tbr1+ neurons located in the deep portion of the cortical plate on day 112. The cortical neurons were cultured on a Transwell filter during days 78-112 to support survival of mature neurons. (O) Plotting was done as in H. *$P<0.001$. Kruskal-Wallis test with a post hoc multiple comparison test. Numbers of neurons counted: Tbr1+ (n=293), Satb2+ (n=177), and CaMKIIα+ (n=132). (P) Schematic of neuronal distributions within the hESC-derived cortical neuroepithelium on days 91 and 112. (Scale bars, 100 µm in A-C, E-G, and I-K; 50 µm in D; 200 µm in M and N.) Nuclear counter staining (blue), DAPI.

The morphological layer structural separation seen in the long term culture (summarized in FIG. 14P) mimics the histology of the human fetal cortex during early second-trimester stages (documents 25, 27). Moreover, within the hESC-derived cortical plate, superficial-layer neurons (Satb2 positive and Brn2 positive) preferentially localized more superficially to deep-layer neurons (Tbr1 positive and Ctip2 positive) (FIG. 15A-H). Furthermore, when 1-day labeling was done with EdU on day 50 and then with BrdU on day 70, EdU- and BrdU-labeled cells were preferentially located on the deep and superficial sides, respectively, on day 91 (FIG. 15I-L). These findings indicate that the there is a biased tendency in the localization of neurons reminiscent of the inside-out pattern during fetal corticogenesis (documents 5, 6), in which late-born cortical neurons are located outside and early-born cortical neurons are inside. Consistent with this idea, on day 112, the mature cortical neuron marker CaMKIIα was preferentially seen in the luminal two-thirds portion of the hESC-derived cortex, which predominantly expressed Tbr1 but not Satb2 (FIG. 15M-O and FIG. 20K). Indeed, at the cellular level, the majority of these CaMKIIα neurons coexpressed Tbr1 but not Satb2 (FIGS. 20L and M; FIG. 15P for summary).

Appearance of Human-Specific Neural Stem Cells/Progenitors in the oSVZ

Figure 16:
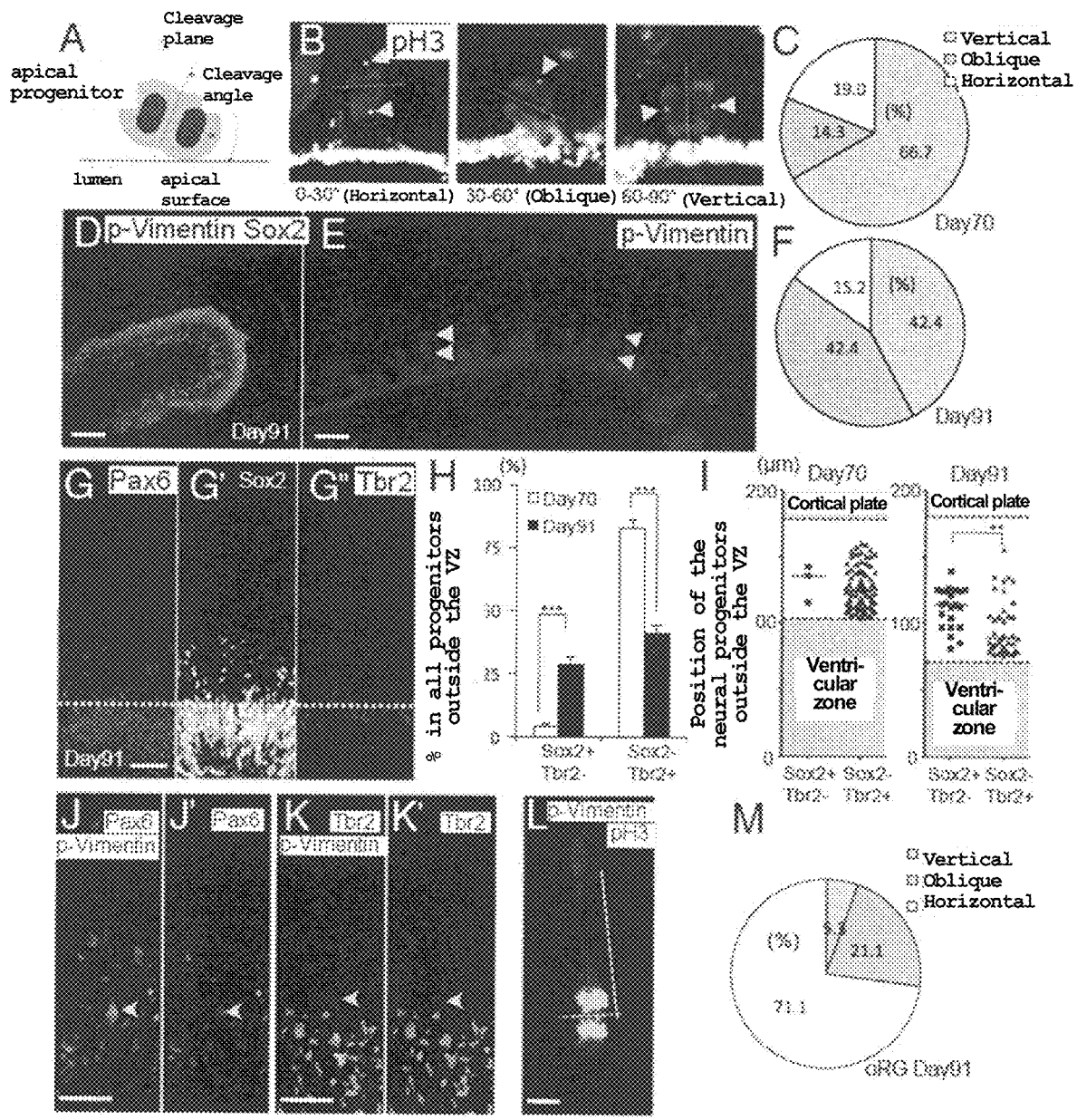
FIG. 16 shows appearance of oRG-like progenitors. (A-F) Percentages of apical neural stem cells/progenitors with vertical (cleavage angle at 60-90°) and nonvertical (0-30° and 30-60°) cleavages (A and B) in the day 70 (C) and day 91 (D-F) hESC-derived cortical neuroepithelium. p-Vimentin, M-phase marker. Arrowhead, pericentrin. Cells analyzed: n=42 (day 70) and n=33 (day 91). (G-I) Basal neural stem cells/progenitors (Pax6+, Sox2+) and intermediate neural stem cells/progenitors (Tbr2+) in the SVZ of day 91 culture. (H) Percentages of Sox2+/Tbr2− and Sox2−/Tbr2+ neural stem cells/progenitors within all neural stem cells/progenitors (Sox2+ and/or Tbr2+) in the cortical plate. The percentage of Sox2+/Tbr2− neural stem cells/progenitors increased from day 70 to day 91, whereas Sox2−/Tbr2+ neural stem cells/progenitors decreased in proportion. *$P<0.001$, Student t tests between day 70 and day 91 samples. Neural stem cells/progenitors outside of ventricular zone from four cortical neuroepithelium domains from each day were counted. (I) On day 91, Sox2+/Tbr2− neural stem cells/progenitors tended to localize farther from the ventricular surface than Sox2−/Tbr2+ neural stem cells/progenitors (Right). *$P<0.001$, Mann-Whitney test. Red line, median. (J-M) Pax6+ p-Vimentin+ neural stem cells/progenitors had a long basal process extending toward the pia but not an apical process (J and J'), whereas these neural stem cells/progenitors were negative for Tbr2 (K and K'). A majority (>70%) of these neural stem cells/progenitors possessing a basal process showed a horizontal type of cleavage angle (60-90°; L and M) (n=37). (Scale bars, 100 µm in D; 25 µm in E; 50 µm in G, J, and K; 10 µm in L.) Bars in graph, SEM. Nuclear counter staining (blue), DAPI.

Finally, cortical neural stem cell/progenitor dynamics in the long-term cultured hESC-derived cortex was investigated. Previous in vivo studies have revealed that nonvertical division of luminal neural stem cells is increased at an advanced stage, and many of the apical neural progenitors are produced through asymmetrical divisions (documents 28, 29). In the present culture, proliferating luminal neural stem cells on day 70 preferentially divided with a "vertical" cleavage plane (60-90°; FIG. 16A-C), causing segregation of daughter cells parallel to the luminal surface. In contrast, on day 91, proliferating neural stem cells (phospho-Vimentin positive) showed a higher frequency of nonvertical divisions (FIG. 16D-F).

Figure 21:
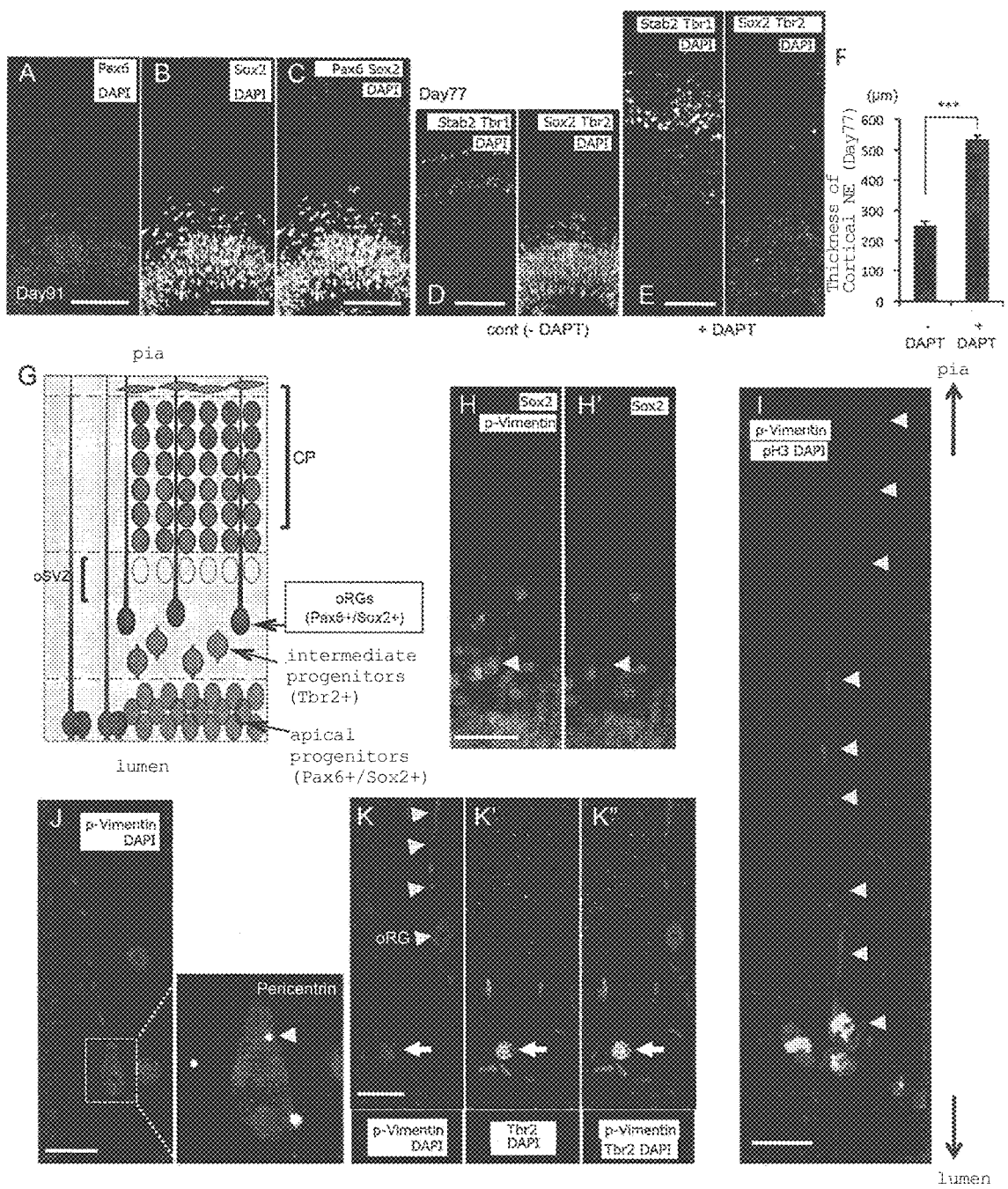
FIG. 21 shows oRG-like neural stem cells/progenitors in the oSVZ. (A-C) Immunostaining of Pax6 and Sox2 in apical and basal (SVZ) neural stem cells/progenitors within the hESC-derived cortical neuroepithelium on day 91. The majority of Sox2 positive cells express Pax6 (C). (D-F) Effects of Notch signal inhibition on the expression of neural stem cells/progenitor and neuron markers in cortical neuroepithelium. The Notch inhibitor treatment (10 µM DAPT, days 70-77) increased Sox2− Tbr2+ intermediate neural stem cells/progenitors, whereas Sox2+ Tbr2− cells rarely remained after the treatment (D and E). Satb2+ neurons also increased by DAPT treatment (D and E). An increase of cortical neuroepithelium thickness also observed after the treatment (F). ***$P<0.001$, Student t tests between with DAPT (n=6) and without DAPT (n=5) treatment. (G) Schematic of oRG neural stem cells/progenitors in the human fetal outer SVZ. (H and H') Phospho-vimentin+ neural stem cells/progenitors in the SVZ expressed Sox2. (I) Phospho-vimentin+ neural stem cells/progenitors in the SVZ with a long apical process extending toward the pial surface. (J) Phospho-vimentin+ SVZ neural stem cells/progenitors with a basal process carried a pericentin+ centrosome in the neurons. During mitosis, two pericentin+ centrioles were found for dividing cells. (K-K") Unlike oRG-like neural stem cells/progenitors, no Tbr2+ phospho-vimentin+ neural stem cells/progenitors in the hESC-derived cortical neuroepithelium possessed a basal process (nor an apical process). (Scale bars, 100 µm in A-E; 25 µm in H-K.)

Both on days 70 and 91, the SVZ contained a number of Tbr2 positive, Sox2 negative, Pax6 negative intermediate progenitors (FIGS. 14G and M). Interestingly, on day 91, the outer portion of SVZ accumulated another population of phospho-Vimentin positive neural stem cells/progenitors that were Tbr2 negative Sox2 positive, Pax6 positive (FIG. 16G-G" and FIG. 21A-C). The population of these cells was relatively small in percentage on day 70 and became prominent by day 91 (FIG. 16H). On day 91, this Tbr2 negative and Sox2 positive cell population was biased to localize more apically, in contrast to the luminally deviated location of Tbr2 positive and Sox2 negative intermediate progenitors (FIG. 16I, Right). Interestingly, these two neural stem cells/progenitors responded differently to Notch signal inhibitor, which strongly decreases luminal neural stem cells/progenitors by inducing precocious neuronal differentiation. The Notch signal inhibitor increased Tbr2 positive and Sox2 negative intermediate progenitors, whereas Tbr2 negative and Sox2 positive cells rarely remained after the treatment (FIG. 21D-F).

Recent studies have reported that a Tbr2 negative, Sox2 positive, Pax6 positive neural stem cell/progenitor population distinct from Tbr2 positive intermediate progenitors is accumulated in human corticogenesis oSVZ of later stages (FIG. 21G) (documents 11, 12). These neural stem cells/progenitors, termed oRG (or OSVZ stem cells) (documents 11, 12), are thought to contribute to the massive generation of superficial-layer neurons, which is characteristic of the human cortex. The oRG cells have a process extending to the apical surface and lack an luminal process unlike luminal progenitors. Similarly, the Tbr2 negative, Sox2 positive, Pax6 positive neural stem cells/progenitors in the day 91 hESC-derived cortical neural epithelium also had an apical process but not an luminal process (FIG. 16J-K' and FIGS. 21H, H', and I). These cells had a pericentrin positive basal body in the soma located in the SVZ (FIG. 21J), unlike luminal neural stem cells, in which basal bodies are located near the luminal surface. Like in vivo oRG, the cleavage plane of the hESC-derived oRG-like cells tended to be horizontal (FIGS. 16L and M). No apical processes were found in Tbr2 positive progenitors (phospho-Vimentin positive; FIG. 21K-K"), as is the case for in vivo intermediate progenitors.

Taken together, these findings indicate that the self-organized cortical neural epithelium recapitulates the neural stem cell/progenitor dynamics seen at advanced stages of human corticogenesis, including the emergence of oRG-like progenitors.

In this study, it was demonstrated that hESC-derived cortical neural epithelium can execute their internal programs to self-organize the axial pattern and multiple zone separation seen in human fetal brain. The culture system of the present invention allowed healthy growth of hESC-derived cortical neural epithelium for long-term under suspension culture condition, even beyond 13 wk. Eventually, the cortical neural epithelium became around 350 μm thick and contained multiple laminar structure as seen in the fetal cortex at the human second trimester (starting from embryonic week 11) (documents 30). This makes a clear contrast to the limitation of the previous 3D culture, which could support the cortical neural epithelium up to the tissue maturation corresponding to the first trimester. The culture method of the present invention also recapitulated another aspect of human second-trimester neocorticogenesis, i.e., the appearance of oRG-like neural stem cells/progenitors on day 91 (13 wk) of culture. These observations also suggest that the developmental speed in the tissue self-organized in the method of the present invention is roughly comparable to the development in the fetal brain.

An important effect of this culture is that the internally programmed corticogenesis proceeds in the continuously extending neural epithelium for a long period. The self-forming mechanism for this intracortical polarity is an intriguing topic for future investigation. In addition, the rounding morphological change of the hESC-derived cortical neural epithelium exhibits asymmetric movements along the self-formed polarity.

In addition to the polarity within cortical neural epithelium, the culture system of the present invention is also applicable to the study of the dorsal-ventral specification of the whole telencephalic region. Notably, under the partially ventralized conditions (FIG. 13O-Q), the hESC-derived neural epithelium recapitulated the cortex and LGE (striatum anlage) in adjacent positions as seen in vivo, by self-organization, whereas even stronger Hedgehog signals induce MGE formation.

The optimized culture system indicated in this study allowed the recapitulation of the complex laminar formation of cortex: i.e. the formation of ventricular zone, subventricular zone, intermediate zone, subplate, cortical plate, and marginal zone. The subplate is a particularly predominant structure in primates (sometimes, also called layer VII), and is thought to be formed with early-born neurons within the cortex (e.g., pioneer neurons) (documents 24, 25). Although subplate is only transiently present in the fetal cortex, some of its derivatives exist in the adult brain as interstitial neurons in the adult white matter (document 33). Because the subplate disappears postnatally, its investigation is not easy, especially in humans, and thus, our system should be important in studying this little understood neuronal layer. In addition, our culture system may be applicable to studies of the inside-out laminar formation in the human fetal cortex, including the pathogenesis of lissencephaly.

Finally, our culture system is very advantageous in studying the role of oRG neural stem cells/progenitors in human corticogenesis. It is presumably advantageous for the gyrencephalic human cortex to involve this type of neural stem cells/progenitors that keep on dividing multiple times to generate a number of superficial neurons. To date, there are no specific molecular markers reported for demarcating oRG, and the distinction between oRG and luminal neural stem cells (both are Sox2 positive, Pax6 positive, and Tbr2 negative) mainly depends on their cellular morphology, behavior, and location. Therefore, the extent of oRG study has been fairly limited in the case of dissociation culture that lacks the topological context. In contrast, the culture system of the present invention provides a great advantage in this respect, because it has the 3D context of the developing human cortex. Very recently, it was reported a similar observation of the oRG appearance in the stratified cortical tissue generated from human pluripotent stem cells (documents 34). This study uses a nonselective differentiation method which can stochastically obtain specification of brain regions (unlike our reproducibly cortex-selective differentiation culture).

While the present invention has been described with emphasis on preferred embodiments, it is obvious to those skilled in the art that the preferred embodiments can be modified. The present invention intends that the present invention can be embodied by methods other than those described in detail in the present specification. Therefore, the present invention encompasses all modifications encompassed in the gist and scope of the appended "CLAIMS."

The contents disclosed in any publication cited herein, including patents and patent applications, are hereby incorporated in their entireties by reference, to the extent that they have been disclosed herein.

REFERENCE DOCUMENTS

1 Molyneaux B J, Arlotta P, Menezes J R, Macklis J D. (2007) Neuronal subtype specification in the cerebral cortex. Nat Rev Neurosci. 8:427-437.

2 Hebert J M, Fishell G. (2008) The genetics of early telencephalon patterning: some assembly required. Nat Rev Neurosci 9:678-685.

3 Bielle F, et al. (2005) Multiple origins of Cajal-Retzius cells at the borders of the developing pallium. Nat Neurosci. 8:1002-1012.

4 Bystron I, Blakemore C, Rakic P. (2008) Development of the human cerebral cortex: Boulder Committee revisited. Nat Rev Neurosci. 9:110-122.

5 Rakic P. (1974) Neurons in rhesus monkey visual cortex: systematic relation between time of origin and eventual disposition. Science. 183:425-427.

6 Shen Q. et al. (2006) The timing of cortical neurogenesis is encoded within lineages of individual progenitor cells. Nat Neurosci 9:743-751.

7 Eiraku M. et al. (2008) Self-organized formation of polarized cortical tissues from ESCs and its active manipulation by extrinsic signals. Cell Stem Cell 3: 519-532.

8 Watanabe K. et al. (2005) Directed differentiation of telencephalic precursors from embryonic stem cells. Nat Neurosci 8:288-296.

9 Nasu M, et al. (2012) Robust formation and maintenance of continuous stratified cortical neuroepithelium by laminin-containing matrix in mouse ES cell culture. PLoS One 7:e53024.

10 Mariani J. et al. (2012) Modeling human cortical development in vitro using induced pluripotent stem cells. Proc Natl Acad Sci USA. 109:12770-12775.

11 Hansen D V, Lui J H, Parker P R, Kriegstein A R. (2010) Neurogenic radial glia in the outer subventricular zone of human neocortex. Nature 464:554-561.

12 Fietz S A, et al. (2010) OSVZ progenitors of human and ferret neocortex are epithelial-like and expand by integrin signaling. Nat Neurosci. 13:690-699.

13 Wang X, Tsai J W, LaMonica B, Kriegstein A R. (2011) A new subtype of progenitor cell in the mouse embryonic neocortex. Nat Neurosci. 14:555-561.

14 Shitamukai A, Konno D, Matsuzaki F. (2011) Oblique radial glial divisions in the developing mouse neocortex induce self-renewing progenitors outside the germinal zone that resemble primate outer subventricular zone progenitors. J Neurosci. 31:3683-3695.

15 Nakano T, et al. (2012) Self-formation of optic cups and storable stratified neural retina from human ESCs. Cell Stem Cell 10:771-785.

16 Watanabe K, et al. (2007) A ROCK inhibitor permits survival of dissociated human embryonic stem cells. Nature Biotechnol. 25:681-686.

17 Storm E E, et al. (2006) Dose-dependent functions of Fgf8 in regulating telencephalic patterning centers. Development 133:1831-1844.

18 Fuccillo M, Rallu M, McMahon A P, Fishell G (2004) Temporal requirement for hedgehog signaling in ventral telencephalic patterning. Development 131:5031-5040.

19 Danjo T, et al. (2011) Subregional specification of embryonic stem cell-derived ventral telencephalic tissues by timed and combinatory treatment with extrinsic signals. J Neurosci. 31:1919-1933.

20 Yun K, Potter S, Rubenstein J L (2001) Gsh2 and Pax6 play complementary roles in dorsoventral patterning of the mammalian telencephalon. Development 128:193-205.

21 Alcamo E A, et al. (2008) Satb2 regulates callosal projection neuron identity in the developing cerebral cortex. Neuron 57:364-377.

22 Doetsch F. (2003) The glial identity of neural stem cells. Nat Neurosci. 6:1127-1134.

23 Kostovic I, Rakic P. (1990) Developmental history of the transient subplate zone in the visual and somatosensory cortex of the macaque monkey and human brain. J Comp Neurol. 297:441-470.

24 Wang W Z, et al. (2010) Subplate in the developing cortex of mouse and human. J Anat. 217:368-380.

25 Judas M, Sedmak G, Kostovic I. (2013) The significance of the subplate for evolution and developmental plasticity of the human brain. Front Hum Neurosci. 7:423.

26 Sheppard A M, Pearlman A L. (1997) Abnormal reorganization of preplate neurons and their associated extracellular matrix: an early manifestation of altered neocortical development in the reeler mutant mouse. J Comp Neurol. 378:173-179.

27 Bayer S A and Altman J. (2005) Atlas of Human Central Nervous System Development, volume 3: The Human Brain During the Second Trimester (CRC Press, Boca Raton)

28 LaMonica B E, Lui J H, Hansen D V, Kriegstein A R. (2013) Mitotic spindle orientation predicts outer radial glial cell generation in human neocortex. Nat Commun. 4:1665.

29 Taverna E, Huttner W B. (2010) Neural progenitor nuclei IN motion. Neuron 67:906-914.

30 Bayatti N, et al. (2008) A molecular neuroanatomical study of the developing human neocortex from 8 to 17 postconceptional weeks revealing the early differentiation of the subplate and subventricular zone. Cereb Cortex 18:1536-1548.

31 Letinic K, Zoncu R, Rakic P. (2002) Origin of GABAergic neurons in the human neocortex. Nature. 417:645-649.

32 Rakic S, Zecevic N. (2003) Emerging complexity of layer I in human cerebral cortex. Cereb Cortex. 13:1072-1083.

33 Judas M, Sedmak G, Pletikos M. (2010) Early history of subplate and interstitial neurons: from Theodor Meynert (1867) to the discovery of the subplate zone (1974). J Anat. 217(4):344-367.

34 Lancaster M A, et al. (2013) Cerebral organoids model human brain development and microcephaly. Nature. 501:373-379.

35 Bayer S A and Altman J. (2004) Atlas of Human Central Nervous System Development, volume 2: The Human Brain During the Third Trimester (CRC Press, Boca Raton)

INDUSTRIAL APPLICABILITY

According to the present invention, telencephalon or a partial tissue thereof (cerebral cortex, basal ganglion, hippocampus, choroid plexus etc.) having a higher order structure like telencephalon in vivo, or a progenitor tissue thereof can be induced from pluripotent stem cells in vitro. Therefore, the present invention is useful for practicalization of regenerative medicine in the cranial nerve region.

This application is based on a patent application No. 2013-242394 filed in Japan (filing date: Nov. 22, 2013), the contents of which are incorporated in full herein.

The invention claimed is:

1. A method of producing a cell aggregate comprising telencephalon, comprising steps (a), (b), and (c):
    (a) culturing dispersed pluripotent stem cells in suspension to allow for aggregate formation,
    (b) culturing the aggregate obtained in (a) in suspension in the presence of a wingless-type mouse mammary tumor virus integration site (Wnt) signal inhibitor and a transforming growth factor β (TGFβ) signal inhibitor to induce expression of Foxg1 gene until not less than 50% of the cell aggregates in the culture are Foxg1 positive, thereby producing a Foxg1-positive aggregate, and
    (c) further culturing the Foxg1-positive aggregate in suspension under an oxygen partial pressure of 30-60%,
    wherein the Wnt signal inhibitor is selected from the group consisting of IWR-1-endo(4-[(3aR,4S,7R,7aS)-1,3,3a,4,7,7a-hexahydro-1,3-dioxo-4,7-methano-2H-isoindol-2-yl]-N-8-quinolinyl-benzamide), IWP-2, XAV939, Dkk1, Cerberus protein, Wnt receptor inhibitors, soluble Wnt receptors, Wnt antibodies, casein kinase inhibitor, and dominant negative Wnt protein, and
    wherein the TGFβ signal inhibitor is selected from the group consisting of SB431542 (4-(5-benzol[1,3]dioxol-5-yl-4-pyridin-2-yl-1H-imidazol-2-yl)-benzamide), LY-364947, SB-505, and A-83-01.

2. The production method according to claim 1, wherein the obtained cell aggregate comprises a tissue selected from the group consisting of cerebral cortex, basal ganglion, hippocampus and choroid plexus.

3. The production method according to claim 2, wherein the obtained cell aggregate comprises a cerebral cortical tissue having a multilayered structure comprising marginal zone, cortical plate, subplate, intermediate zone, subventricular zone and ventricular zone from a superficial portion to a deep portion.

4. A method of producing a mature hippocampal neuron, comprising dispersing the cell aggregate comprising hippocampus, which is obtained by the production method according to claim 2, and further subjecting the dispersed cells to adhesion culture to induce a mature hippocampal neuron from the cells.

5. The production method according to claim 1, wherein the suspension culture under an oxygen partial pressure of 30-60% is performed in a medium not containing a Wnt signal inhibitor and a TGFβ signal inhibitor, and in the presence of a Wnt signal enhancer, and wherein the Wnt signal enhancer is selected from the group consisting of a GSK-3β inhibitor, recombinant Wnt3a, Wnt agonist, and R-Spondin.

6. The production method according to claim 5, wherein the GSK-3β inhibitor is selected from the group consisting of CHIR99021 (6-[[2-[[4-(2,4-dichlorophenyl)-5-(5-methyl-1H-imidazol-2-yl)-2-pyrimidinyl]amino]ethyl]amino]-3-pyridinecarbonitrile), Kenpaullone, and 6-Bromoindirubin-3'-oxime (BIO).

7. The production method according to claim 1, wherein the suspension culture under an oxygen partial pressure of 30-60% is performed in a medium not containing a Wnt signal inhibitor and a TGFβ signal inhibitor, and in the presence of a Wnt signal enhancer and a bone morphogenetic factor signal transduction pathway activating substance, and wherein the Wnt signal enhancer is selected from the group consisting of a GSK-3β inhibitor, recombinant Wnt3a, Wnt agonist, and R-Spondin.

8. The production method according to claim 7, wherein the bone morphogenetic factor signal transduction pathway activating substance is selected from the group consisting of BMP2, BMP4, BMP7, and GDF5, and wherein the GSK-3β inhibitor is selected from the group consisting of CHIR99021 (6-[[2-[[4-(2,4-dichlorophenyl)-5-(5-methyl-1H-imidazol-2-yl)-2-pyrimidinyl]amino]ethyl]amino]-3-pyridinecarbonitrile), Kenpaullone, and 6-Bromoindirubin-3'-oxime (BIO).

9. The production method according to claim 1, comprising treating the cell aggregate with a sonic hedgehog (shh) signal agonist, wherein the shh signal agonist is selected from the group consisting of a protein belonging to the Hedgehog family, Shh, Shh receptor agonist, Purmorphamine, and SAG (N-methyl-N'-(3-pyridinylbenzyl)-N'-(3-chlorobenzo[b]thiophene-2-carbonyl)-1,4-diaminocyclohexane).

10. The production method according to claim 9, wherein the obtained cell aggregate comprises basal ganglion.

11. The production method according to claim 1, comprising treating the cell aggregate with fibroblast growth factor 8 (FGF8).

12. The production method according to claim 11, wherein the obtained cell aggregate comprises rostral cerebral cortex.

13. The production method according to claim 1, wherein the pluripotent stem cells are embryonic stem cells or induced pluripotent stem cells.

14. The production method according to claim 1, wherein the pluripotent stem cells are derived from human.

15. The production method according to claim 1, wherein the suspension culture is performed in the absence of feeder cells.

16. The method according to claim 1, wherein step (c) comprises culturing in a medium comprising a chemically defined lipid concentrate that is a lipid mixture containing cholesterol, DL-α-tocopherol, arachidonic acid, linolenic acid, linoleic acid, myristic acid, oleic acid, palmitic acid, palmitoleic acid, and stearic acid, each of which is purified.

17. The method according to claim 1, wherein step (c) comprises culturing in a medium comprising a heparin.

18. The method according to claim 1, wherein step (c) comprises culturing in a medium comprising a basement membrane component selected from a group consisting of type IV collagen, laminin, heparan sulfate proteoglycan, entactin, and basement membrane preparation derived from Engelbreth Holm Swam (EHS) mouse sarcoma.

19. A method of producing a cell aggregate comprising telencephalon, comprising
(i) culturing dispersed pluripotent stem cells in suspension to allow for aggregate formation,
(ii) culturing the aggregate obtained in (i) in suspension in the presence of a wingless-type mouse mammary tumor virus integration site (Wnt) signal inhibitor and a transforming growth factor β (TGFβ) signal inhibitor to induce expression of Foxg1 gene until not less than 50% of the cell aggregates in the culture are Foxg1-positive, thereby obtaining a Foxg1-positive aggregate,
(iii) further culturing the Foxg1-positive aggregate obtained in (ii) in suspension in the presence of a Wnt signal enhancer and a bone morphogenetic factor signal transduction pathway activating substance, and
(iv) further culturing the cell aggregate obtained in (iii) in suspension in the absence of a Wnt signal enhancer and a bone morphogenetic factor signal transduction pathway activating substance,
wherein the Wnt signal inhibitor is selected from the group consisting of IWR-1-endo(4-[(3aR,4S,7R,7aS)-1,3,3a,4,7,7a-hexahydro-1,3-dioxo-4,7-methano-2H-isoindol-2-yl]-N-8-quinolinyl-benzamide), IWP-2, XAV939, Dkk1, Cerberus protein, Wnt receptor inhibitors, soluble Wnt receptors, Wnt antibodies, casein kinase inhibitor, and dominant negative Wnt protein,
wherein the TGFβ signal inhibitor is selected from the group consisting of SB431542 (4-(5-benzol[1,3]dioxol-5-yl-4-pyridin-2-yl-1H-imidazol-2-yl)-benzamide), LY-364947, SB-505, and A-83-01,
wherein the Wnt signal enhancer is selected from the group consisting of a GSK-3β inhibitor, recombinant Wnt3a, Wnt agonist, and R-Spondin, and
wherein the suspension culture in (iii) and (iv) is performed under an oxygen partial pressure of 30-60%.

20. The production method according to claim 19, wherein the produced cell aggregate comprises, in continuous neuroepithelium, a cerebral cortical tissue, a choroid plexus tissue, and a hippocampal tissue.

21. The production method according to claim 19, wherein the produced cell aggregate comprises, in continuous neuroepithelium, a hippocampal tissue comprising a dentate gyrus tissue, and an Ammon's horn tissue.

22. The production method according to claim 21, wherein the hippocampal tissue further comprises cortical hem in the continuous neuroepithelium.

23. The production method according to claim 19, wherein the produced cell aggregate comprises an Ammon's horn tissue.

24. The production method according to claim 19, wherein the bone morphogenetic factor signal transduction pathway activating substance is selected from the group consisting of BMP2, BMP4, BMP7 and GDF5, and wherein the GSK-3β inhibitor is selected from the group consisting of CHIR99021 (6-[[2-[[4-(2,4-dichlorophenyl)-5-(5-methyl-1H-imidazol-2-yl)-2-pyrimidinyl]amino]ethyl]amino]-3-pyridinecarbonitrile), Kenpaullone, and 6-Bromoindirubin-3'-oxime (BIO).

25. A method of producing a cell aggregate comprising telencephalon, comprising steps (a) and (b):
  (a) culturing an aggregate of pluripotent stem cells in suspension in the presence of a wingless-type mouse mammary tumor virus integration site (Wnt) signal inhibitor and a transforming growth factor β (TGFβ) signal inhibitor for 15 to 20 days, and
  (b) further culturing the cell aggregate obtained in (a) in suspension under an oxygen partial pressure of 30-60% in a medium that does not contain a Wnt signal inhibitor or a TGFβ signal inhibitor,
  wherein the Wnt signal inhibitor is selected from a group consisting of IWR-1-endo(4-[(3aR,4S,7R,7aS)-1,3,3a,4,7,7a-hexahydro-1,3-dioxo-4,7-methano-2H-isoindol-2-yl]-N-8-quinolinyl-benzamide), IWP-2, XAV939, Dkk1, Cerberus protein, Wnt receptor inhibitors, soluble Wnt receptors, Wnt antibodies, casein kinase inhibitor, and dominant negative Wnt protein, and
  wherein the TGFβ signal inhibitor is selected from a group consisting of SB431542 (4-(5-benzol[1,3]dioxol-5-yl-4-pyridin-2-yl-1H-imidazol-2-yl)-benzamide), LY-364947, SB-505, and A-83-01.

\* \* \* \* \*